(12) United States Patent
Zink, II et al.

(10) Patent No.: US 11,096,835 B2
(45) Date of Patent: Aug. 24, 2021

(54) METHODS FOR SEALING ABSORBENT CORES ON ABSORBENT ARTICLES

(71) Applicant: The Procter & Gamble Company, Cincinnati, OH (US)

(72) Inventors: Ronald Joseph Zink, II, Blue Ash, OH (US); Ricky Reynaldo Yanez, Jr., Cincinnati, OH (US); Uwe Schneider, Cincinnati, OH (US); Jeffry Rosiak, Loveland, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 289 days.

(21) Appl. No.: 15/837,056

(22) Filed: Dec. 11, 2017

(65) Prior Publication Data

US 2018/0168885 A1    Jun. 21, 2018

Related U.S. Application Data

(60) Provisional application No. 62/436,053, filed on Dec. 19, 2016.

(51) Int. Cl.
*A61F 13/15* (2006.01)
*A61F 13/496* (2006.01)
(Continued)

(52) U.S. Cl.
CPC .. *A61F 13/15739* (2013.01); *A61F 13/15593* (2013.01); *A61F 13/15601* (2013.01);
(Continued)

(58) Field of Classification Search
CPC .......... A61F 13/15739; A61F 13/15593; A61F 13/15804; A61F 13/49012; A61F 13/496;
(Continued)

(56) References Cited

U.S. PATENT DOCUMENTS 3,860,003 A    1/1975  Buell
4,610,678 A    9/1986  Weisman et al.
(Continued)

FOREIGN PATENT DOCUMENTS

EP    0846456 A1    6/1998
JP    2002345883 A   12/2002
(Continued)

OTHER PUBLICATIONS

PCT International Search Report, dated Feb. 26, 2018, 14 pages.

*Primary Examiner* — Tatyana Zalukaeva
*Assistant Examiner* — Meagan Ngo
(74) *Attorney, Agent, or Firm* — Charles R. Matson

(57) ABSTRACT

The present disclosure relates to methods for sealing absorbent cores of disposable diaper pants during the assembly process. The diaper pants may include a chassis connected with a ring-like elastic belt. Aspects of the assembly methods involve bonding a continuous length of absorbent cores between a continuous topsheet substrate and a continuous backsheet substrate advancing in a machine direction. The combined continuous topsheet substrate, continuous backsheet substrate, and continuous length of absorbent cores are then cut along a cross direction to create discrete chassis, wherein the topsheet, the backsheet, and the absorbent core of each chassis have equal longitudinal lengths. The discrete chassis are then deposited onto a first continuous elastic laminate and a second continuous elastic laminate. Opposing end regions of the absorbent cores may then be sealed by positioning a sealing layer across the topsheets of the chassis.

20 Claims, 29 Drawing Sheets

(51) Int. Cl.
*A61F 13/49* (2006.01)
*B29C 65/08* (2006.01)
*B29C 65/00* (2006.01)
*B29C 65/48* (2006.01)
*B29L 31/48* (2006.01)
*B29K 101/12* (2006.01)
*B29K 105/00* (2006.01)

(52) U.S. Cl.
CPC .. *A61F 13/15747* (2013.01); *A61F 13/15804* (2013.01); *A61F 13/496* (2013.01); *A61F 13/49012* (2013.01); *B29C 65/08* (2013.01); *B29C 65/4815* (2013.01); *B29C 66/4332* (2013.01); *A61F 2013/49092* (2013.01); *B29K 2101/12* (2013.01); *B29K 2105/251* (2013.01); *B29K 2105/256* (2013.01); *B29K 2995/0068* (2013.01); *B29L 2031/4878* (2013.01)

(58) Field of Classification Search
CPC .......... A61F 13/15747; A61F 13/15601; A61F 2013/49092; A61F 13/4906; A61F 13/49061; A61F 13/15585; A61F 13/15634; A61F 13/15666; A61F 13/15642; A61F 13/15723; A61F 13/1565; A61F 13/15577; A61F 13/19061; B29C 65/4815; B29C 66/4332; B29C 65/08; B29K 2105/251; B29K 2105/256; B29K 2101/12; B29K 2995/0068; B29L 2031/4878
USPC .................. 156/160, 163, 164, 229, 264
See application file for complete search history.

(56) References Cited

U.S. PATENT DOCUMENTS

| | | | |
|---|---|---|---|
| 4,673,402 A | 6/1987 | Weisman et al. | |
| 4,695,278 A | 9/1987 | Lawson | |
| 4,704,115 A | 11/1987 | Buell | |
| 4,795,454 A | 1/1989 | Dragoo | |
| 4,834,735 A | 5/1989 | Alemany et al. | |
| 4,888,231 A | 12/1989 | Angstadt | |
| 4,909,803 A | 3/1990 | Aziz et al. | |
| 5,137,537 A | 8/1992 | Herron et al. | |
| 5,260,345 A | 11/1993 | DesMarais et al. | |
| 5,387,207 A | 2/1995 | Dryer et al. | |
| 5,397,316 A | 3/1995 | LaVon et al. | |
| 5,562,646 A | 10/1996 | Goldman et al. | |
| 5,599,335 A | 2/1997 | Goldman et al. | |
| 5,628,097 A | 5/1997 | Benson et al. | |
| 5,669,894 A | 9/1997 | Goldman et al. | |
| 5,916,661 A | 6/1999 | Benson et al. | |
| 6,107,539 A | 8/2000 | Palumbo et al. | |
| 6,545,197 B1 | 4/2003 | Muller et al. | |
| 6,790,798 B1 | 9/2004 | Suzuki et al. | |
| 7,569,039 B2 | 8/2009 | Matsuda et al. | |
| 8,568,566 B2 | 10/2013 | Jackels et al. | |
| 8,603,277 B2 | 12/2013 | Paldey et al. | |
| 2004/0097895 A1 | 5/2004 | Busam et al. | |
| 2004/0158212 A1 | 8/2004 | Ponomarenko et al. | |
| 2005/0107764 A1 | 5/2005 | Matsuda et al. | |
| 2006/0244166 A1* | 11/2006 | Wada | A61F 13/49014 264/37.1 |
| 2009/0312730 A1 | 12/2009 | LaVon et al. | |
| 2010/0051166 A1* | 3/2010 | Hundorf | A61F 13/15658 156/62.8 |
| 2010/0076394 A1* | 3/2010 | Hayase | B29C 66/1122 604/385.29 |
| 2012/0061015 A1 | 3/2012 | LaVon et al. | |
| 2012/0061016 A1 | 3/2012 | LaVon et al. | |
| 2012/0071852 A1* | 3/2012 | Tsang | A61F 13/15609 604/385.25 |
| 2012/0143162 A1* | 6/2012 | Mukai | A61F 13/49001 604/385.3 |
| 2012/0316046 A1 | 12/2012 | Jackels et al. | |
| 2013/0255861 A1 | 10/2013 | Schneider | |
| 2013/0255862 A1* | 10/2013 | Schneider | A61F 13/15593 156/161 |
| 2013/0255863 A1 | 10/2013 | LaVon et al. | |
| 2013/0255864 A1 | 10/2013 | Schneider et al. | |
| 2013/0255865 A1 | 10/2013 | Brown et al. | |
| 2013/0270065 A1 | 10/2013 | Papsdorf et al. | |
| 2013/0270066 A1 | 10/2013 | Papsdorf et al. | |
| 2013/0270067 A1 | 10/2013 | Papsdorf et al. | |
| 2014/0000795 A1* | 1/2014 | Hamilton | A61F 13/15699 156/164 |
| 2014/0163501 A1* | 6/2014 | Ehrnsperger | A61F 13/4753 604/366 |
| 2014/0163504 A1 | 6/2014 | Bianchi et al. | |
| 2015/0290047 A1 | 10/2015 | Royce et al. | |
| 2016/0302977 A1 | 10/2016 | Zink, II et al. | |
| 2016/0331600 A1* | 11/2016 | Polidori | B29C 66/8432 |
| 2017/0049638 A1* | 2/2017 | Mori | A61F 13/49011 |
| 2018/0193206 A1* | 7/2018 | Takino | A61F 13/49019 |

FOREIGN PATENT DOCUMENTS

| | | |
|---|---|---|
| JP | 2014004115 A | 1/2014 |
| JP | 2016059608 A | 4/2016 |

* cited by examiner

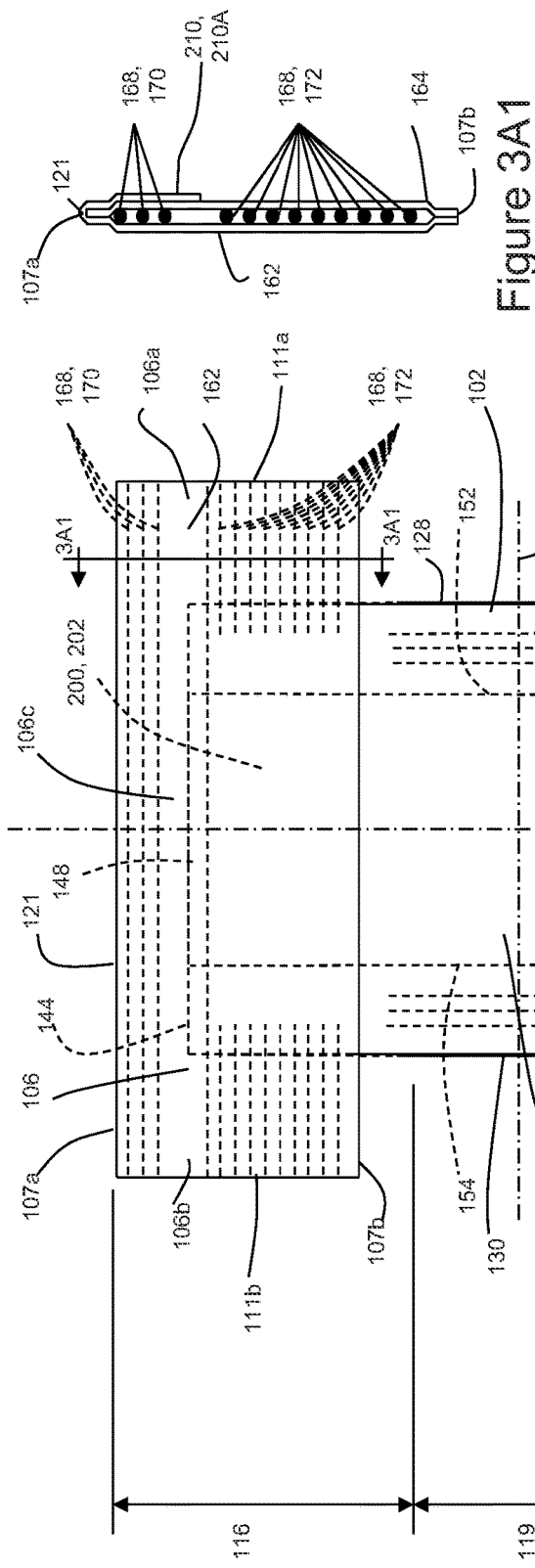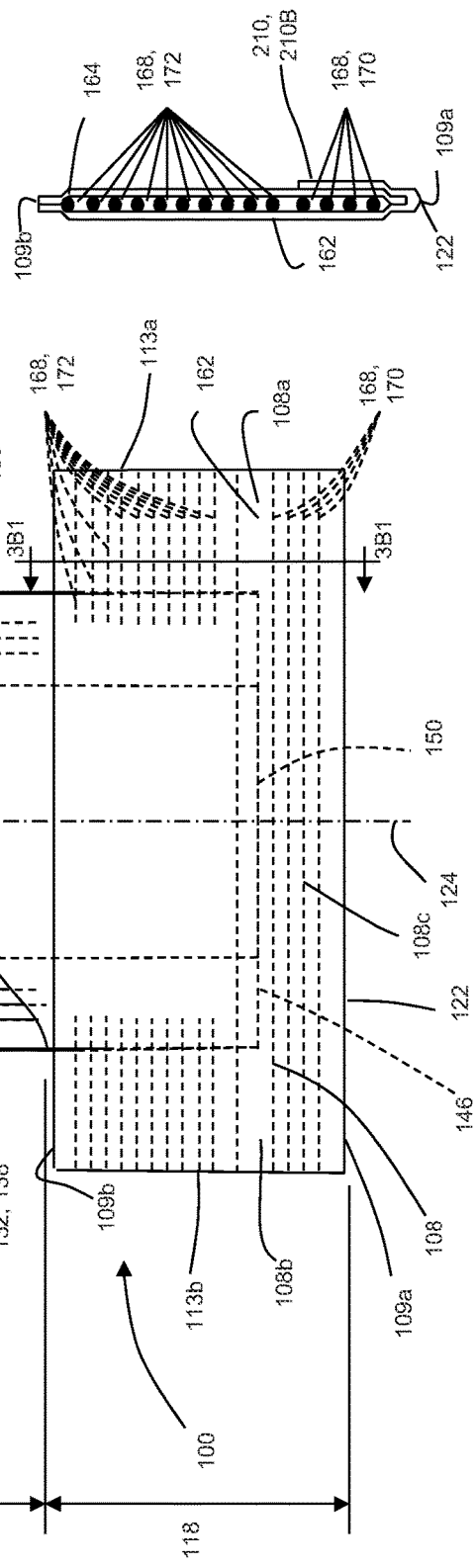

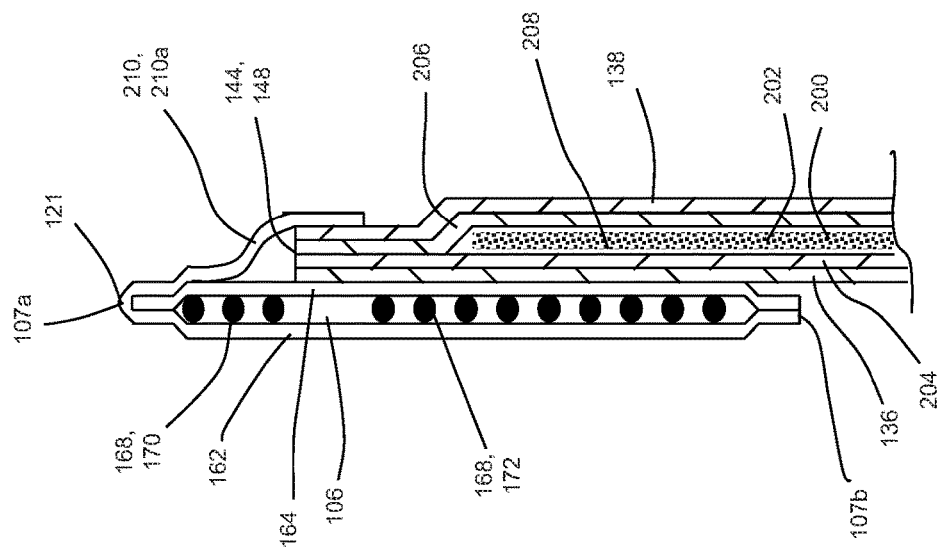
Figure 3A2
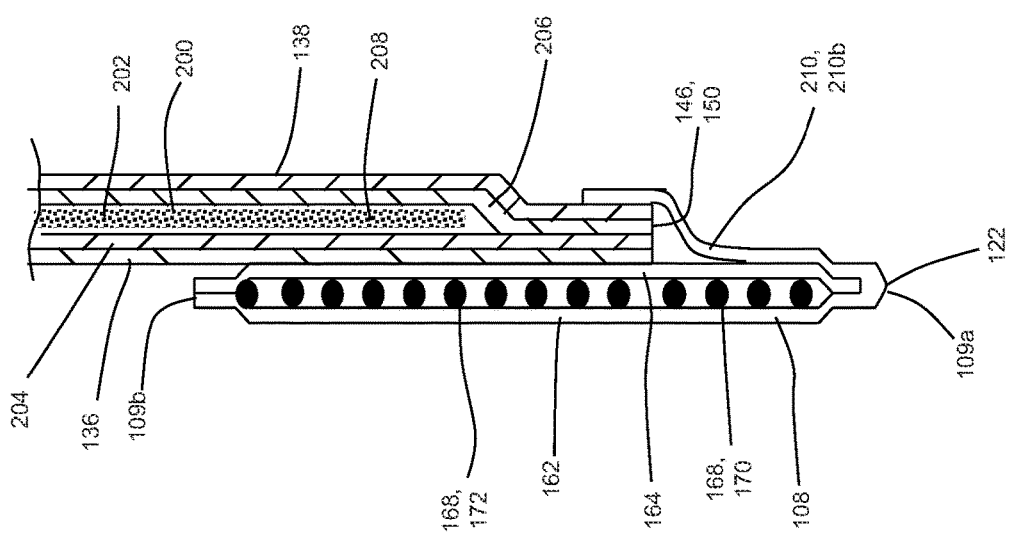
Figure 3B2

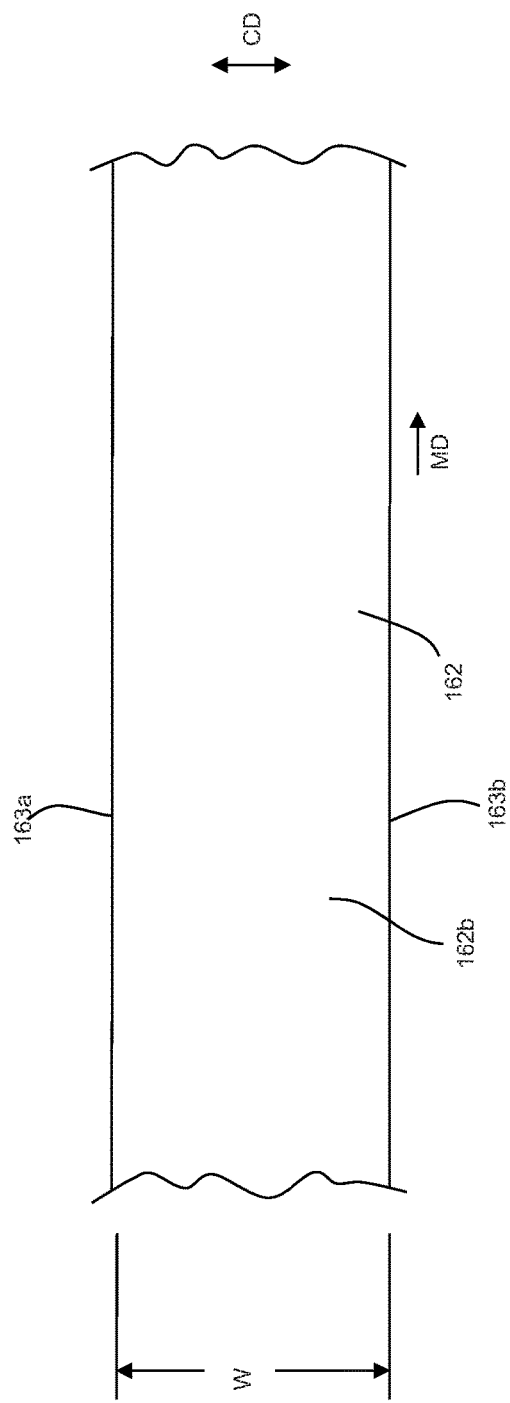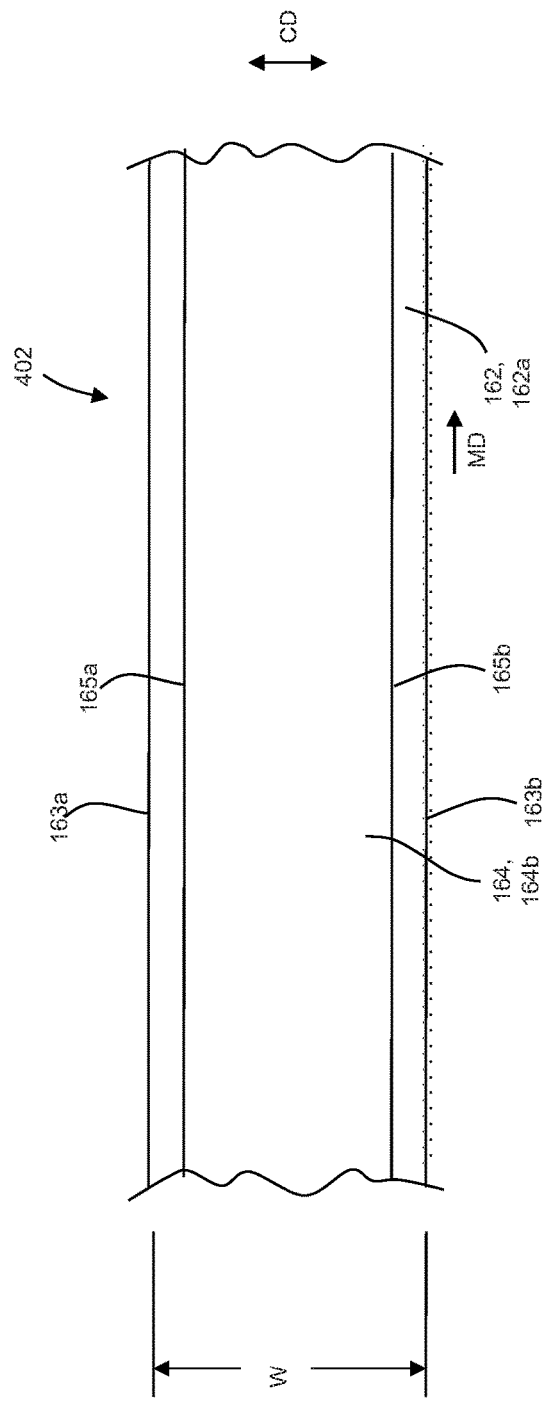

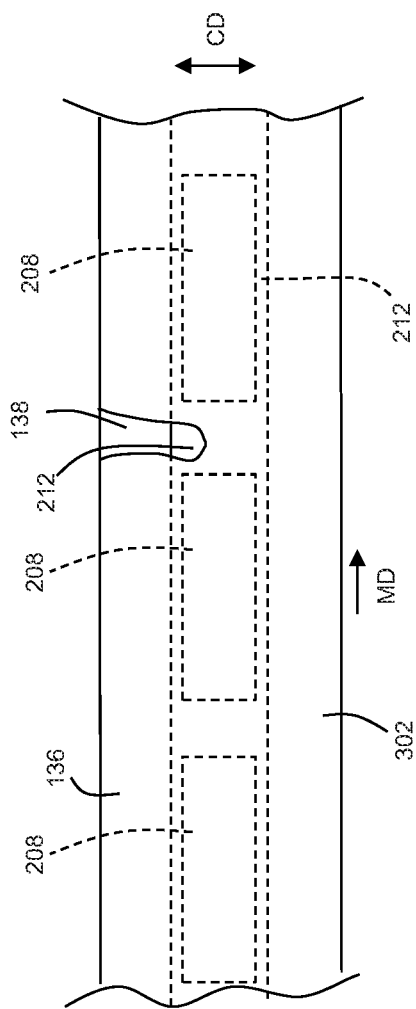
Figure 5C
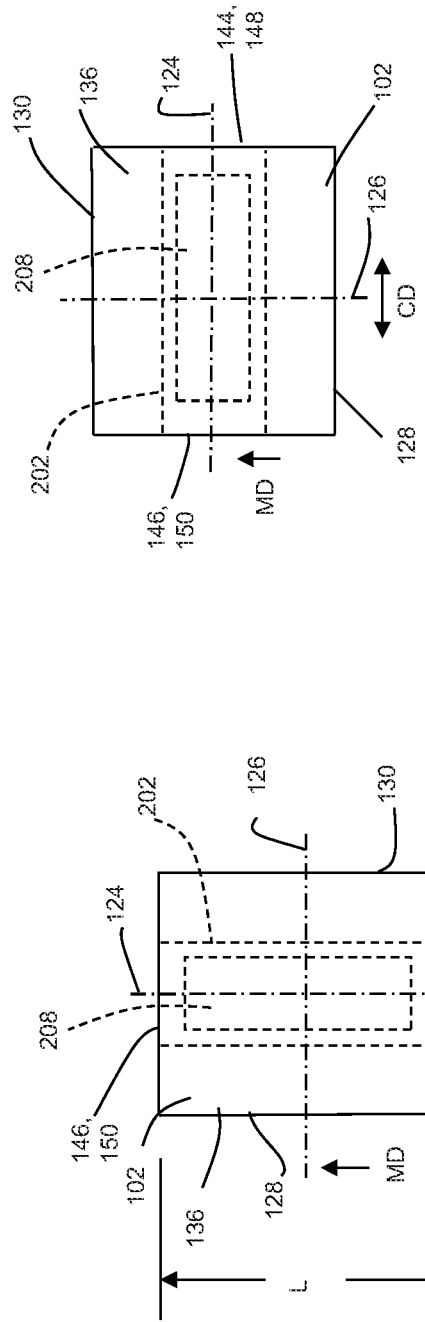
Figure 5D2
Figure 5D1

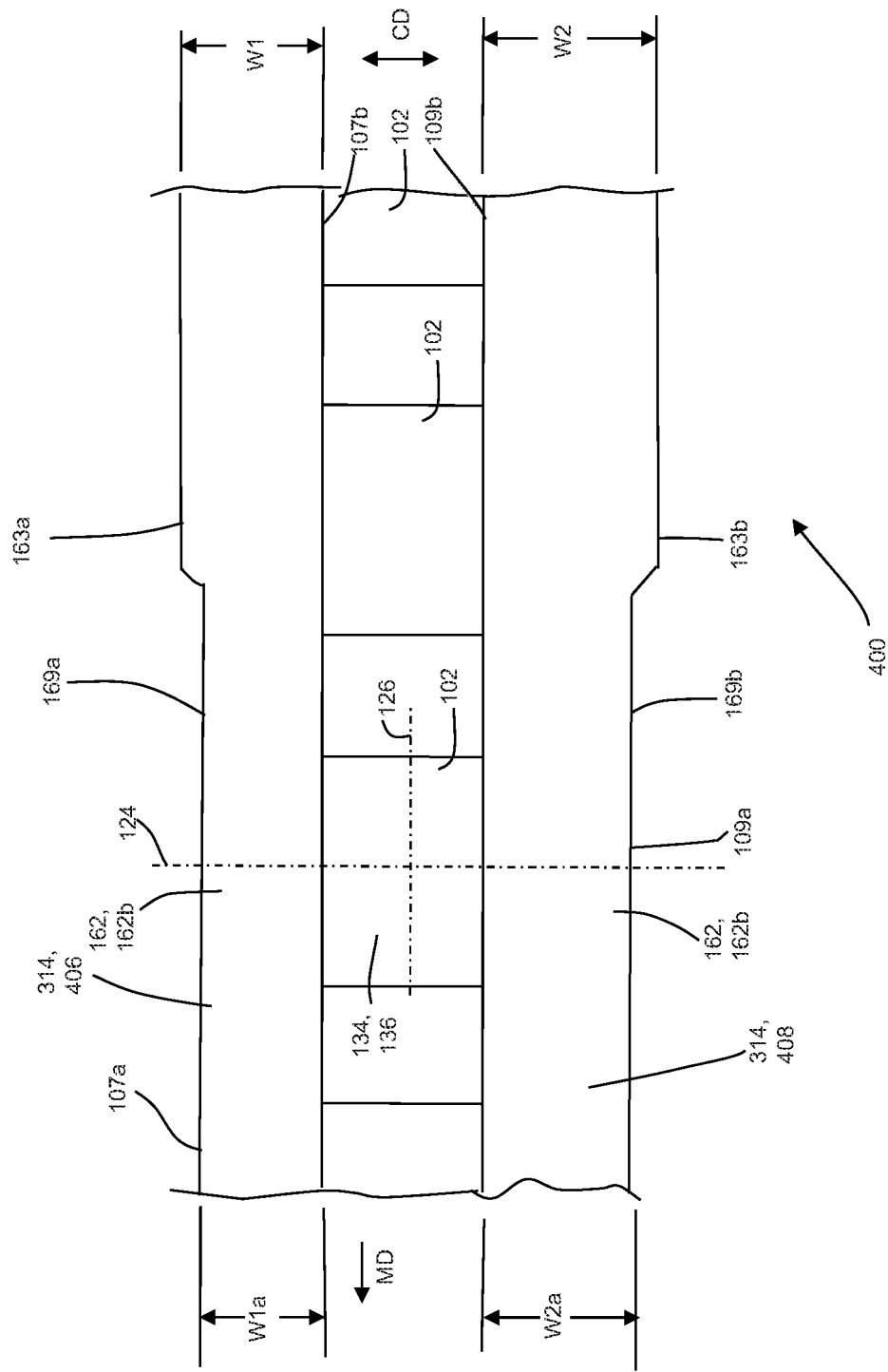
Figure 5E1

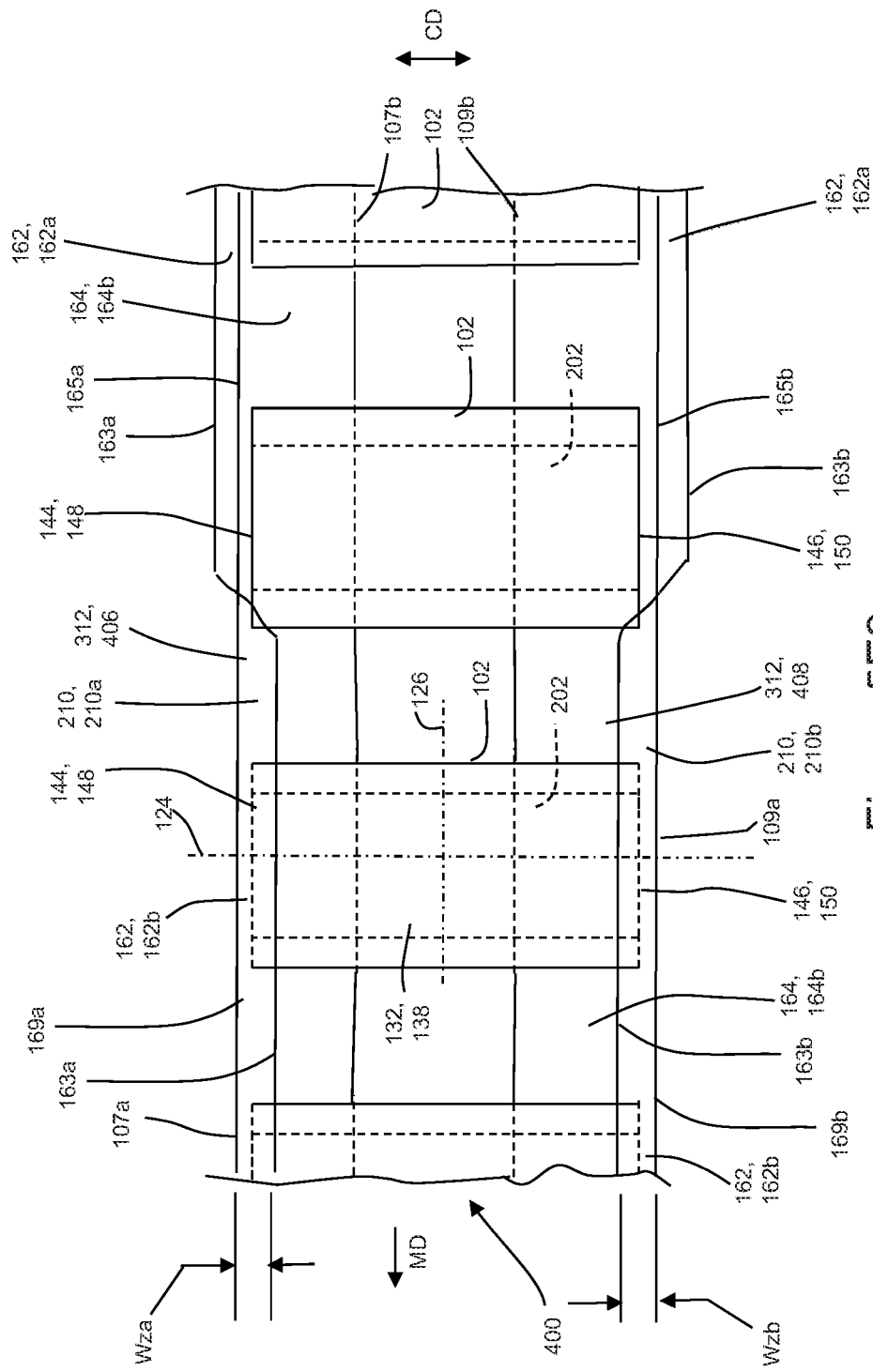
Figure 5E2

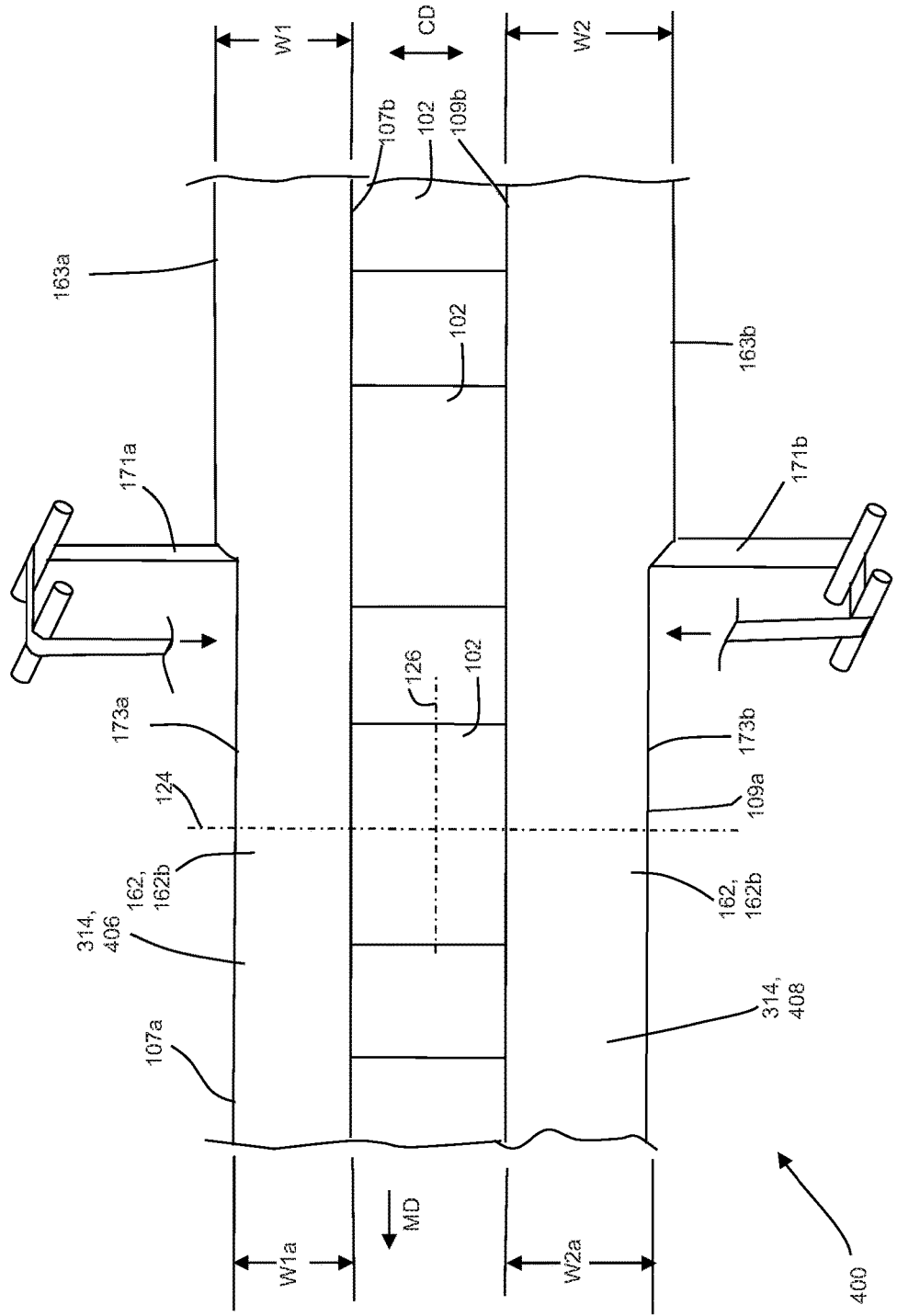
Figure 5E1A

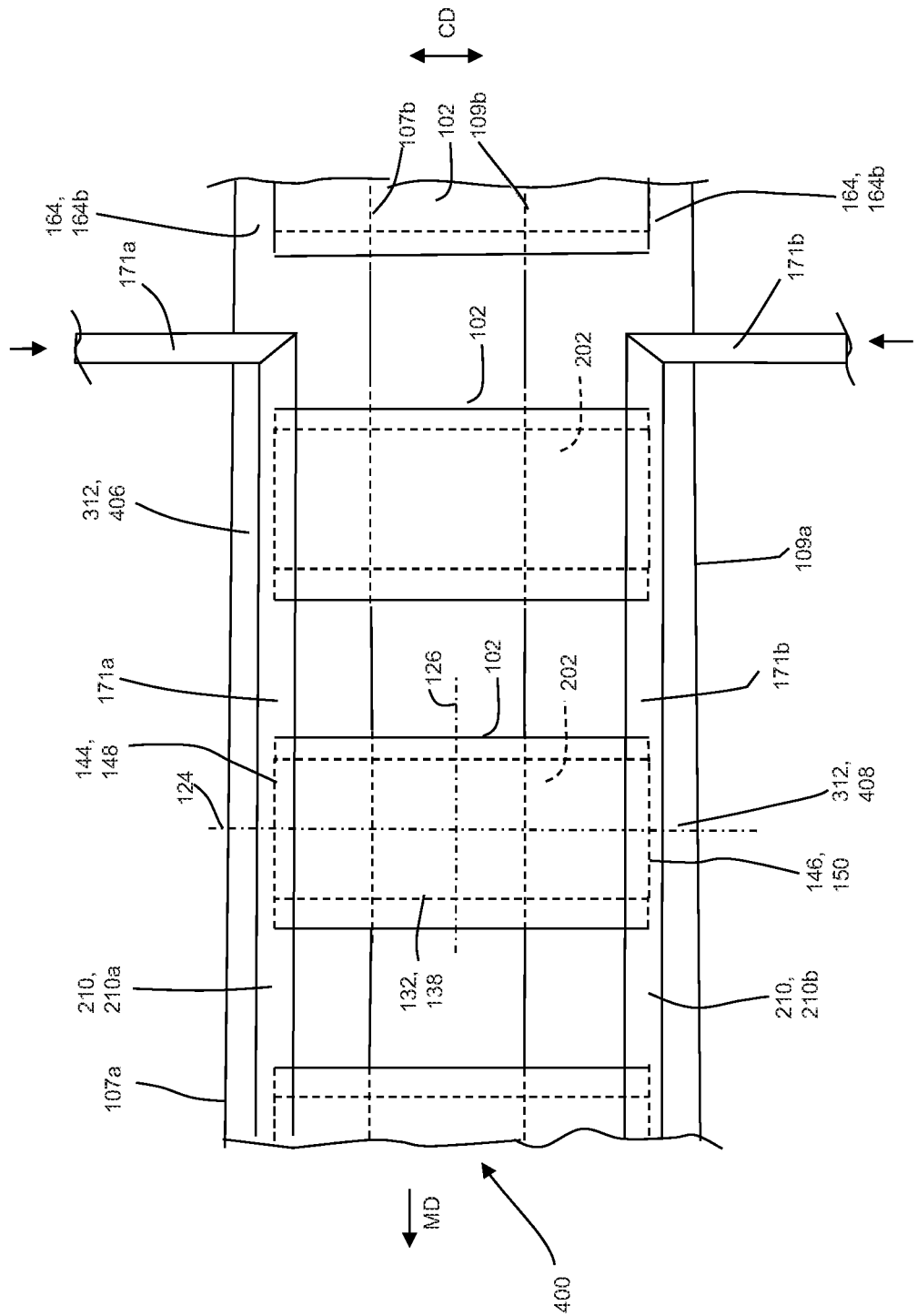
Figure 5E2A

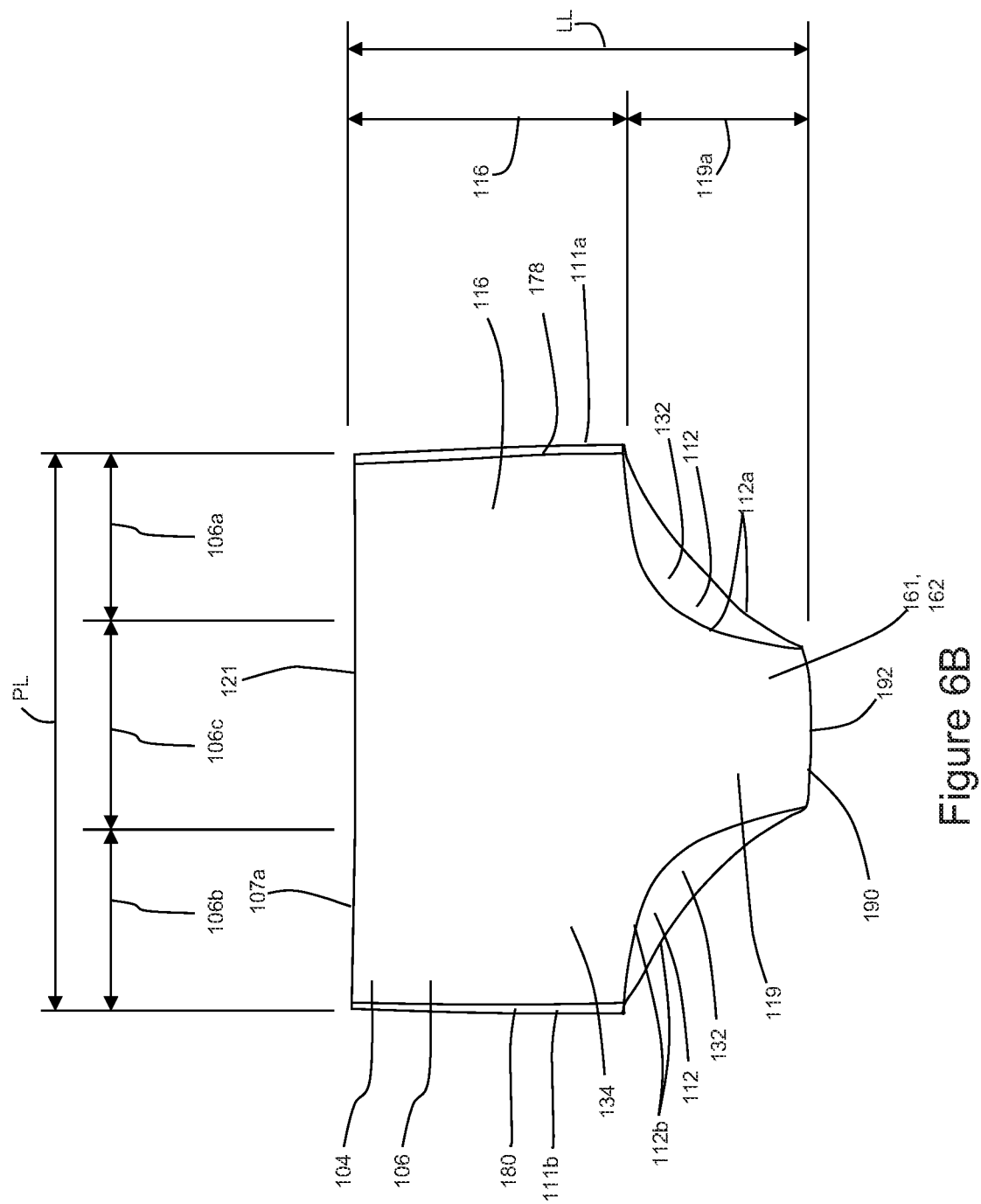

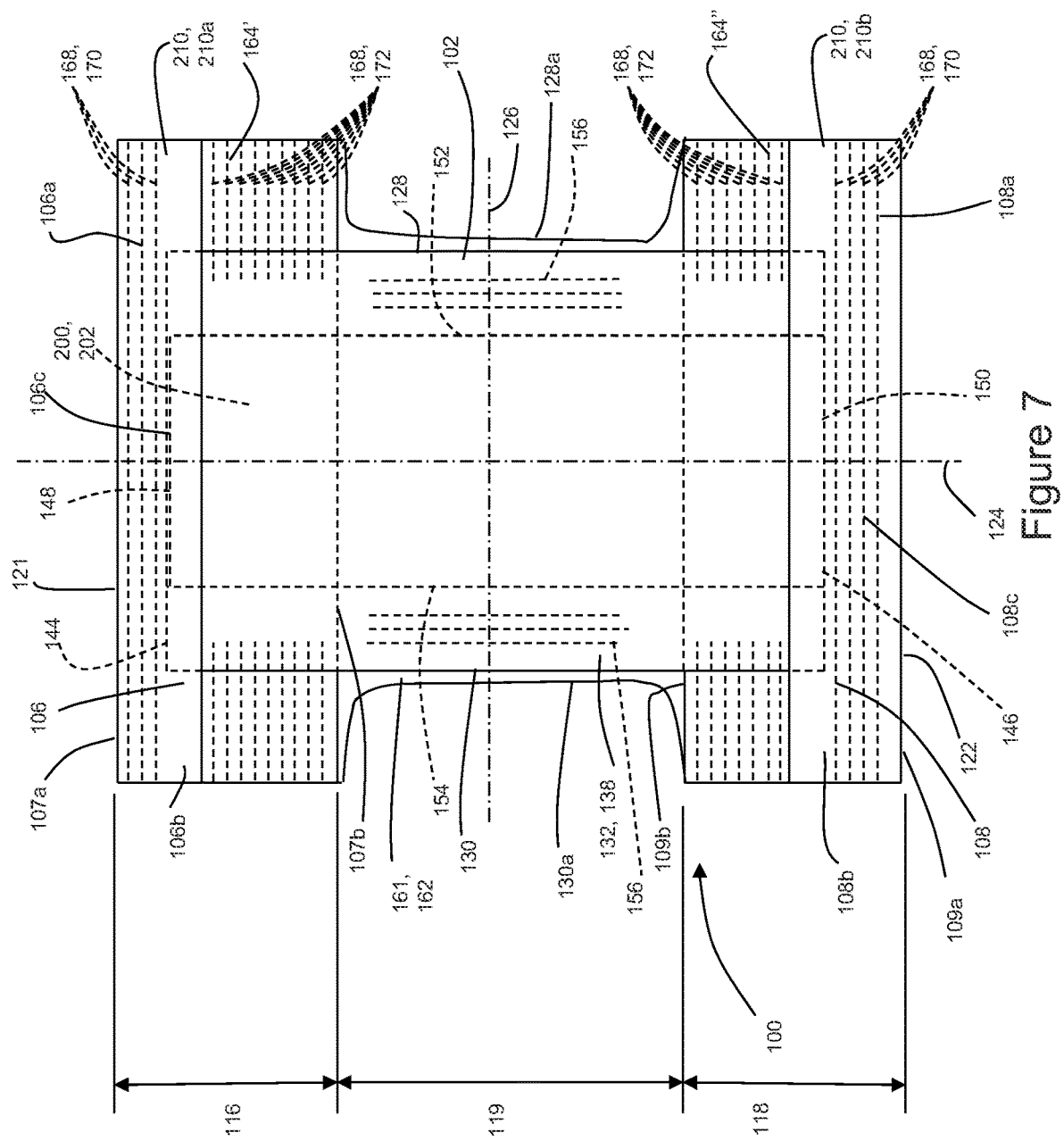

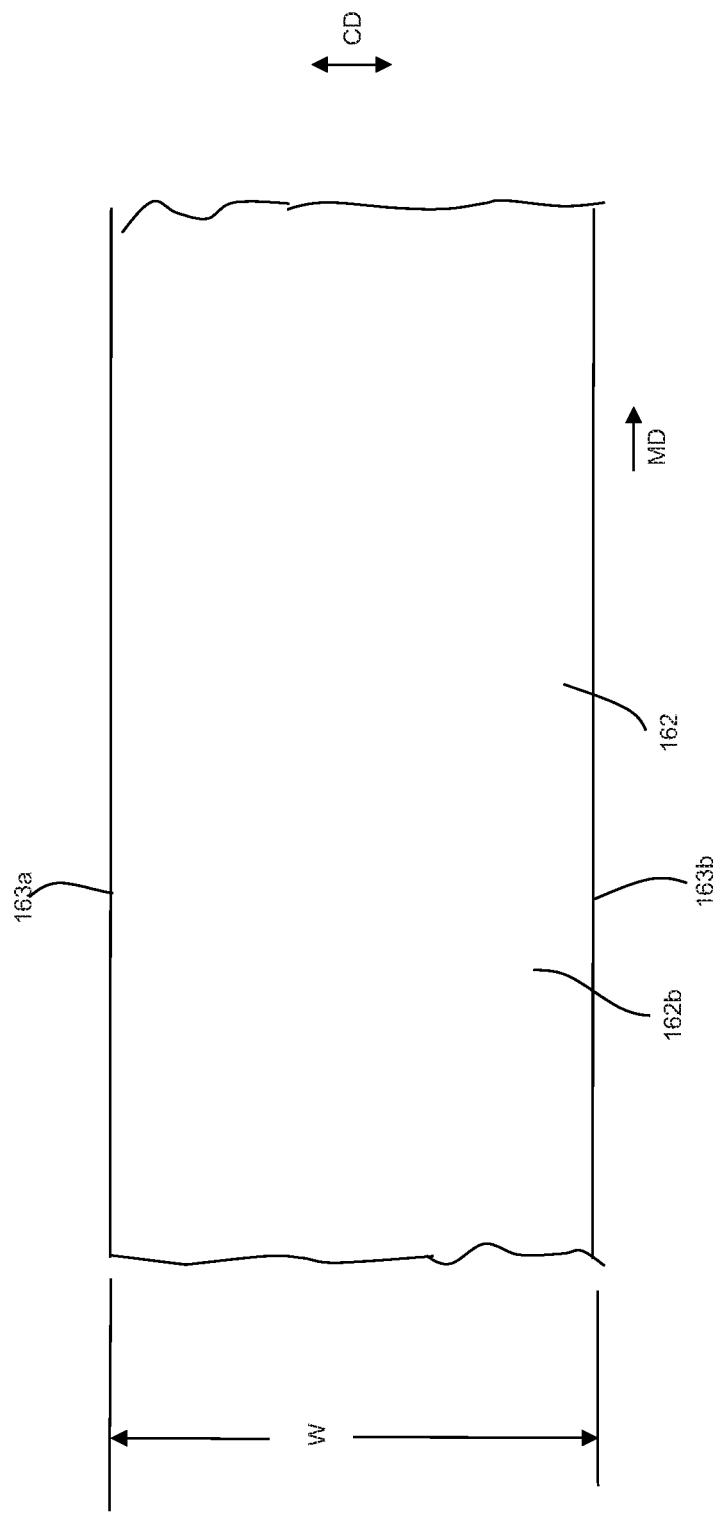

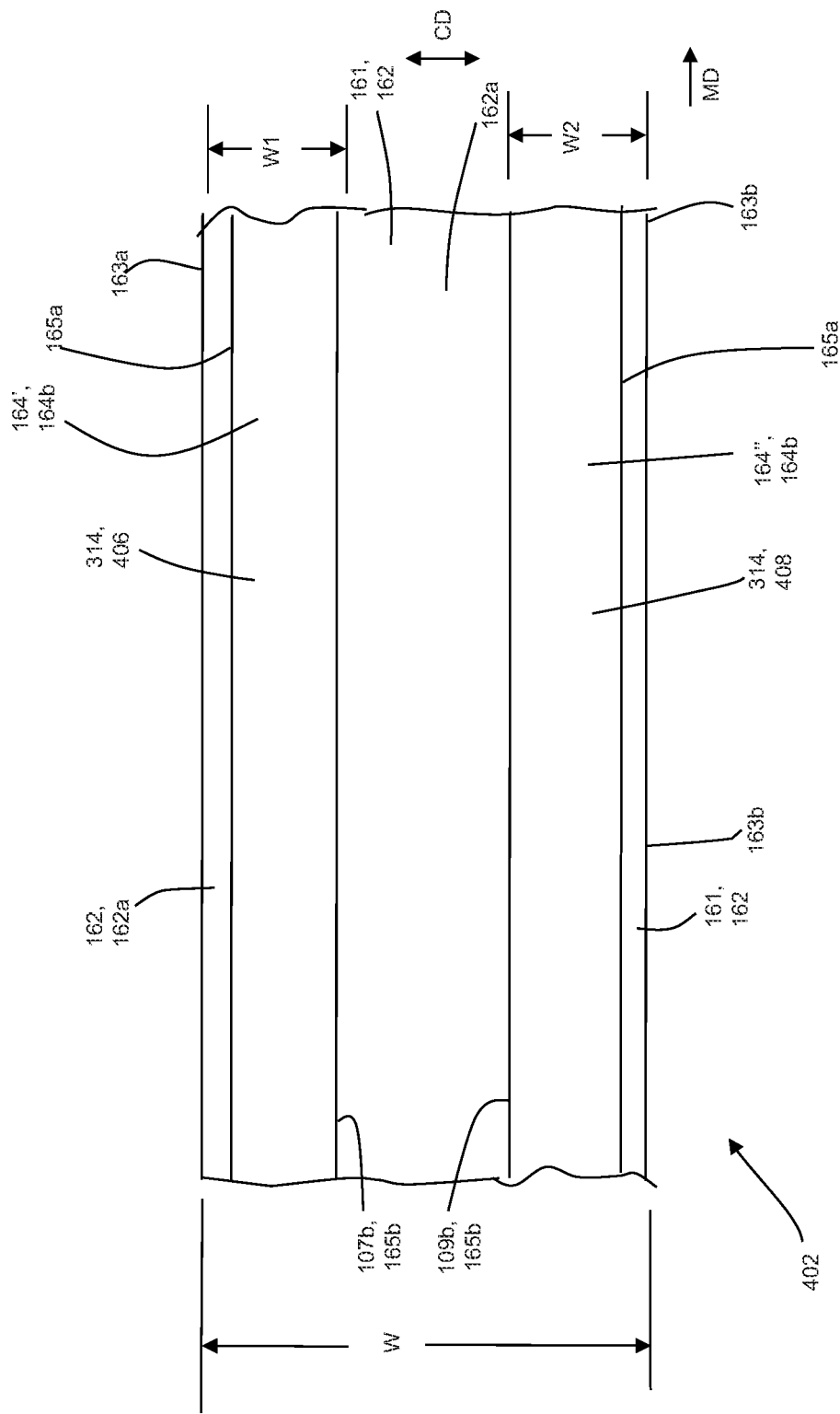
Figure 9A2

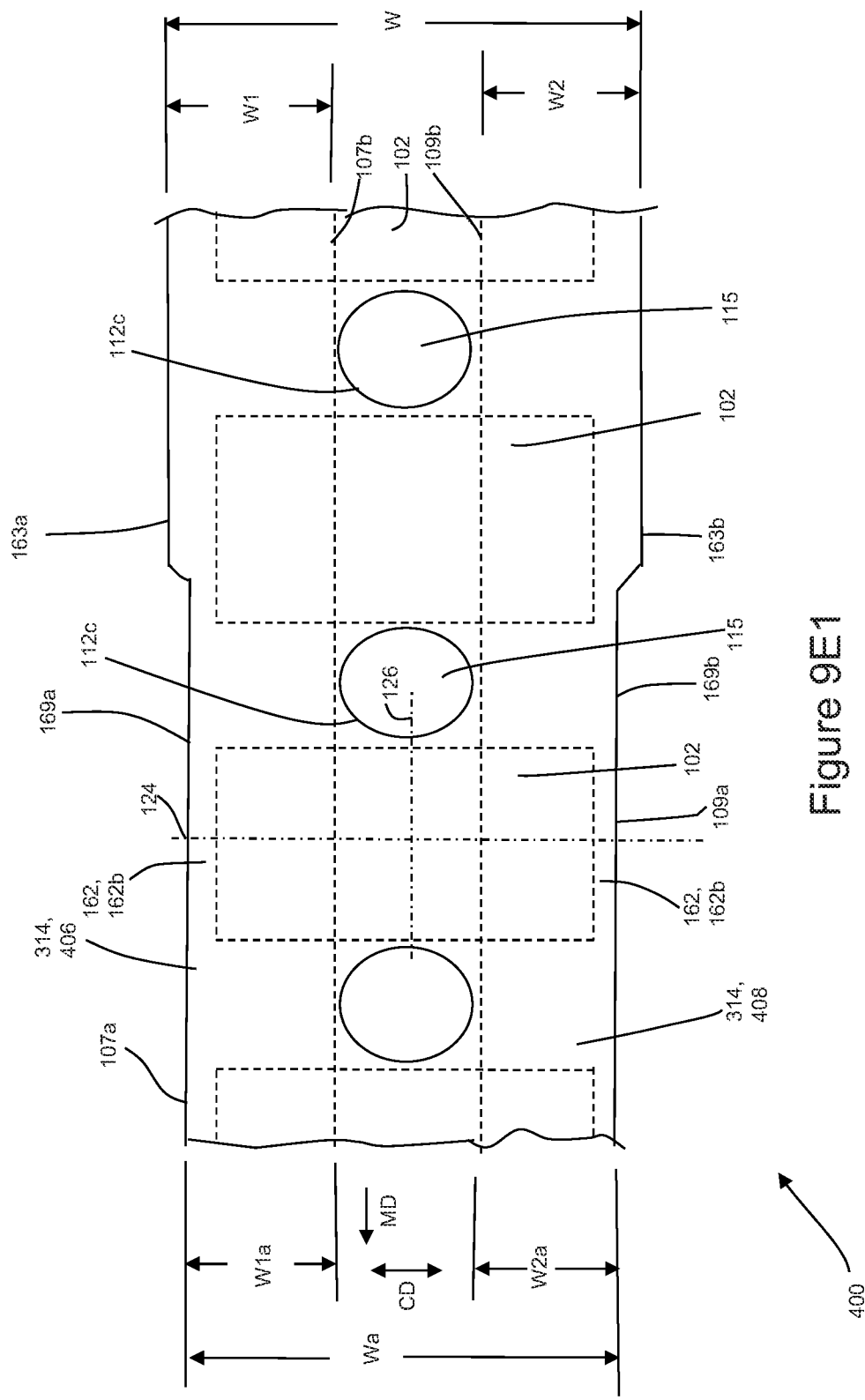
Figure 9E1

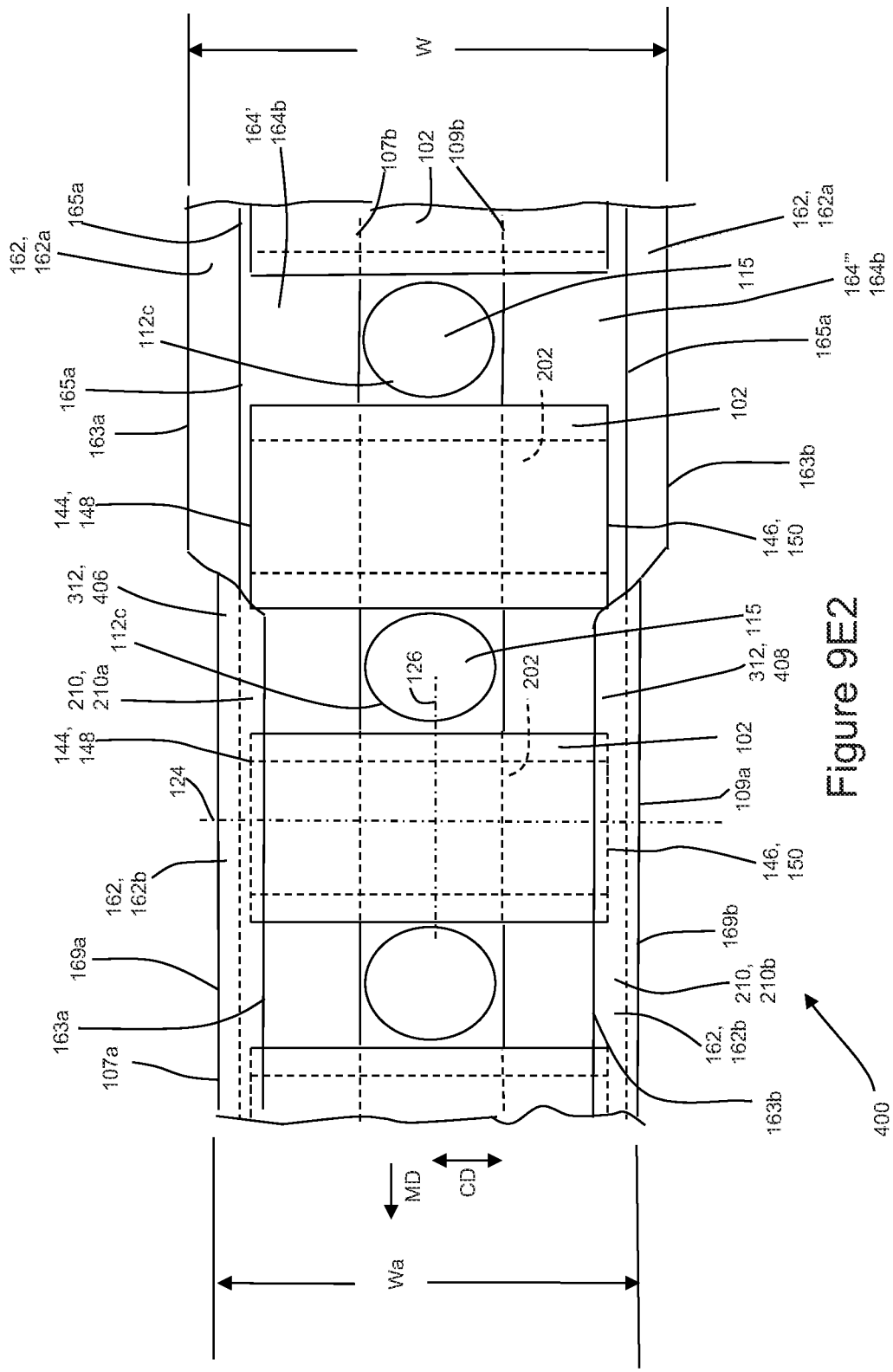
Figure 9E2

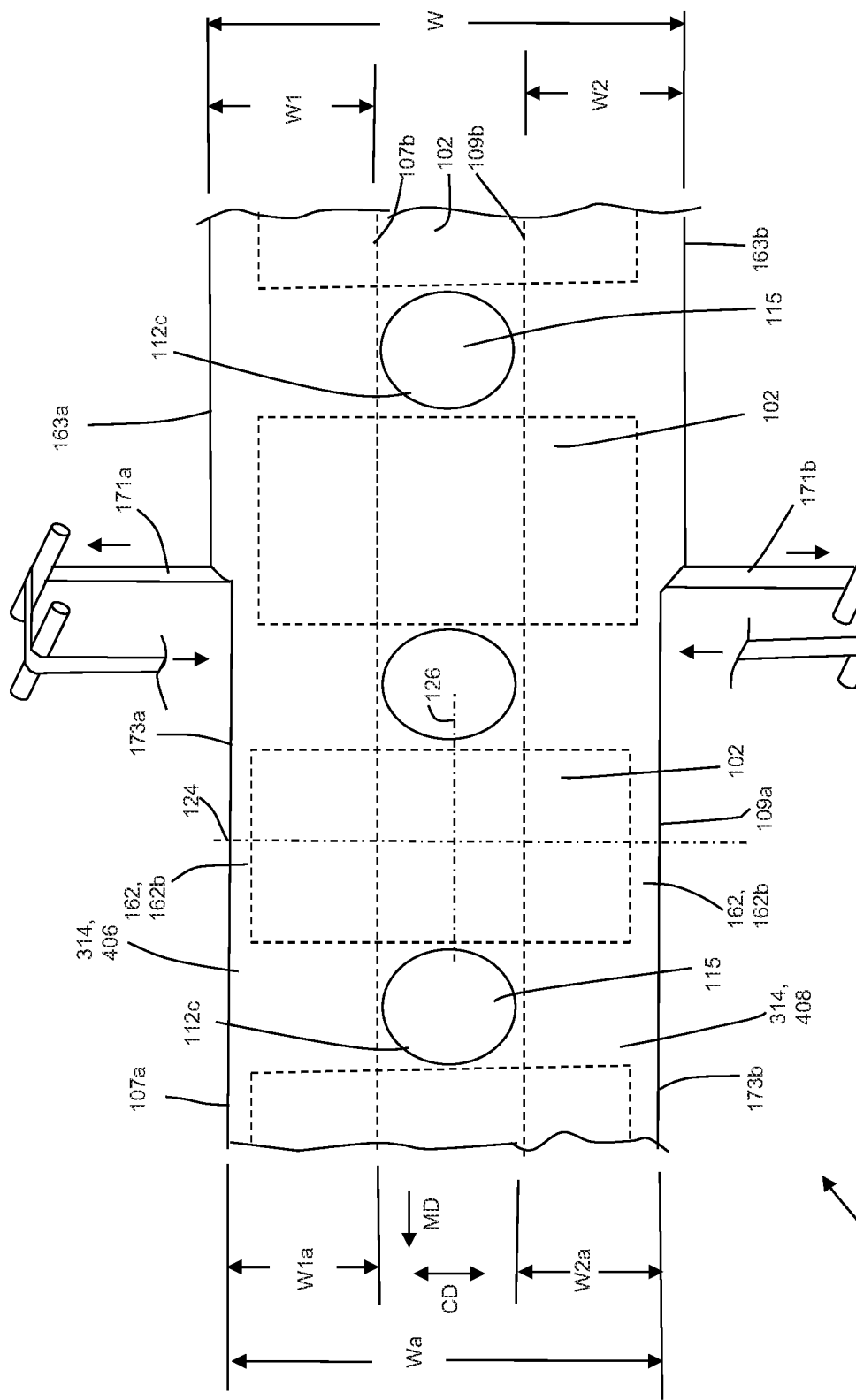

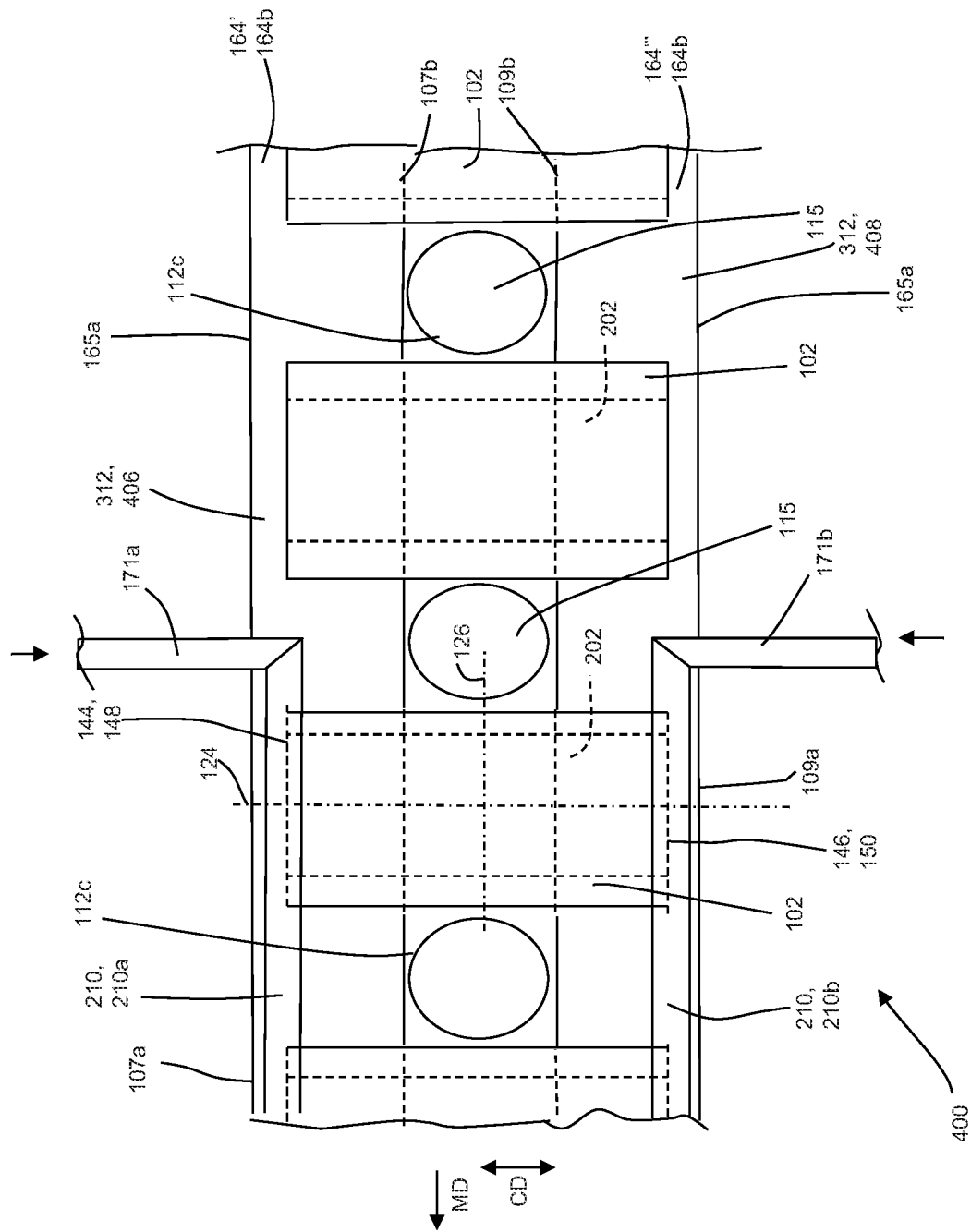
Figure 9E2A

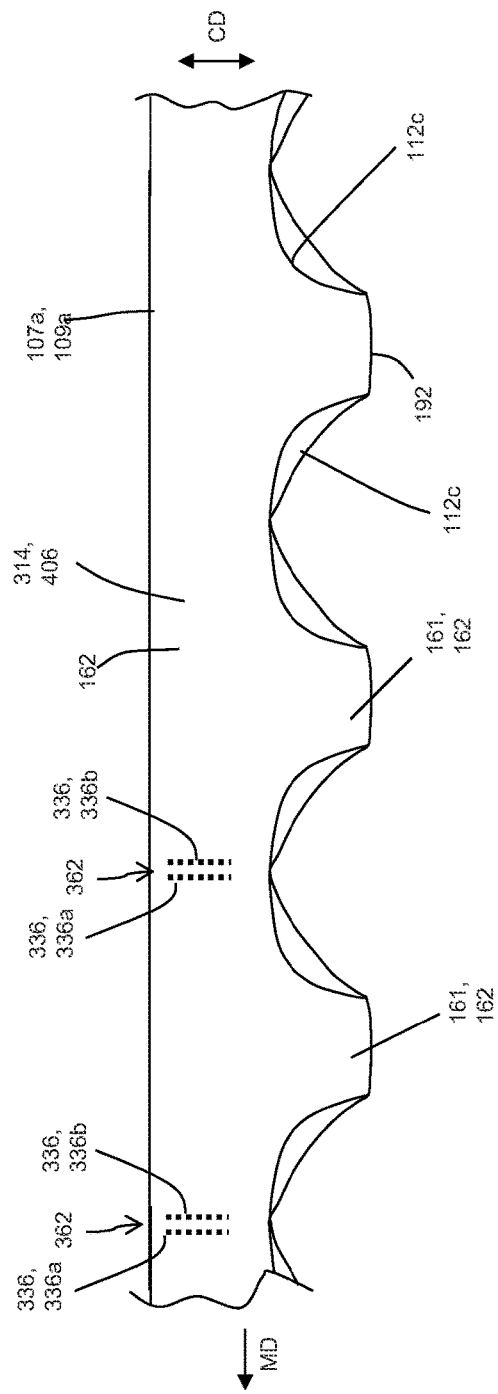
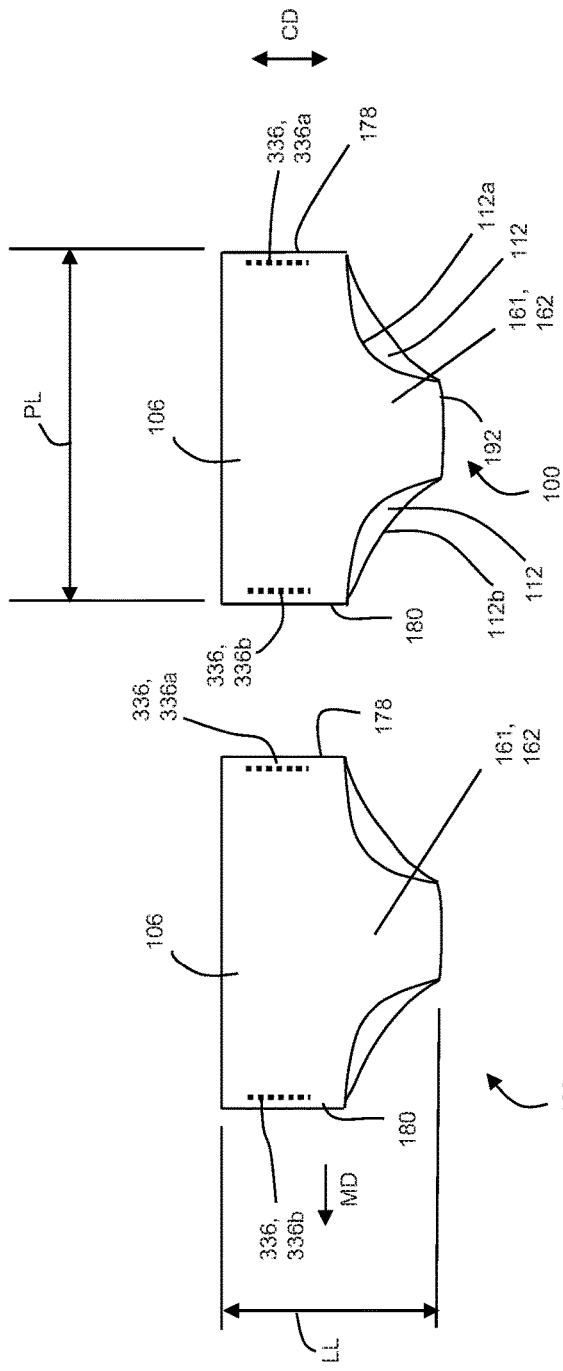

METHODS FOR SEALING ABSORBENT CORES ON ABSORBENT ARTICLES

FIELD OF THE INVENTION

The present disclosure relates to methods for manufacturing absorbent articles, and more particularly, to sealing absorbent cores of absorbent articles during the assembly process.

BACKGROUND OF THE INVENTION

Along an assembly line, various types of articles, such as for example, diapers and other absorbent articles, may be assembled by adding components to and/or otherwise modifying an advancing, continuous web of material. For example, in some processes, advancing webs of material are combined with other advancing webs of material. In other examples, individual components created from advancing webs of material are combined with advancing webs of material, which in turn, are then combined with other advancing webs of material. In some cases, individual components created from an advancing web or webs are combined with other individual components created from other advancing webs. Webs of material and component parts used to manufacture diapers may include: backsheets, topsheets, leg cuffs, waist bands, acquisition layers, absorbent core components, front and/or back ears, fastening components, and various types of elastic webs and components such as leg elastics, barrier leg cuff elastics, stretch side panels, and waist elastics. Once the desired component parts are assembled, the advancing web(s) and component parts are subjected to a final knife cut to separate the web(s) into discrete diapers or other absorbent articles.

In some configurations, absorbent articles may include absorbent structures positioned between topsheets and backsheets. Absorbent structures may be constructed in various ways in an attempt to improve wearer fit and comfort and/or the manner in which absorbent structures absorb and/or transport liquid discharged onto and through a topsheet. For example, the absorbent structures may be constructed in various shapes and/or with varying amounts of absorbent material arranged along a width and/or a length. The absorbent structures may also include acquisition layers and absorbent cores, wherein the acquisition layers may be positioned between the absorbent cores and topsheets. As such, the topsheets, backsheets, and absorbent structures of such absorbent articles may function to absorb and/or contain the discharged materials and also to isolate bodily exudates from the wearer's skin and from the wearer's garments and bed clothing.

It is often desirable to construct the absorbent cores such that the absorbent material remains isolated from the wearer of an absorbent article during use. Thus, in some manufacturing configurations, absorbent cores may be assembled by placing absorbent material between two opposing sheets of material to create a continuous length of absorbent cores. As such, the opposing sheets may be bonded together during assembly to help seal the absorbent material inside the absorbent core. Discrete absorbent cores may then be cut from the continuous length of absorbent cores, and the discrete absorbent cores are bonded between continuous lengths of topsheet and backsheet webs. Next, discrete chassis may then be cut from the continuous lengths of topsheet and backsheet webs. In addition, the discrete chassis may be formed such that backsheet and topsheet define widths and lengths that are greater than the width and length of the absorbent core. As such, the backsheet and topsheet may be bonded together in the area surrounding the periphery of the absorbent core to provide an additional means for sealing the absorbent core to prevent absorbent material from escaping the absorbent core during use and potentially contacting the wearer of the absorbent article.

Although the previously mentioned manufacturing operations may provide a relatively reliable means to ensure that absorbent cores remained sealed during use, such manufacturing operations may have some drawbacks. For example, creating discrete absorbent cores that are bonded between advancing topsheet and backsheet webs may involve complex process transformations. For example, after cutting the individual absorbent cores from the continuous length of absorbent cores, each individual core may have to be precisely placed in desired positions on the advancing topsheet or backsheet webs. In some manufacturing configurations, the speeds of the individual absorbent cores will need to be increased or decreased before placement on the topsheet or backsheet webs. In some instances, adhesives will also need to be applied in discrete zones on the advancing webs, requiring relatively frequent on/off cycling of adhesive applicators. To help ensure quality production, the individual absorbent core placement may need to be closely monitored and controlled with relatively high speed sensor and associated controller technologies. As such, the machinery required to precisely cut, place, control, and/or bond the individual cores to advancing webs may add complexities and expense to a manufacturing line while at the same time reducing reliability. In addition, the aforementioned challenges may be exacerbated in absorbent article assembly processes operating at relatively high speed production rates and/or configured to assemble relatively small sized absorbent articles.

Consequently, it would be beneficial to provide assembly methods and apparatuses that are configured to help ensure that absorbent cores are sealed without the need to create discrete absorbent cores that are subsequently placed between advancing continuous topsheet and backsheet webs.

SUMMARY OF THE INVENTION

In one form, a method for assembling disposable diaper pants comprises the steps of: advancing a first continuous elastic laminate in a machine direction, the first continuous elastic laminate comprising an outer substrate comprising a first surface and an opposing second surface, an inner substrate comprising a first surface and an opposing second surface, and elastic material bonded between the first surfaces of the inner and outer substrates; advancing a second continuous elastic laminate in the machine direction; providing a continuous length of absorbent cores; bonding the continuous length of absorbent cores between a continuous topsheet substrate and a continuous backsheet substrate; cutting the continuous topsheet substrate, the continuous backsheet substrate, and the continuous length of absorbent cores together along a cross direction to create discrete chassis, each chassis comprising a topsheet, a backsheet, and an absorbent core disposed between the topsheet and the backsheet, wherein the topsheet, the backsheet, and the absorbent core each comprise a first end region and an opposing second end region separated from each other by a central region, and comprising a longitudinal axis and a lateral axis, wherein the longitudinal axis is parallel with the machine direction, wherein the topsheet, the backsheet, and the absorbent core have equal longitudinal lengths, L;

depositing the discrete chassis spaced apart from each other along the machine direction onto the first continuous elastic laminate and the second continuous elastic laminate; and sealing the first end regions of the absorbent cores by folding a portion of the first continuous elastic laminate into a facing relationship with the topsheets of each chassis, wherein first end regions of each topsheet, backsheet, and absorbent core are positioned between the folded portion of the first continuous elastic laminate and the second surface of the inner substrate.

In another form, a method for assembling disposable diaper pants comprises the steps of: advancing a continuous elastic laminate in a machine direction, the continuous elastic laminate comprising an outer substrate comprising a first surface and an opposing second surface, an inner substrate comprising a first surface and an opposing second surface, and elastic material bonded between the first surfaces of the inner and outer substrates; providing a continuous length of absorbent cores; bonding the continuous length of absorbent cores between a continuous topsheet substrate and a continuous backsheet substrate to form a continuous length of absorbent chassis; cutting the continuous topsheet substrate, the continuous backsheet substrate, and the continuous length of absorbent cores together along a cross direction to create discrete chassis, each chassis comprising a topsheet, a backsheet, and an absorbent core disposed between the topsheet and the backsheet, the topsheet, backsheet, and absorbent core each comprising a first end region and an opposing second end region separated from each other by a central region, and comprising a longitudinal axis and a lateral axis, wherein the longitudinal axis is parallel with the machine direction, wherein the topsheet, the backsheet, and the absorbent core have equal longitudinal lengths, L; depositing the discrete chassis spaced apart from each other along the machine direction onto the continuous elastic laminate; providing a sealing layer extending in the machine direction; sealing the first end regions of the absorbent cores by bonding the sealing layer with the second surface of the inner substrate and the topsheets of each chassis, wherein first end regions of each topsheet, backsheet, and absorbent core are positioned between the sealing layer and the second surface of the inner substrate.

In yet another form, an absorbent article comprises: a first elastic belt comprising a first end region and a laterally opposing second region separated from each other by a central region; a second elastic belt comprising a first end region and a laterally opposing second region separated from each other by a central region, wherein the first end region of the first elastic belt is connected with the first end region of the second elastic belt, and wherein the second end region of the first elastic belt is connected with the second end region of the second elastic belt; a chassis comprising, a topsheet, a backsheet, and an absorbent core disposed between the topsheet and the backsheet, wherein the topsheet, the backsheet, and the absorbent core each comprise a first waist region and an opposing second waist region longitudinally separated from each other by a crotch region, and wherein the topsheet, the backsheet, and the absorbent core have equal longitudinal lengths, L, and wherein the first waist region of the backsheet is connected with the central region of the first elastic belt and the second waist region of the backsheet is connected with the central region of the second elastic belt; and a sealing layer extending laterally across the topsheet and the first elastic belt to seal the first waist region of the absorbent core, wherein first waist regions of each the topsheet, the backsheet, and the absorbent core are positioned between the sealing layer and the first elastic belt.

BRIEF DESCRIPTION OF THE DRAWINGS

FIG. 2A is a partially cut away plan view of the diaper pant shown in FIGS. 1A and 1B in a flat, uncontracted state with the portion of the diaper that faces away from a wearer oriented towards the viewer.

FIG. 3A1 is a cross-sectional view of the diaper pant of FIG. 2A taken along line 3A1-3A1.

FIG. 3B1 is a cross-sectional view of the diaper pant of FIG. 2A taken along line 3B1-3B1.

FIG. 3A2 is a cross-sectional view of the diaper pant of FIG. 2B taken along line 3A2-3A2.

FIG. 3B2 is a cross-sectional view of the diaper pant of FIG. 2B taken along line 3B2-3B2.

FIG. 5A1 is a view of a continuous length of an advancing first substrate from FIG. 4 taken along line A1-A1.

FIG. 5A2 is a view of a continuous length of an advancing elastic laminate from FIG. 4 taken along line A2-A2.

FIG. 5C is a view of a continuous length of chassis assemblies from FIGS. 4 and 8 taken along line C-C.

FIG. 5D1 is a view of a discrete chassis from FIGS. 4 and 8 taken along line D1-D1.

FIG. 5D2 is a view of a discrete chassis from FIGS. 4 and 8 taken along line D2-D2.

FIG. 5E1 is a view of multiple discrete chassis spaced from each other along the machine direction MD and connected with each other by the first and second elastic belt laminates from FIG. 4 taken along line E1-E1 and showing outer edges of the first and second elastic belt laminates being folded.

FIG. 5E2 is a view of multiple discrete chassis spaced from each other along the machine direction MD and connected with each other by the first and second elastic belt laminates from FIG. 4 taken along line E2-E2 and showing outer edges of the first and second elastic belt laminates being folded.

FIG. 5E1A is a view of multiple discrete chassis spaced from each other along the machine direction MD and connected with each other by the first and second elastic belt laminates from FIG. 4 taken along line E1-E1 and showing strips of material being removed from the first and second elastic belt laminates.

FIG. 5E2A is a view of multiple discrete chassis spaced from each other along the machine direction MD and connected with each other by the first and second elastic belt laminates and showing strips of material from FIG. 5E1A being applied as sealing layers to the first and second elastic belt laminates.

FIG. 6B is a front plan view of the diaper pant of FIG. 6A.

FIG. 7 is a partially cut away plan view of the diaper pant shown in FIGS. 6A-6C in a flat, uncontracted state.

FIG. 9A1 is a view of a continuous length of an advancing first substrate from FIG. 8 taken along line A1-A1.

FIG. 9A2 is a view of a continuous length of an advancing elastic laminate from FIG. 8 taken along line A2-A2.

FIG. 9E1 is a view of multiple discrete chassis spaced from each other along the machine direction MD and connected with each other by an outer cover and the first and second elastic belt laminates from FIG. 8 taken along line E1-E1 and showing outer edges of the outer cover being folded.

FIG. 9E2 is a view of multiple discrete chassis spaced from each other along the machine direction MD and connected with each other by an outer cover and the first and second elastic belt laminates from FIG. 8 taken along line E2-E2 and showing outer edges of the outer cover being folded.

FIG. 9E1A is a view of multiple discrete chassis spaced from each other along the machine direction MD and connected with each other by an outer cover and the first and second elastic belt laminates from FIG. 8 taken along line E1-E1 and showing strips of material being removed from the outer cover.

FIG. 9E2A is a view of multiple discrete chassis spaced from each other along the machine direction MD and connected with each other by the first and second elastic belt laminates and showing strips of material from FIG. 9E1A being applied as sealing layers to the first and second elastic belt laminates.

FIG. 9F is a view of folded multiple discrete chassis with the first and second elastic belt laminates in a facing relationship from FIG. 8 taken along line F-F.

FIG. 9G is a view of two discrete absorbent articles advancing the machine direction MD from FIG. 8 taken along line G-G.

DETAILED DESCRIPTION OF THE INVENTION

Figure 1A:
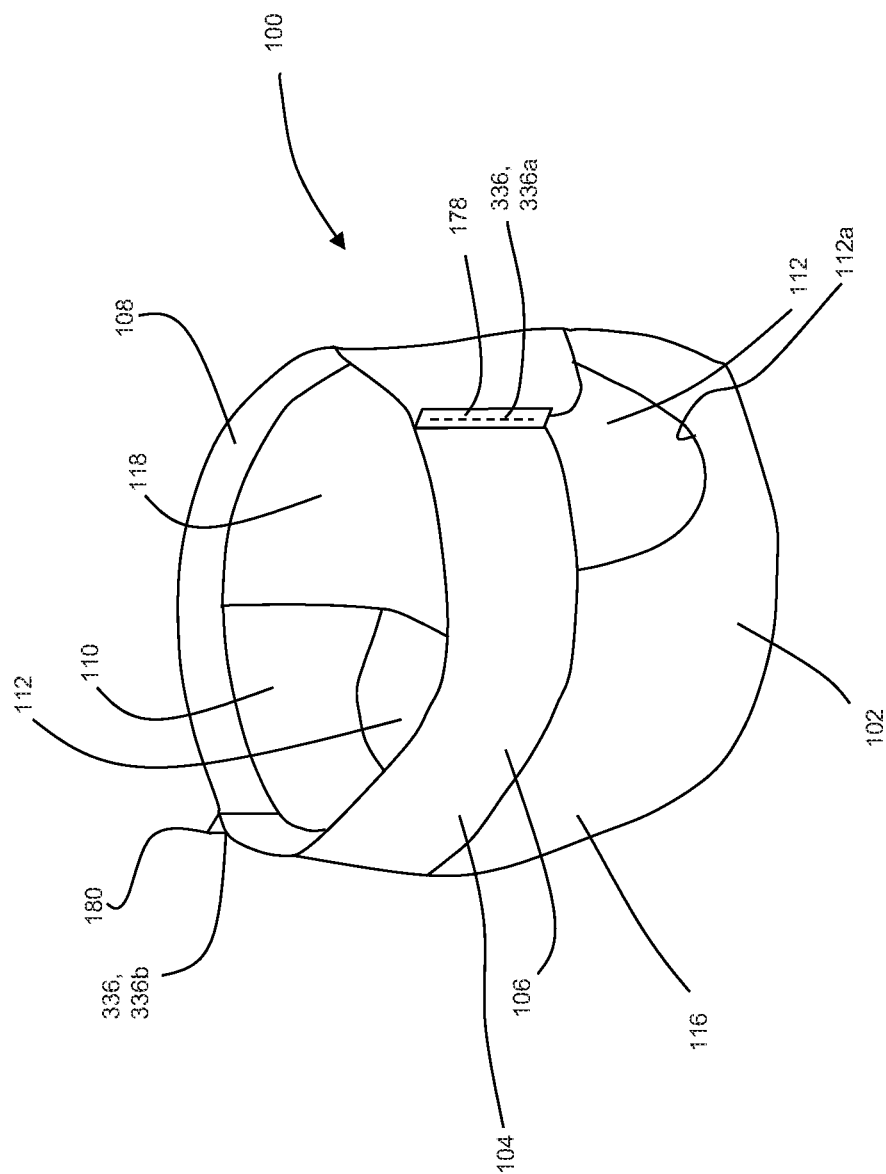
FIG. 1A is a front perspective view of a diaper pant.

The following term explanations may be useful in understanding the present disclosure:

"Absorbent article" is used herein to refer to consumer products whose primary function is to absorb and retain soils and wastes. "Diaper" is used herein to refer to an absorbent article generally worn by infants and incontinent persons about the lower torso. The term "disposable" is used herein to describe absorbent articles which generally are not intended to be laundered or otherwise restored or reused as an absorbent article (e.g., they are intended to be discarded after a single use and may also be configured to be recycled, composted or otherwise disposed of in an environmentally compatible manner).

An "elastic," "elastomer" or "elastomeric" refers to materials exhibiting elastic properties, which include any material that upon application of a force to its relaxed, initial length can stretch or elongate to an elongated length more than 10% greater than its initial length and will substantially recover back to about its initial length upon release of the applied force.

As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.

"Longitudinal" means a direction running substantially perpendicular from a waist edge to a longitudinally opposing waist edge of an absorbent article when the article is in a flat out, uncontracted state, or from a waist edge to the bottom of the crotch, i.e. the fold line, in a bi-folded article. Directions within 45 degrees of the longitudinal direction are considered to be "longitudinal." "Lateral" refers to a direction running from a longitudinally extending side edge to a laterally opposing longitudinally extending side edge of an article and generally at a right angle to the longitudinal direction. Directions within 45 degrees of the lateral direction are considered to be "lateral."

The term "substrate" is used herein to describe a material which is primarily two-dimensional (i.e. in an XY plane) and whose thickness (in a Z direction) is relatively small (i.e. 1/10 or less) in comparison to its length (in an X direction) and width (in a Y direction). Non-limiting examples of substrates include a web, layer or layers or fibrous materials, nonwovens, films and foils such as polymeric films or metallic foils. These materials may be used alone or may comprise two or more layers laminated together. As such, a web is a substrate.

The term "nonwoven" refers herein to a material made from continuous (long) filaments (fibers) and/or discontinuous (short) filaments (fibers) by processes such as spunbonding, meltblowing, carding, and the like. Nonwovens do not have a woven or knitted filament pattern.

The term "machine direction" (MD) is used herein to refer to the direction of material flow through a process. In addition, relative placement and movement of material can be described as flowing in the machine direction through a process from upstream in the process to downstream in the process.

The term "cross direction" (CD) is used herein to refer to a direction that is generally perpendicular to the machine direction.

The term "pant" (also referred to as "training pant", "pre-closed diaper", "diaper pant", "pant diaper", and "pull-on diaper") refers herein to disposable absorbent articles having a continuous perimeter waist opening and continuous perimeter leg openings designed for infant or adult wearers. A pant can be configured with a continuous or closed waist opening and at least one continuous, closed, leg opening prior to the article being applied to the wearer. A pant can be preformed by various techniques including, but not limited to, joining together portions of the article using any refastenable and/or permanent closure member (e.g., seams, heat bonds, pressure welds, adhesives, cohesive bonds, mechanical fasteners, etc.). A pant can be preformed anywhere along the circumference of the article in the waist region (e.g., side fastened or seamed, front waist fastened or seamed, rear waist fastened or seamed).

The present disclosure relates to methods for sealing absorbent cores of absorbent articles, and more particularly, disposable diaper pants, during the assembly process. The diaper pants may include a chassis connected with a ring-like elastic belt, wherein the ring-like elastic belt may include a first elastic belt and a second elastic belt bonded together. The chassis includes a topsheet, a backsheet, and an absorbent core disposed between the topsheet and the backsheet. And the absorbent core may include a first substrate, a second substrate bonded with the first substrate, and absorbent material positioned between the first and second substrates. As discussed below, aspects of the assembly methods herein involve bonding a continuous length of absorbent cores between a continuous topsheet substrate and a continuous backsheet substrate advancing in a machine direction. The combined continuous topsheet substrate, continuous backsheet substrate, and continuous length of absorbent cores are then cut along a cross direction to create discrete chassis, wherein the topsheet, the backsheet, and the absorbent core of each chassis have equal longitudinal lengths. The discrete chassis are then deposited onto a first continuous elastic laminate and a second continuous elastic laminate. Opposing end regions of the absorbent cores may then be sealed by folding a portion of the first and/or second elastic laminates across the topsheets of the chassis. Each chassis may then be folded along a lateral axis to position the first continuous elastic laminate into a facing relationship with the second continuous elastic laminate. The first and second continuous elastic laminates are then bonded together and cut to form discrete diaper pants.

As discussed above, the folded portions of the first and/or second elastic laminates may define a sealing layer to seal the absorbent core and help prevent absorbent material from escaping during use. As such, the sealing layers may be created in accordance with the methods herein without the need to bond the backsheet and topsheet to completely surround the periphery of the absorbent core and/or create discrete absorbent cores that are subsequently placed between advancing continuous topsheet and backsheet webs. As discussed in more detail below, the sealing layer may be in the form of a continuous or discrete strip of material. And such a strip of material may also be cut from the first and/or second continuous elastic laminates during the assembly process. It is to be appreciated that the methods herein may utilize additional transformations to help seal the absorbent cores. For example, adhesives and/or mechanical bonds may also be applied to end regions of the topsheets and continuous elastic substrates.

It is to be appreciated that the processes and apparatuses discussed herein may be used in the manufacture of different types of absorbent articles. To help provide additional context to the subsequent discussion of the process embodiments, the following provides a general description of absorbent articles in the form of diaper pants that may be assembled in accordance with the methods and apparatuses disclosed herein.

Figure 1B:
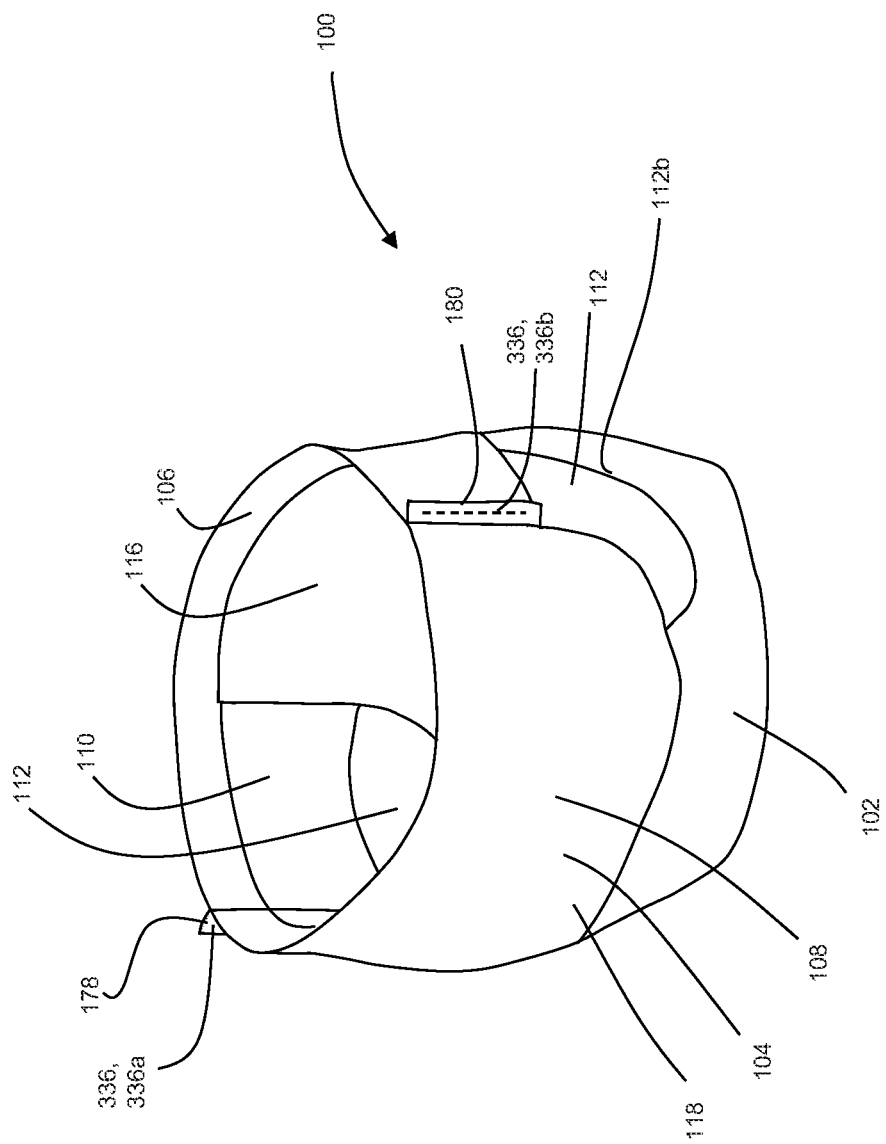
FIG. 1B is a rear perspective view of a diaper pant.
Figure 2B:
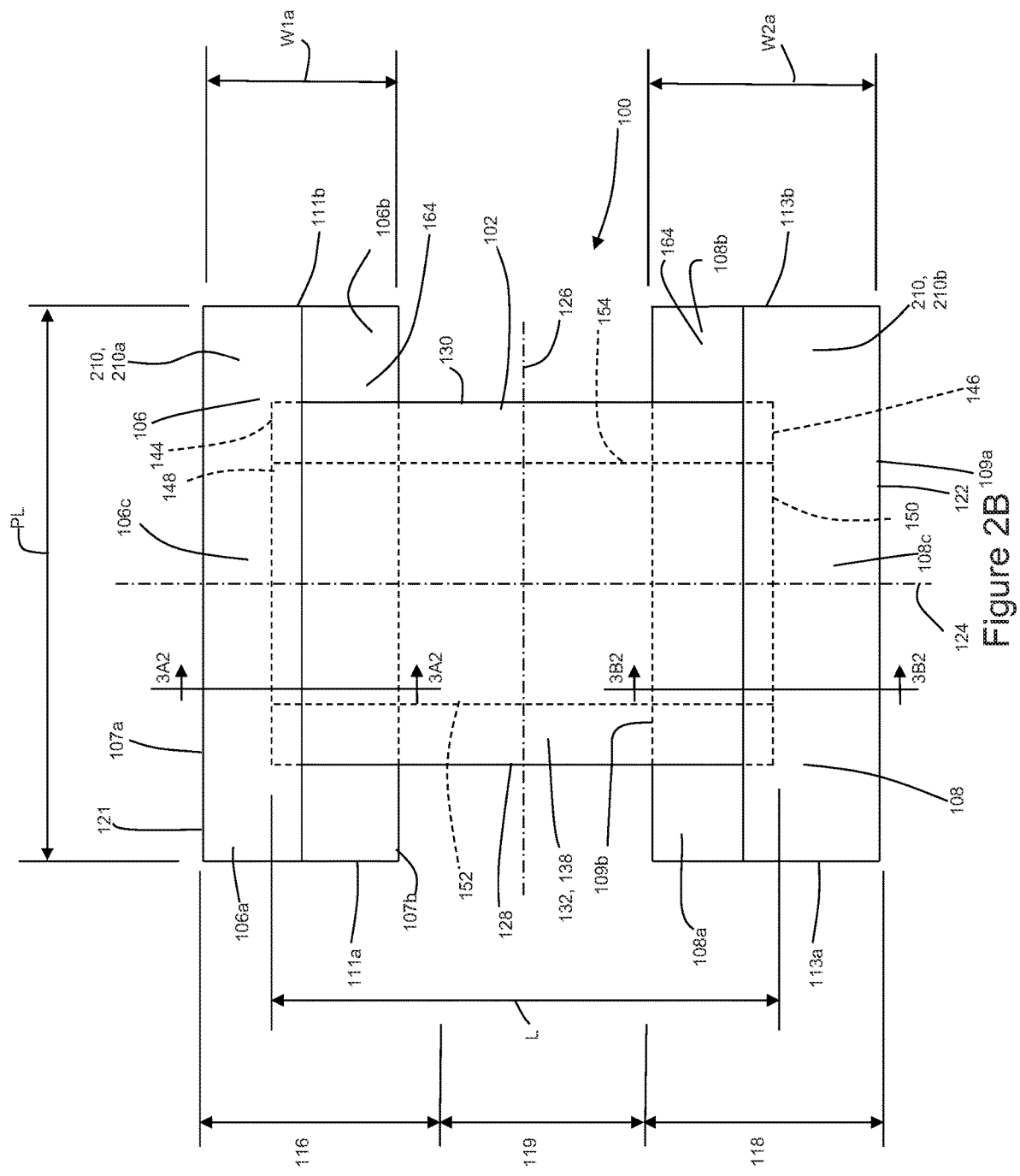
FIG. 2B is a plan view of the diaper pant shown in FIGS. 1A and 1B in a flat, uncontracted state with the portion of the diaper that faces toward a wearer oriented towards the viewer.

FIGS. 1A, 1B, 2A, and 2B show an example of a diaper pant 100 that may be assembled in accordance with the apparatuses and methods disclosed herein. In particular, FIGS. 1A and 1B show perspective views of a diaper pant 100 in a pre-fastened configuration. FIG. 2A shows a plan view of the diaper pant 100 with the portion of the diaper that faces away from a wearer oriented toward the viewer, and FIG. 2B shows a plan view of the diaper pant 100 with the portion of the diaper that faces toward a wearer oriented toward the viewer. The diaper pant 100 includes a chassis 102 and a ring-like elastic belt 104. As discussed below in more detail, a first elastic belt 106 and a second elastic belt 108 are bonded together to form the ring-like elastic belt 104.

With continued reference to FIGS. 2A and 2B, the diaper pant 100 and the chassis 102 each include a first waist region 116, a second waist region 118, and a crotch region 119 disposed intermediate the first and second waist regions. The first waist region 116 may be configured as a front waist region, and the second waist region 118 may be configured as back waist region. In some embodiments, the length of each of the front waist region, back waist region, and crotch region may be about ⅓ of the length of the absorbent article 100. The diaper 100 may also include a laterally extending front waist edge 121 in the front waist region 116 and a longitudinally opposing and laterally extending back waist edge 122 in the back waist region 118. To provide a frame of reference for the present discussion, the diaper 100 and chassis 102 of FIGS. 2A and 2B are shown with a longitudinal axis 124 and a lateral axis 126. In some embodiments, the longitudinal axis 124 may extend through the front waist edge 121 and through the back waist edge 122. And the lateral axis 126 may extend through a first longitudinal or right side edge 128 and may be proximate a midpoint of a second longitudinal or left side edge 130 of the chassis 102.

As shown in FIGS. 1A, 1B, 2A, and 2B, the diaper pant 100 may include an inner, body facing surface 132, and an outer, garment facing surface 134. The chassis 102 may include a backsheet 136 and a topsheet 138. The chassis 102 may also include an absorbent assembly 200, including an absorbent core 202, disposed between a portion of the topsheet 138 and the backsheet 136. As discussed in more detail below, the diaper 100 may also include other features, such as leg elastics and/or leg cuffs to enhance the fit around the legs of the wearer.

As shown in FIGS. 2A and 2B, the periphery of the chassis 102 may be defined by the first longitudinal side edge 128, a second longitudinal side edge 130, a first laterally extending end edge 144 disposed in the first waist region 116, and a second laterally extending end edge 146 disposed in the second waist region 118. Both side edges 128 and 130 extend longitudinally between the first end edge 144 and the second end edge 146. As shown in FIG. 2A, the laterally extending end edges 144 and 146 are located longitudinally inward from the laterally extending front waist edge 121 in the front waist region 116 and the laterally extending back waist edge 122 in the back waist region 118. When the diaper pant 100 is worn on the lower torso of a wearer, the front waist edge 121 and the back waist edge 122 may encircle a portion of the waist of the wearer. At the same time, the side edges 128 and 130 may encircle at least a portion of the legs of the wearer. And the crotch region 119 may be generally positioned between the legs of the wearer with the absorbent core 202 extending from the front waist region 116 through the crotch region 119 to the back waist region 118.

As previously mentioned, the diaper pant 100 may include a backsheet 136. The backsheet 136 may also define the outer surface 134 of the chassis 102. The backsheet 136 may be impervious to fluids (e.g., menses, urine, and/or runny feces) and may be manufactured in part from a thin plastic film, although other flexible liquid impervious materials may also be used. The backsheet 136 may prevent the exudates absorbed and contained in the absorbent core from wetting articles which contact the diaper 100, such as bedsheets, pajamas and undergarments. The backsheet 136 may also comprise a woven or nonwoven material, polymeric films such as thermoplastic films of polyethylene or polypropylene, and/or a multi-layer or composite materials comprising a film and a nonwoven material (e.g., having an inner film layer and an outer nonwoven layer). The backsheet may also comprise an elastomeric film. An example backsheet 136 may be a polyethylene film having a thickness of from about 0.012 mm (0.5 mils) to about 0.051 mm (2.0 mils). Exemplary polyethylene films are manufactured by Clopay Corporation of Cincinnati, Ohio, under the designation BR-120 and BR-121 and by Tredegar Film Products of Terre Haute, Ind., under the designation XP-39385. The backsheet 136 may also be embossed and/or matte-finished to provide a more clothlike appearance. Further, the backsheet 136 may permit vapors to escape from the absorbent core (i.e., the backsheet is breathable) while still preventing exudates from passing through the backsheet 136. The size of the backsheet 136 may be dictated by the size of the absorbent core 202 and/or particular configuration or size of the diaper 100.

Also described above, the diaper pant 100 may include a topsheet 138. The topsheet 138 may also define all or part of the inner surface 132 of the chassis 102. The topsheet 138 may be compliant, soft feeling, and non-irritating to the wearer's skin. It may be elastically stretchable in one or two directions. Further, the topsheet 138 may be liquid pervious, permitting liquids (e.g., menses, urine, and/or runny feces) to penetrate through its thickness. A topsheet 138 may be manufactured from a wide range of materials such as woven and nonwoven materials; apertured or hydroformed thermoplastic films; apertured nonwovens, porous foams; reticulated foams; reticulated thermoplastic films; and thermoplastic scrims. Woven and nonwoven materials may comprise natural fibers such as wood or cotton fibers; synthetic fibers such as polyester, polypropylene, or polyethylene fibers; or combinations thereof. If the topsheet 138 includes fibers, the fibers may be spunbond, carded, wet-laid, meltblown, hydroentangled, or otherwise processed as is known in the art.

Topsheets 138 may be selected from high loft nonwoven topsheets, apertured film topsheets and apertured nonwoven topsheets. Apertured film topsheets may be pervious to bodily exudates, yet substantially non-absorbent, and have a reduced tendency to allow fluids to pass back through and rewet the wearer's skin. Exemplary apertured films may include those described in U.S. Pat. Nos. 5,628,097; 5,916,661; 6,545,197; and 6,107,539.

As mentioned above, the diaper pant 100 may also include an absorbent core 202 that is joined to the chassis 102. As shown in FIGS. 2A and 2B, the absorbent core 202 may have a laterally extending front edge 148 in the front waist region 116 and may have a longitudinally opposing and laterally extending back edge 150 in the back waist region 118. The absorbent core 202 may also define a longitudinal length L that is equal to the longitudinal lengths of the backsheet 136 and the topsheet 138. As such, the front edge 148 of the absorbent core 202 may also be coextensive with the first laterally extending end edge 144 of the chassis 102, and the back edge 150 of the absorbent core 202 may also be coextensive with the second laterally extending end edge 146 of the chassis 102. The absorbent core 202 may also have a longitudinally extending right side edge 152 and may have a laterally opposing and longitudinally extending left side edge 154, both absorbent core side edges 152 and 154 may extend longitudinally between the front edge 148 and the back edge 150. The absorbent core 202 is disposed between the topsheet 138 and the backsheet 136 and may be formed in various sizes and shapes that are compatible with the diaper. In some configurations, the absorbent core 202 may define a width that is narrower than a width defined by the chassis 102, and as such, the absorbent core side edges 152 and 154 may be positioned laterally inboard of the chassis side edges 128, 130.

With reference to FIGS. 2B, 3A2, and 3B2, the absorbent core 202 includes a first substrate 204, a second substrate 206 bonded with the first substrate 204, and absorbent material 208 between the first and second substrates 204, 206. The first substrate and/or the second substrates 204, 206 may extend longitudinally for length, L, which may be the same as the longitudinal length of the topsheet 138 and/or backsheet 136. The first substrate 204 of the absorbent core 202 may be referred to as a dusting layer and has a first surface which faces the backsheet 136 of the chassis 102 and a second surface which faces the absorbent material 208. The second substrate 206 of the absorbent core 202 may be referred to as a core cover and has a first surface facing the topsheet 138 of the chassis 102 and a second surface facing the absorbent material 208. The first substrate 204 may include the same material as the second substrate 206, or may include a different material. In some configurations, the first substrate 204 and/or the second substrate 206 may include nonwoven materials. The first and second substrates 204, 206 may be adhered to one another with adhesive about the periphery to form an envelope about the absorbent material to help hold the absorbent material 208 within the absorbent core 202. It is to be appreciated that the absorbent material 208 may extend longitudinally for a length that is less than the longitudinal lengths of the first substrate and/or the second substrates 204, 206.

It is to be appreciated that the absorbent material 208 may include various types of materials. In some configurations, the absorbent material 208 may include any absorbent material that is generally compressible, conformable, non-irritating to the wearer's skin, and capable of absorbing and retaining liquids such as urine and other certain body exudates. In some configurations, the absorbent core 202 may comprise a wide variety of liquid-absorbent materials commonly used in disposable diapers and other absorbent articles such as comminuted wood pulp, which is generally referred to as airfelt, creped cellulose wadding, melt blown polymers, including co-form, chemically stiffened, modified or cross-linked cellulosic fibers, tissue, including tissue wraps and tissue laminates, absorbent foams, absorbent sponges, or any other known absorbent material or combinations of materials. The absorbent core 202 may further comprise minor amounts (sometimes less than about 10%) of materials, such as adhesives, waxes, oils and the like.

Some absorbent core 202 embodiments may comprise fluid storage cores that contain reduced amounts of cellulosic airfelt material. For instance, such absorbent cores 202 may comprise less than about 40%, 30%, 20%, 10%, 5%, or even 1% of cellulosic airfelt material. Such a core may comprises primarily absorbent gelling material, such as absorbent particulate polymer material, in amounts of at least about 60%, 70%, 80%, 85%, 90%, 95%, or even about 100%, where the remainder of the core comprises a microfiber glue (if applicable). Such cores, microfiber glues, and absorbent gelling materials are described in U.S. Pat. Nos. 5,599,335; 5,562,646; 5,669,894; and 6,790,798 as well as U.S. Patent Publication Nos. 2004/0158212 A1 and 2004/0097895 A1.

In some configurations, the absorbent assembly 200 may include an acquisition system disposed between the topsheet 138 and a wearer facing side of the absorbent core 202. The acquisition system may be in direct contact with the absorbent core 202 and may comprise a single layer or multiple layers, such as an upper acquisition layer (also referred to herein as a first acquisition layer) facing towards the wearer's skin and a lower acquisition layer (also referred to herein as a second acquisition layer) facing the garment of the wearer. In some embodiments, the acquisition system may function to receive a surge of liquid, such as a gush of urine. As such, the acquisition system may serve as a temporary reservoir for liquid until the absorbent core 202 can absorb the liquid. Exemplary acquisition systems and associated manufacturing processes are described in U.S. Pat. Nos. 8,603,277 and 8,568,566; U.S. Patent Publication Nos. 2012/0316046 A1 and 2014/0163504 A1, all of which are hereby incorporated by reference herein.

In some configurations, the acquisition system may include chemically cross-linked cellulosic fibers. Such cross-linked cellulosic fibers may have various absorbency properties. Exemplary chemically cross-linked cellulosic fibers are disclosed in U.S. Pat. No. 5,137,537. Citric acid is an exemplary cross-linking agent. In some embodiments, polyacrylic acids may be used. In some configurations, the cross-linked cellulosic fibers may be crimped, twisted, or curled, or a combination thereof including crimped, twisted, and curled.

In some configurations, one or both of the upper acquisition layer and lower acquisition layer may include a nonwoven, which may be hydrophilic. Further, according to some configurations, one or both of the upper acquisition layer and lower acquisition layer may comprise chemically cross-linked cellulosic fibers, which may or may not form part of a nonwoven material. In some embodiments, the upper acquisition layer may comprise a nonwoven, without the cross-linked cellulosic fibers, and the lower acquisition layer may comprise the chemically cross-linked cellulosic fibers. Further, in some embodiments, the lower acquisition layer may comprise the chemically cross-linked cellulosic fibers mixed with other fibers such as natural or synthetic polymeric fibers. According to some embodiments, such other natural or synthetic polymeric fibers may include high surface area fibers, thermoplastic binding fibers, polyethylene fibers, polypropylene fibers, PET fibers, rayon fibers, lyocell fibers, and mixtures thereof.

Exemplary absorbent assemblies 200, absorbent cores 202, and associated components that may be adapted for use with the present disclosure are described in U.S. Pat. Nos. 4,610,678; 4,673,402; 4,888,231; 4,834,735; 4,888,231; 5,260,345; 5,387,207; 5,397,316; 8,603,277; and 8,568,566; and U.S. Patent Publication Nos. 2012/0316046 A1 and 2014/0163504 A1, all of which are hereby incorporated by reference herein.

As previously mentioned, the diaper 100 may also include elasticized leg cuffs 156. It is to be appreciated that the leg cuffs 156 can be and are sometimes also referred to as leg bands, side flaps, barrier cuffs, elastic cuffs or gasketing cuffs. The elasticized leg cuffs 156 may be configured in various ways to help reduce the leakage of body exudates in the leg regions. Example leg cuffs 156 may include those described in U.S. Pat. Nos. 3,860,003; 4,909,803; 4,695,278; 4,795,454; 4,704,115; 4,909,803; and U.S. Patent Publication No. 2009/0312730 A1.

As mentioned above, diaper pants may be manufactured with a ring-like elastic belt 104 and provided to consumers in a configuration wherein the front waist region 116 and the back waist region 118 are connected to each other as packaged, prior to being applied to the wearer. As such, diaper pants may have a continuous perimeter waist opening 110 and continuous perimeter leg openings 112 such as shown in FIGS. 1A and 1B. The ring-like elastic belt may be formed by joining a first elastic belt to a second elastic belt with a permanent side seam or with an openable and reclosable fastening system disposed at or adjacent the laterally opposing sides of the belts.

As previously mentioned, the ring-like elastic belt 104 may be defined by a first elastic belt 106 connected with a second elastic belt 108. As shown in FIGS. 2A and 2B, the first elastic belt 106 extends between a first longitudinal side edge 111a and a second longitudinal side edge 111b and defines first and second opposing end regions 106a, 106b and a central region 106c. And the second elastic belt 108 extends between a first longitudinal side edge 113a and a second longitudinal side edge 113b and defines first and second opposing end regions 108a, 108b and a central region 108c. The distance between the first longitudinal side edge 111a and the second longitudinal side edge 111b defines the pitch length, PL, of the first elastic belt 106, and the distance between the first longitudinal side edge 113a and the second longitudinal side edge 113b defines the pitch length, PL, of the second elastic belt 108. The central region 106c of the first elastic belt is connected with the first waist region 116 of the chassis 102, and the central region 108c of the second elastic belt 108 is connected with the second waist region 118 of the chassis 102. As shown in FIGS. 1A and 1B, the first end region 106a of the first elastic belt 106 is connected with the first end region 108a of the second elastic belt 108 at first side seam 178, and the second end region 106b of the first elastic belt 106 is connected with the second end region 108b of the second elastic belt 108 at second side seam 180 to define the ring-like elastic belt 104 as well as the waist opening 110 and leg openings 112.

As shown in FIGS. 2A, 3A1, and 3B1, the first elastic belt 106 also defines an outer laterally extending edge 107a and an inner laterally extending edge 107b, and the second elastic belt 108 defines an outer laterally extending edge 109a and an inner laterally extending edge 109b. As such, a perimeter edge 112a of one leg opening may be defined by portions of the inner laterally extending edge 107b of the first elastic belt 106, the inner laterally extending edge 109b of the second elastic belt 108, and the first longitudinal or right side edge 128 of the chassis 102. And a perimeter edge 112b of the other leg opening may be defined by portions of the inner laterally extending edge 107b of the first elastic belt 106, the inner laterally extending edge 109b of the second elastic belt 108, and the second longitudinal or left side edge 130 of the chassis 102. The outer laterally extending edges 107a, 109a may also define the front waist edge 121 and the laterally extending back waist edge 122 of the diaper pant 100. The first elastic belt and the second elastic belt may also each include an outer, garment facing layer 162 and an inner, wearer facing layer 164. It is to be appreciated that the first elastic belt 106 and the second elastic belt 108 may comprise the same materials and/or may have the same structure. In some embodiments, the first elastic belt 106 and the second elastic belt may comprise different materials and/or may have different structures. It should also be appreciated that the first elastic belt 106 and the second elastic belt 108 may be constructed from various materials. For example, the first and second belts may be manufactured from materials such as plastic films; apertured plastic films; woven or nonwoven webs of natural materials (e.g., wood or cotton fibers), synthetic fibers (e.g., polyolefins, polyamides, polyester, polyethylene, or polypropylene fibers) or a combination of natural and/or synthetic fibers; or coated woven or nonwoven webs. In some embodiments, the first and second elastic belts include a nonwoven web of synthetic fibers, and may include a stretchable nonwoven. In other embodiments, the first and second elastic belts include an inner hydrophobic, non-stretchable nonwoven material and an outer hydrophobic, non-stretchable nonwoven material.

The first and second elastic belts 106, 108 may also each include belt elastic material interposed between the outer substrate layer 162 and the inner substrate layer 164. The belt elastic material may include one or more elastic elements such as strands, ribbons, films, or panels extending along the lengths of the elastic belts. As shown in FIGS. 2A, 3A1, and 3B1, the belt elastic material may include a plurality of elastic strands 168 which may be referred to herein as outer, waist elastics 170 and inner, waist elastics 172. Elastic strands 168, such as the outer waist elastics 170, may continuously extend laterally between the first and second opposing end regions 106a, 106b of the first elastic belt 106 and between the first and second opposing end regions 108a, 108b of the second elastic belt 108. In some embodiments, some elastic strands 168, such as the inner waist elastics 172, may be configured with discontinuities in areas, such as for example, where the first and second elastic belts 106, 108 overlap the absorbent core 202. In some embodiments, the elastic strands 168 may be disposed at a constant interval in the longitudinal direction. In other embodiments, the elastic strands 168 may be disposed at different intervals in the longitudinal direction. The belt elastic material in a stretched condition may be interposed and joined between the uncontracted outer layer and the uncontracted inner layer. When the belt elastic material is relaxed, the belt elastic material returns to an unstretched condition and contracts the outer layer and the inner layer. The belt elastic material may provide a desired variation of contraction force in the area of the ring-like elastic belt. It is to be appreciated that the chassis 102 and elastic belts 106, 108 may be configured in different ways other than as depicted in FIG. 2A. The belt elastic material may be joined to the outer and/or inner layers continuously or intermittently along the interface between the belt elastic material and the inner and/or outer belt layers.

In some configurations, the first elastic belt 106 and/or second elastic belt 108 may define curved contours. For example, the inner lateral edges 107b, 109b of the first and/or second elastic belts 106, 108 may include non-linear or curved portions in the first and second opposing end regions. Such curved contours may help define desired shapes to leg opening 112, such as for example, relatively rounded leg openings. In addition to having curved contours, the elastic belts 106, 108 may include elastic strands 168, 172 that extend along non-linear or curved paths that may correspond with the curved contours of the inner lateral edges 107b, 109b.

As shown in FIGS. 2B, 3A2, 3B2, the diaper 100 may include a sealing layer 210 configured to seal opposing end portions of the absorbent core 202. For example, as shown in FIG. 3A2, a first sealing layer 210a may be configured to overlap the laterally extending front edge 148 of the absorbent core 202 and the first laterally extending end edge 144 of the chassis 102. As previously mentioned, the chassis 102 and the absorbent core 202 may define the same longitudinal lengths L, and as such, the laterally extending front edge 148 of the absorbent core 202 may be coextensive with the first laterally extending end edge 144 of the chassis 102. Thus, the first sealing layer 210a may be connected with the topsheet 138 and the inner, wearer facing layer 164 of the first elastic belt 106 such that the topsheet 138, the backsheet 136, the first substrate 204, the second substrate 206, and the topsheet 138 are positioned between the inner, wearer facing layer 164 and the first sealing layer 210a. As shown in FIG. 3B2, a second sealing layer 210b may be configured to overlap the laterally extending back edge 150 of the absorbent core 202 and the second laterally extending end edge 146 of the chassis 102. As previously mentioned, the chassis 102 and the absorbent core 202 may define the same longitudinal lengths L, and as such, the laterally extending back edge 150 of the absorbent core 202 may be coextensive with the second laterally extending end edge 146 of the chassis 102. Thus, the second sealing layer 210b may be connected with the topsheet 138 and the inner, wearer facing layer 164 of the second elastic belt 108 such that the topsheet 138, the backsheet 136, the first substrate 204, the second substrate 206, and the topsheet 138 are positioned between the inner, wearer facing layer 164 and the second sealing layer 210b.

It is to be appreciated that sealing layers 210 may be formed in various ways. For example, as shown in FIGS. 3A2 and 3B2, the first sealing layer 210a may comprise a portion of outer, garment facing layer 162 of the first elastic belt 106 that is folded onto the topsheet 138 of the chassis 102 and placed in a facing relationship with the inner, wearer facing layer 164 of the first elastic belt 106. And the second sealing layer 210b may comprise a portion of outer, garment facing layer 162 of the second elastic belt 108 that is folded onto the topsheet 138 of the chassis 102 and placed in a facing relationship with the inner, wearer facing layer 164 of the second elastic belt 108. In some configurations, the first sealing layer 210a may comprise a portion of inner, wearer facing layer 164 of the first elastic belt 106 that is folded onto the topsheet 138 of the chassis 102 and placed in a facing relationship with the inner, wearer facing layer 164 of the first elastic belt 106. And the second sealing layer 210b may comprise a portion of inner, wearer facing layer 164 of the second elastic belt 108 that is folded onto the topsheet 138 of the chassis 102 and placed in a facing relationship with the inner, wearer facing layer 164 of the second elastic belt 108.

It is to be appreciated the sealing layers 210 may be bonded to the inner, wearer facing layer 164 and the topsheet 138 to help prevent absorbent material 208 from migrating or escaping longitudinally from absorbent core 202 from between the first and second substrates 204, 206 and/or from between the backsheet 136 and the topsheet 138. As opposed to folding a portion of the first and/or second belts 106, 108 to form the sealing layers, in some configurations, the sealing layers 210 may be formed from a separate strip of material that is bonded to the first and/or second belts 106, 108.

Figure 4:
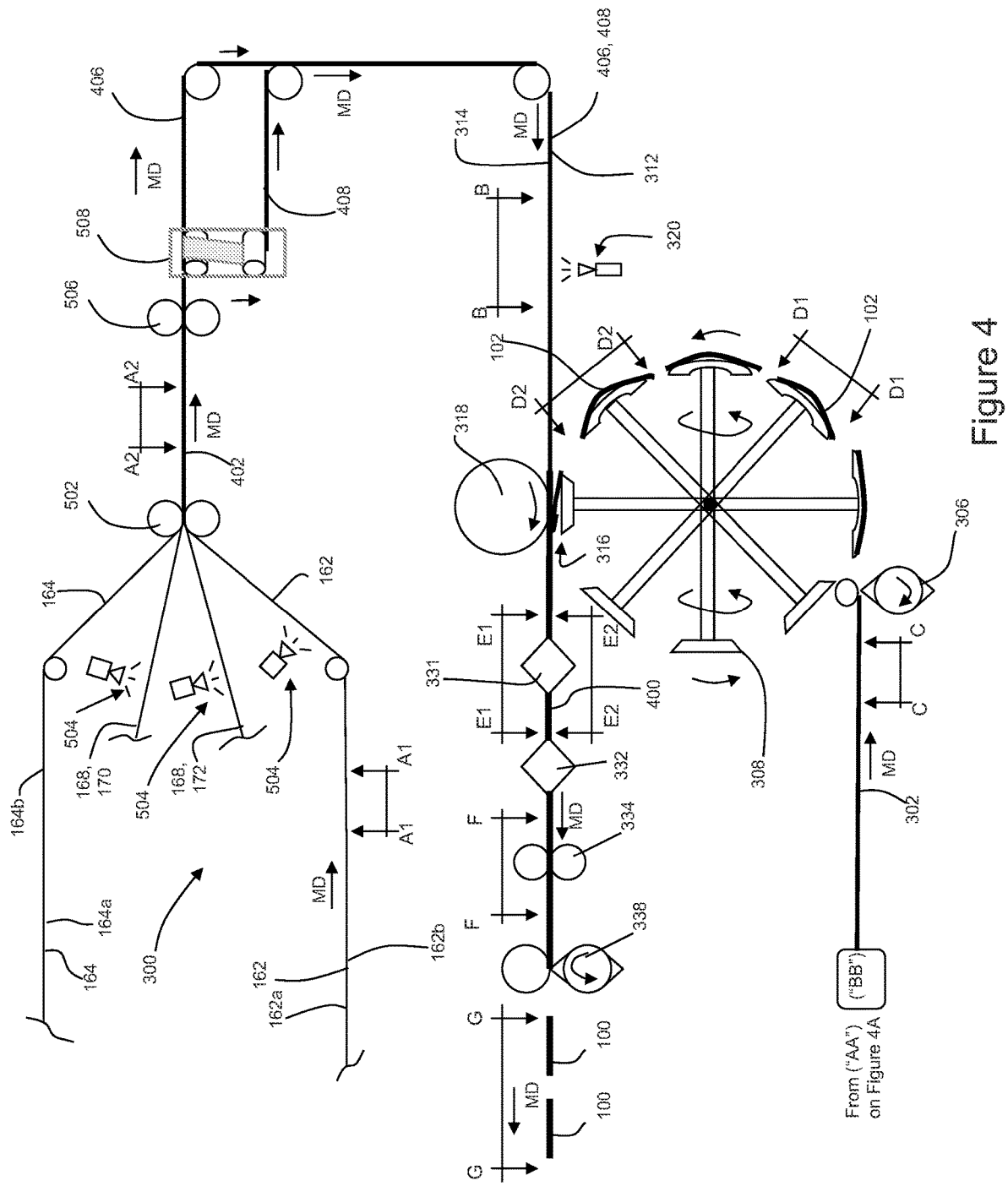
FIG. 4 is a schematic side view of a converting apparatus adapted to manufacture pre-fastened, pant diapers.

It is to be appreciated that various apparatuses and methods according to the present disclosure may be utilized to assemble various components of pre-fastened pant diapers 100 described herein. For example, FIG. 4 shows a schematic view of a converting apparatus 300 adapted to manufacture pant diapers 100. The method of operation of the converting apparatus 300 may be described with reference to the various components of pant diapers 100 described above and shown in FIGS. 1A, 1B, 2A, and 2B. Although the following methods are provided in the context of the diaper 100 shown in FIGS. 1A, 1B, 2A, and 2B, it is to be appreciated that various embodiments of diaper pants can be manufactured according to the methods disclosed herein, such as for example, the absorbent articles disclosed in U.S. Pat. No. 7,569,039; U.S. Patent Publication Nos. 2005/

0107764 A1, 2012/0061016 A1, and 2012/0061015 A1, which are all hereby incorporated by reference herein.

As described in more detail below, the converting apparatus 300 shown in FIG. 4 operates to advance first and second elastic belt laminates 406, 408 along a machine direction MD. In addition, a continuous length of chassis assemblies 302 are advanced in a machine direction MD and cut into discrete chassis 102 such that the longitudinal axis 124 of each chassis 102 is parallel with the machine direction MD. The discrete chassis 102 are then turned to advance the discrete chassis 102 along the machine direction MD such that the lateral axis 126 of each chassis 102 is parallel with the machine direction MD. The discrete chassis 102 are also spaced apart from each other along the machine direction MD. Opposing waist regions 116, 118 of the spaced apart chassis 102 are then connected with continuous lengths of advancing first and second elastic belt laminates 406, 408. The chassis 102 may then be folded along the lateral axis, or parallel to the lateral axis, to bring the first and second elastic belt laminates 406, 408 into a facing relationship, and the first and second elastic belt laminates are bonded together with laterally opposing bonds 336. As discussed in more detail below, the first and second elastic belt laminates may be bonded together with adjacent bonds 336a, 336b intermittently spaced along the machine direction MD. It is to be appreciated that the bonds 336a, 336b may be configured as permanent and/or refastenable bonds. And each bond 336a, 336b may be a discrete bond site extending contiguously in a cross direction CD across a width of the first and second elastic belt laminates and/or may include a plurality of relatively small, discrete bond sites arranged in the cross direction. The first and second continuous elastic laminates 406, 408 are then cut in the cross direction CD between adjacent bonds 336a, 336b to create discrete pant diapers 100, such as shown in FIGS. 1A and 1B.

As shown in FIG. 4, a first continuous substrate layer in the form of a continuous length of outer layer belt substrate 162; a second continuous substrate layer in the form of a continuous length of inner layer belt substrate 164; and elastics 168 are combined to form a continuous elastic laminate 402 in the form of a belt material. More particularly, continuous lengths of outer layer belt substrate 162, inner layer belt substrate 164, outer elastic strands 170 and inner elastic strands 172 are advanced in a machine direction MD and combined at nip rolls 502 to form the continuous elastic laminate 402.

As shown in FIGS. 4, 5A1, and 5A2, the outer belt substrate 162 includes a first surface 162a and an opposing second surface 162b, and defines a width W in the cross direction CD between opposing first and second longitudinal edges 163a, 163b. And the inner belt substrate 164 includes first surface 164a and an opposing second surface 164b, and defines a width in the cross direction CD between opposing first and second longitudinal edges 165a, 165b. As shown in FIG. 5A2, the width W of the outer belt substrate 162 may be greater than the width of the inner belt substrate 164. And the width W of the outer belt substrate 162 may also define the width W of the elastic laminate 402. It is to be appreciated that in some embodiments, the width of the inner belt substrate 164 may be the same as or greater than the width of the outer belt substrate 162.

With continued reference to FIG. 4, before entering the nip rolls 502, the outer elastic strands 170 and inner elastic strands 172 are stretched in the machine direction MD. In addition, adhesive 504 may be applied to the elastic strands 170, 172 as well as either or both of the continuous lengths of outer layer belt substrate 162 and inner layer belt substrate 164 before entering nip rolls 502. As such, the elastic strands 168 are bonded between the first surface 162a of the outer layer belt substrate 162 and the first surface 164a of inner layer belt substrate 164 at the nip rolls 502. Further, adhesive 504 may be applied intermittently along the lengths of the inner elastic strands 172 and/or intermittently along the length of either or both of the continuous lengths of outer layer belt substrate 162 and inner layer belt substrate 164 before entering nip rolls 502. As such, the inner elastic strands 172 may be intermittently bonded to either or both of the continuous lengths of outer layer belt substrate 162 and inner layer belt substrate 164 along the machine direction MD. Thus, the continuous elastic laminate 402 may include non-bonded regions intermittently spaced between bonded regions along the machine direction MD, wherein the inner elastic strands 172 are not bonded to either the outer layer belt substrate 162 or inner layer belt substrate 164 in the non-bonded regions. And the inner elastic strands 172 are bonded to the outer layer belt substrate 162 and/or inner layer belt substrate 164 in the bonded regions. As such, the elastic strands 172 may be severed in the non-bonded regions in a subsequent process step. Although FIG. 4 shows an embodiment wherein the continuous elastic laminate 402 is formed by combining continuous lengths of outer layer belt substrate 162 and inner layer belt substrate 164 with elastic strands 168, it is to be appreciated the continuous elastic laminate 402 can be formed in various ways, such as disclosed in U.S. Pat. No. 8,440,043 and U.S. Patent Publication Nos. 2013/0255861 A1; 2013/0255862 A1; 2013/0255863 A1; 2013/0255864 A1; and 2013/0255865 A1.

Figure 5B:
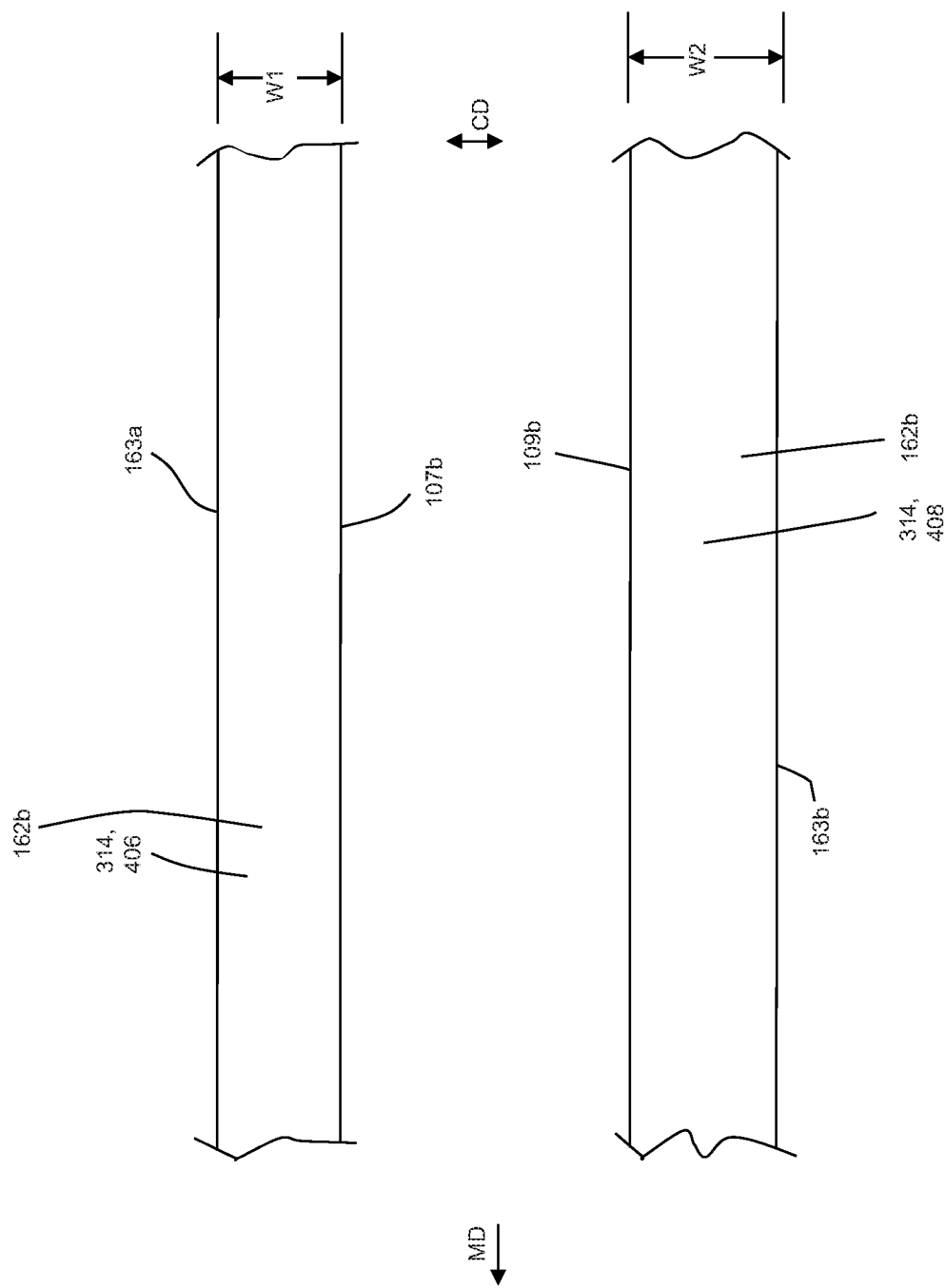
FIG. 5B is a view of continuous lengths of advancing first and second elastic belt laminates from FIG. 4 taken along line B-B.

With continued reference to FIG. 4, from the nip rolls 502 the continuous elastic laminate 402 advances in the machine direction MD to a cutter 506 that cuts the continuous elastic laminate 402 into two continuous elastic belt laminates, referred to as a first elastic belt laminate 406 and a second elastic belt laminate 408. The cutter 506 may be configured in various ways. For example, in some embodiments the cutter 506 may be a slitter or a die cutter that separates the belt material into two continuous belt substrates with either a straight line cut and/or a curved line cut. The cutter 506 may also be configured as a perforator that perforates the belt material with a line of weakness and wherein the belt material is separated along the line of weakness in a later step. From the cutter 506, the first and second belt laminates 406, 408 advance through a diverter 508 that separates the first and second belt substrates from each other in the cross direction CD, such as shown in FIG. 5B. The elastic strands 170, 172, and thus, the continuous length of first and second belt laminates 406, 408 are maintained in a stretched condition while advancing along the machine direction MD. It is to be appreciated that the diverter 508 may be configured in various ways. For example, in some embodiments, the diverter 508 may include turn bars angled at 45 degrees or some other angle with respect to the machine direction MD. In some embodiments, the diverter may include cambered rollers. It is to be appreciated that the first and second belts may be formed by separate continuous lengths of belt material similar to the description above and as such would not required the slitting step or the diverting step.

In some embodiments, the diverter 508 may include a pivot or tracking table, such as for example, the FIFE-500. Web Guiding System, by Maxcess-FIFE Corporation, which can adjust the positions of the continuous length of first and second belt laminates 406, 408 in the cross direction CD. Other suitable pivot or tracking tables are available from Erhardt & Leimer, Inc. The diverter may also include instrumentation and web edge control features that allow for precise active control of the substrate positions.

As shown in FIG. 5B, the first belt laminate 406 includes an outer longitudinal edge 163a and an inner longitudinal edge 107b that may define a substantially constant width, W1, in the cross direction CD. And the second belt laminate 408 includes an outer longitudinal edge 163b and an inner longitudinal edge 109b that may define a substantially constant width, W2, in the cross direction CD, wherein W2 may be greater than W1. It is to be appreciated that in some configurations, W1 may be equal to or greater than W2. As previously mentioned, the first belt laminate 406 is separated in the cross direction CD from the second belt laminate 408 to define a gap between the inner longitudinal edge 107b of the first belt laminate 406 and the inner longitudinal edge 109b of the second belt laminate 408. As discussed in more detail below, the first and second belt laminate 406, 408 advance from the diverter 508 to a nip 316 between the carrier apparatus 308 and a roll 318 to be combined with discrete chassis 102.

Referring now to FIGS. 4 and 5C, a continuous length of chassis assemblies 302 are advanced in a machine direction MD and define a width in a cross direction CD. The continuous length of chassis assemblies 302 may include a continuous length of absorbent cores 212 sandwiched between topsheet material 138 and backsheet material 136, leg elastics, barrier leg cuffs and the like.

Figure 4A:
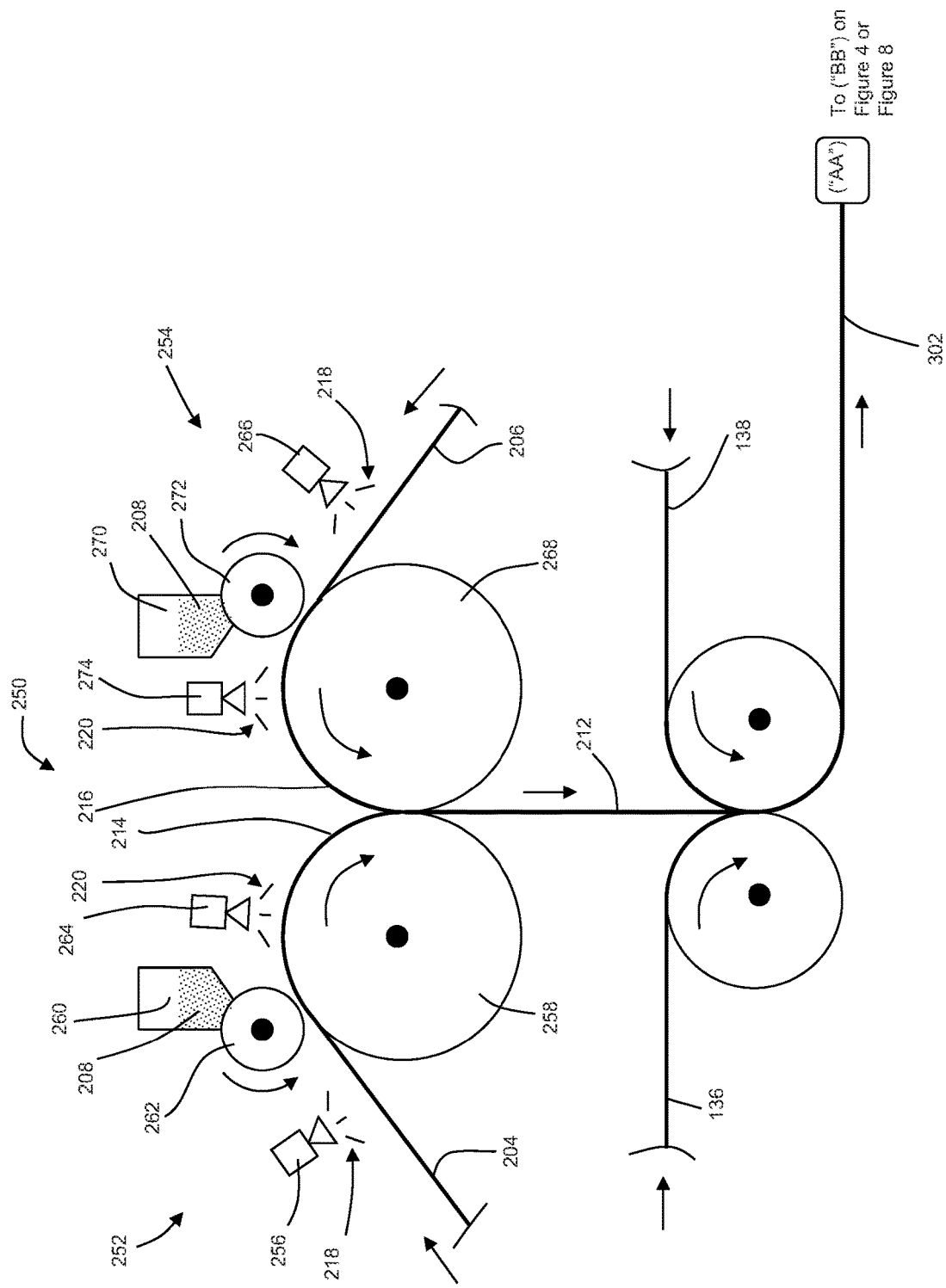
FIG. 4A is a schematic illustration of a process for making a continuous length of chassis assemblies and absorbent cores.

As shown in FIG. 5C, portion of the chassis assembly is cut-away to show a portion of the topsheet material 138 and continuous absorbent cores 212. It is to be appreciated that the continuous length of chassis assemblies 302 and associated absorbent cores 212 may be constructed in various ways. For example, the converting apparatus 300 may include a printing system 250 for making a continuous length of absorbent cores 212, such as shown in FIG. 4A. The printing system 250 may include a first printing unit 252 for forming the first absorbent layer 214 and a second printing unit 254 for forming the second absorbent layer 216. The first printing unit 252 may include a first auxiliary adhesive applicator 256 for applying an auxiliary adhesive 218 to the first substrate 204; a first rotatable support roll 258 for receiving the first substrate 204; a first hopper 260 for absorbent particulate polymer material 208; a first printing roll 262 for transferring the absorbent particulate polymer material 208 from the first hopper 260 to the first substrate 204; and a first thermoplastic adhesive material applicator 264 for applying thermoplastic adhesive material 220 to the first substrate 204 and the absorbent particulate polymer 208 material thereon. The second printing unit 254 may include a second auxiliary adhesive applicator 266 for applying auxiliary adhesive 218 to the second substrate 206, a second rotatable support roll 268 for receiving the second substrate 206, a second hopper 270 for holding absorbent particulate polymer material 208, a second printing roll 272 for transferring the absorbent particulate polymer material 208 from the hopper 270 to the second substrate 206, and a second thermoplastic adhesive material applicator 274 for applying thermoplastic adhesive material 220 to the second substrate 206 and the absorbent particulate polymer material 208 thereon. The first absorbent layer 214 may be combined with the second absorbent layer 216 between the first support roll 258 and the second support roll 268 to form a continuous length of absorbent cores 212. In turn, the continuous length of absorbent cores 212 may be combined with and between a continuous length of topsheet substrate 138 and a continuous length of backsheet substrate 136 to form a continuous length of chassis assemblies 302. In some configurations, the continuous length of absorbent cores 212 may be combined with and between a continuous length of topsheet substrate 138 and a discrete piece or length of backsheet substrate 136 to form a continuous length of chassis assemblies 302. In some configurations, the continuous length of absorbent cores 212 may be combined with and between a continuous length of backsheet substrate 136 and a discrete piece or length of topsheet substrate 138 to form a continuous length of chassis assemblies 302.

Referring now to FIGS. 4, 5C, and 5D1, the continuous length of chassis assemblies 302 advance to cutting apparatus 306 and is cut into discrete chassis 102, each having a discrete absorbent core 202. In turn, the discrete chassis 102 are transferred to a carrier apparatus 308. As previously discussed, each discrete chassis 102 may be cut to define a longitudinal length L, wherein the absorbent core 202 defines the same longitudinal length, L. It is also to be appreciated that the absorbent material 208 may be intermittently applied in the machine direction MD between the first substrate 204 and the second substrate 206. As such, the absorbent material 208 may extend for a length that is less than the longitudinal length L.

Figure 4C:
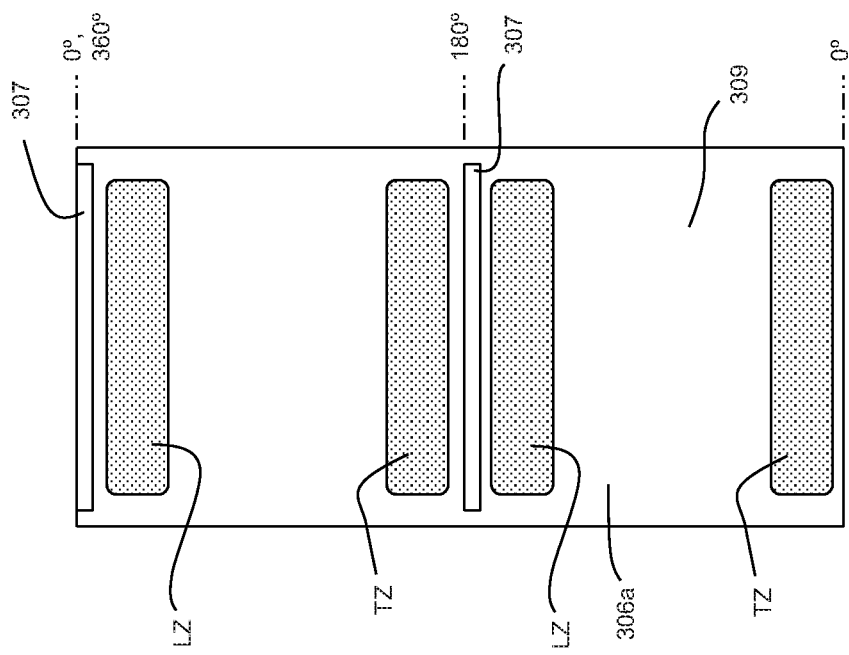
FIG. 4C is a view of an outer circumferential surface of a knife roll laid out flat.
Figure 4B:
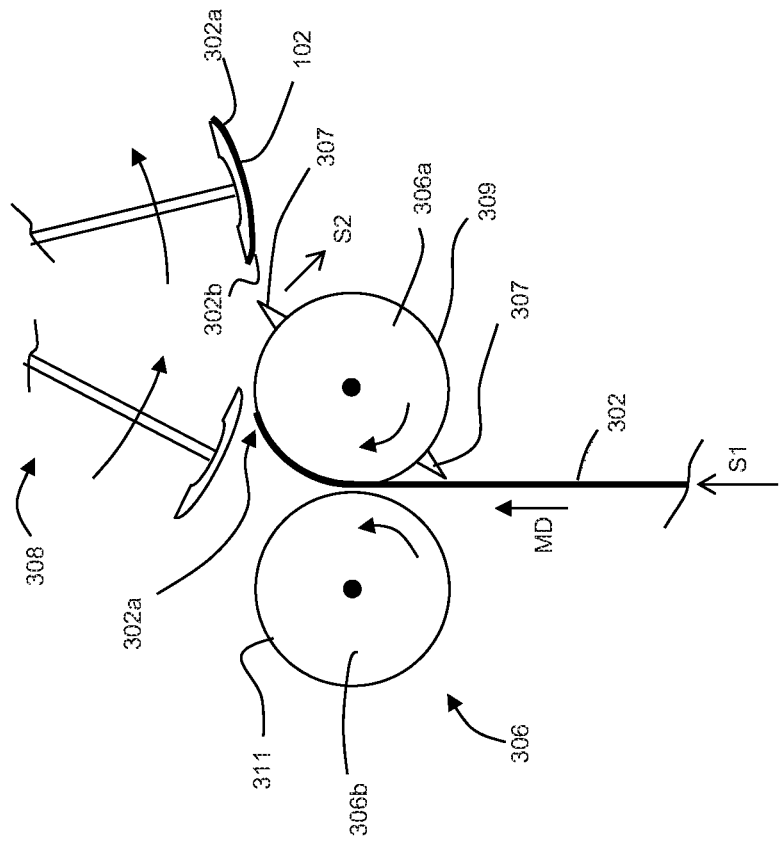
FIG. 4B is detailed view of a cutting apparatus configured to cut discrete chassis from a continuous length of chassis assemblies.

It is to be appreciated that the cutting apparatus 306 may be configured in various ways. FIG. 4B shows an example of a cutting apparatus 306 configured to cut discrete chassis 102 from the advancing continuous length of chassis assemblies 302, wherein the discrete chassis are transferred to the carrier apparatus 308. In particular, the cutting apparatus may include a knife roll 306a positioned adjacent an anvil roll 306b, wherein the knife roll 306a and anvil roll 306b rotate in opposite directions. The continuous length of chassis assemblies 302 may advance in a machine direction MD at a speed S1 between the knife roll 306a and anvil roll 306b. In turn, cutting edges or blades 307 on the knife roll 306a press the continuous length of chassis assemblies 302 against an outer surface of the anvil roll 306b to cut and separate a discrete chassis 102 from the continuous length of chassis assemblies 302. The knife roll 306a may be configured to rotate such that blades 307 advance at a speed S2.

It is to be appreciated that the cutting apparatus 306 may be configured to rotate the knife roll 306a at various different angular velocities such that the blades 307 may advance at various different speeds S2 relative the advancement speed S1 of the continuous length of chassis assemblies 302. In turn, the cutting apparatus 306 may be configured to cut discrete chassis 102 of various different longitudinal lengths L. For example, the cutting apparatus 306 may operate in a first configuration such that blades 307 advance a first speed S2a to cut discrete chassis 102 having a first longitudinal length L1 from the continuous length of chassis assemblies 302 advancing at a speed S1. The cutting apparatus 306 may also operate in a second configuration such that blades 307 advance a second speed S2a to cut discrete chassis 102 having a second longitudinal length L2 from the continuous length of chassis assemblies 302 advancing at the speed S1. As such, when the second speed S2b of the blades 307 is greater than the first speed S2a, the second longitudinal length L2 of the chassis 102 will be less than the first longitudinal length L1. Thus, the same cutting apparatus 306 may be used to cut different sized chassis 102 without having to replace the cutting apparatus 306.

It is to be appreciated that the continuous length of chassis assemblies 302 may be elastic and may be maintained in a stretched condition in the machine direction MD during and/or after cutting the discrete chassis 102 therefrom. As such, the knife roll 306a may include an outer surface 309 configured in various ways to maintain the stretched condition of the continuous length of chassis assemblies 302 and/or discrete chassis 102 during operation. For example, FIG. 4C is a view of an outer circumferential surface 309 of a knife roll 306a laid out flat including a leading zone LZ and a trailing zone TZ. The leading zone LZ is adapted to grip a leading end region of the continuous length of chassis assemblies 302 and discrete chassis 102, and the trailing zone TZ is adapted to grip a trailing end region of discrete chassis 102. As such, the leading zone LZ and the trailing zone TZ are configured to hold and maintain the machine direction stretch of the continuous length of chassis assemblies 302 and discrete chassis 102. In some configurations, the knife roll 306a may be connected with a vacuum system to that applies relatively high vacuum pressure to the leading zone LZ to help grip a leading end region 302a of the advancing chassis assemblies 302 and/or the discrete chassis 102. In some configurations, the knife roll 306a may be connected with a vacuum system to that applies relatively high vacuum pressure to the trailing zone TZ to help grip a trailing end region 302b of the discrete chassis 102 cut from the chassis assemblies 302. In some configurations, the trailing zone TZ and/or the leading zone LZ may be defined by a region on the outer circumferential surface 309 having a relatively high frictional force to help grip the leading end region 302a and/or the trailing end region 302b.

As discussed above, the cutting apparatus 306 may be configured such that the continuous length of chassis assemblies 302 may be partially wrapped onto the outer circumferential surface 309 of the knife roll 306a during the cutting operation. It should also to be appreciated that the cutting apparatus 306 may be configured such that the continuous length of chassis assemblies 302 may be partially wrapped onto an outer circumferential surface 311 of the anvil roll 306b during the cutting operation. As such, the outer circumferential surface 311 of the anvil roll 306b may be configured with a trailing zone TZ and a leading zone LZ adapted to grip the continuous length of chassis assemblies 302 and/or discrete chassis 102 such as described above.

As shown in FIGS. 4 and 5D1, after the discrete absorbent chassis 102 are cut by the cutting apparatus 306, the carrier apparatus 308 rotates and advances the discrete chassis 102 in the machine direction MD in the orientation shown in FIG. 5D1. While the chassis 102 shown in FIG. 5D1 is shown with the second laterally extending end edge 146 as a leading edge and the first laterally extending end edge 144 as the trailing edge, it is to be appreciated that in other embodiments, the chassis 102 may be advanced in other orientations. For example, the chassis may be oriented such that the second laterally extending end edge 146 is a trailing edge and the first laterally extending end edge 144 is a leading edge. The carrier apparatus 308 also rotates while at the same time changing the orientation of the advancing chassis 102. In changing the chassis orientation, the carrier apparatus 308 may turn each chassis 102 such that the lateral axis 126 of the chassis 102 is parallel or generally parallel with the machine direction MD, such as shown in FIG. 5D2. The carrier apparatus 308 may also change the speed at which the chassis 102 advances in the machine direction MD to a different speed. FIG. 5D2 shows the orientation of the chassis 102 on the carrier apparatus 308 while advancing in the machine direction MD. More particularly, FIG. 5D2 shows the chassis 102 with the lateral axis 126 of the chassis 102 generally parallel with the machine direction MD, and wherein the second longitudinal side edge 130 is the leading edge and the first longitudinal side edge 128 is the trailing edge. It is to be appreciated that various forms of carrier apparatuses may be used with the methods herein, such as for example, the carrier apparatuses disclosed in U.S. Pat. No. 7,587,966 and U.S. Patent Publication Nos. 2013/0270065 A1; 2013/0270069 A1; 2013/0270066 A1; and 2013/0270067 A1. In some embodiments, the carrier apparatus 308 may rotate at a variable angular velocity that may be changed or adjusted by a controller in order to change the relative placement of the chassis 102 and the advancing belt laminates 406, 408.

As discussed below with reference to FIGS. 4, 5E1, 5E2, 5F, and 5G, the discrete chassis 102 are transferred from the carrier apparatus 308 and combined with advancing, continuous lengths of belt laminates 406, 408, which are subsequently cut to form first and second elastic belts 106, 108 on diapers 100.

As shown in FIGS. 4, 5B, 5E1, and 5E2, the chassis 102 are transferred from the carrier apparatus 308 to a nip 316 between the carrier apparatus 308 and a roll 318 where the chassis 102 is combined with continuous lengths of advancing first belt 406 and second belt 408. The first belt laminate 406 and the second belt laminate material 408 each include a wearer facing surface 312 and an opposing garment facing surface 314. As such, the second surface 162b of the outer layer belt substrate 162 may define some or all the garment facing surface 314, and the second surface 164b of the inner layer belt substrate 164 may define some or all the wearer facing surface 312. The wearer facing surface 312 of the first belt laminate 406 may be combined with the garment facing surface 134 of the chassis 102 along the first waist region 116, and the wearer facing surface 312 of the second belt laminate 408 may be combined with the garment facing surface 134 of the chassis 102 along the second waist region 118. As shown in FIG. 4, adhesive 320 may be intermittently applied to the wearer facing surface 312 of the first and second belt laminates 406, 408 before combining with the discrete chassis 102 at the nip 316 between roll 318 and the carrier apparatus 308.

As shown in FIG. 4, the combined chassis 102, first belt laminate 406, and second belt laminate 408 advances from the nip 316 to an edge transformation apparatus 331. In some configurations, the edge transformation apparatus 331 may be configured as a folding apparatus that operates to fold the first and/or second belt laminates 406, 408 in the cross direction CD along a fold line that extends along the machine direction MD. For example, as shown in FIGS. 5E1 and 5E2, the edge transformation apparatus 331 operates to fold the outer belt substrate 162 on both belt laminates 406, 408 longitudinally to position a portion of the first surface 162a of the outer belt substrate 162 in a facing relationship with the second surface 164b of the inner belt substrate 164. As such, the edge transformation apparatus 331 creates a first fold line 169a in the first belt laminate 406 that extends in the machine direction MD. The edge transformation apparatus 331 also creates a second fold line 169b in the second belt laminate 408 that extends in the machine direction MD. In turn, the first fold line 169a defines an outer longitudinal edge 107a of the first belt laminate 406, and the second fold line 169b defines an outer longitudinal edge 109a of the second belt laminate 408.

As shown in FIG. 5E2, the folded portion of the first belt laminate 406 that extends between the first outer longitudinal edge 163a and the first fold line 169a defines a first sealing layer 210a having a width Wza in the cross direction CD. And the folded portion of the second belt laminate 408 that extends between the second outer longitudinal edge 163b and the second fold line 169b defines a second sealing layer 210b having a width Wzb in the cross direction CD. With reference to FIGS. 5E1 and 5E2, as the first and second belt laminates are folded by the edge transformation apparatus 331, the width W1 of the first belt laminate 406 is reduced to width W1a extending between the inner longitudinal edge 107b and the outer longitudinal edge 107a or first fold line 169a. And the width W2 of the second belt laminate 408 is reduced to width W2a extending between the inner longitudinal edge 109b and the outer longitudinal edge 109a or second fold line 169b.

As shown in FIG. 5E2, the sealing layers 210a, 210b are folded so as to overlap the first and/or second laterally extending end edges 144, 146 of each chassis 102. As previously discussed, the front edge 148 of the absorbent core 202 may also be coextensive with the first laterally extending end edge 144 of the chassis 102, and the back edge 150 of the absorbent core 202 may also be coextensive with the second laterally extending end edge 146 of the chassis 102. As such, the outer belt substrate 162 may be folded to create the first and/or second sealing layers 210a, 210b by positioning a portion of the first surface 162a of the outer belt substrate 162 in a facing relationship with the wearer facing surfaces 132 and/or topsheets 138 of each chassis 102. In turn, the sealing layers 210 created by positioning the first surface 162a of the outer substrate 162 in a facing relationship with the topsheets 138 of each chassis 102 such that end regions of each topsheet 138, backsheet 136, and absorbent core 202 are positioned between the sealing layers 210 and the second surface 164b of the inner substrate 164 functions to seal opposing end regions of the absorbent cores 202. It is to be appreciated that adhesive may also be applied to sealing layers 210 and/or the opposing end regions of the topsheets 138 and the second surface 164b of the inner substrate 164. In some configurations, the sealing layers 210, the opposing end regions of the topsheets 138, and the second surface 164b of the inner substrate 164 may be mechanically bonding together, such as for example, by applying at least one of ultrasonic energy, heat, and pressure to the sealing layers 210, the topsheet 138, the backsheet 136, the absorbent core 202, and the inner substrate 164.

It is to be appreciated that the edge transformation apparatus 331 may be configured in various ways to perform various operations and create the sealing layers 210. For example, as shown in FIG. 5E1A, the edge transformation apparatus 331 may be configured as a cutting apparatus that operates to cut, trim, and/or separate strips of material 171a, 171b from the first and/or second belt laminates 406, 408 along cut lines 173a, 173b that extend along the machine direction MD. In turn, the cut line 173a defines an outer longitudinal edge 107a of the first belt laminate 406, and the cut line 173b defines an outer longitudinal edge 109a of the second belt laminate 408. As the first and second belt laminates are cut or trimmed by the edge transformation apparatus 331, the width W1 of the first belt laminate 406 is reduced to width W1a extending between the inner longitudinal edge 107b and the outer longitudinal edge 107a or first cut line 173a. And the width W2 of the second belt laminate 408 is reduced to width W2a extending between the inner longitudinal edge 109b and the outer longitudinal edge 109a or second cut line 173b.

As shown in FIGS. 5E1A and 5E2A, the first strip of material 171a may be utilized as a first sealing layer 210a, and the second strip of material 171b may be utilized as a second sealing layer 210b. In turn, the sealing layers 210 may be positioned across the topsheets 138 of each chassis 102 such that end regions of each topsheet 138, backsheet 136, and absorbent core 202 are positioned between the sealing layers 210 and the second surface 164b of the inner substrate 164. As such, the sealing layers 210 function to seal opposing end regions of the absorbent cores 202. Adhesive may also be applied to sealing layers 210 and/or the opposing end regions of the topsheets 138 and the second surface 164b of the inner substrate 164. In addition, the sealing layers 210, the opposing end regions of the topsheets 138, and the second surface 164b of the inner substrate 164 may be mechanically bonding together, such as for example, by applying at least one of ultrasonic energy, heat, and pressure to the sealing layers 210, the topsheet 138, the backsheet 136, the absorbent core 202, and the inner substrate 164. It is to be appreciated that the first strip of material 171a and/or the second strip of material 171b may be cut into discrete lengths before being bonded to the chassis 102 and belt laminates 406, 408 as discussed above.

Although the edge transformation apparatus 331 is depicted in FIG. 4 and described above as being positioned downstream of the nip 316 where the chassis 102 are combined with the first and second belt laminates 406, 408, it is to be appreciated that the edge transformation apparatus 331 may be positioned in various other locations of the process and apparatus 300. For example, in some embodiments, the edge transformation mechanism 331 may be located upstream of the nip 316. As such, the edge transformation mechanism 331 may be configured to the cut the first and second belt laminates 406, 408 before being combined with the chassis 102. In another example, the edge transformation mechanism 331 may be located upstream of the nip 316 and the cutter 506. As such, the edge transformation mechanism 331 may be configured to the cut the belt laminate 402 along the first and/or second edges 163a, 163b before being slit into the first and second belt laminates 406, 408 with the cutter 506. It is also to be appreciated that some embodiments of the apparatuses and methods herein may be configured to swap the cross directional CD orientation of the advancing first and second belt laminates 406, 408 such that the folded or cut edges of the first and second belt laminates are repositioned to define the inner belt edges 107b, 109b, as opposed to the outer belt edges 107a, 109a.

Referring back to FIGS. 4, 5E1, and 5E2 a continuous length of absorbent articles 400 are defined by multiple discrete chassis 102 spaced from each other along the machine direction MD and connected with each other by the second belt laminate 408 and the first belt laminate 406. As shown in FIG. 4, the continuous length of absorbent articles 400 advances from the edge transformation apparatus 331 to a folding apparatus 332. At the folding apparatus 332, each chassis 102 is folded in the cross direction CD parallel to or along a lateral axis 126 to place the first waist region 116, and specifically, the inner, body facing surface 132 into a facing, surface to surface orientation with the inner, body surface 132 of the second waist region 118. The folding of the chassis also positions the wearer facing surface 312 of the second belt laminate 408 extending between each chassis 102 in a facing relationship with the wearer facing surface 312 of the first belt laminate 406 extending between each chassis 102.

Figure 5F:
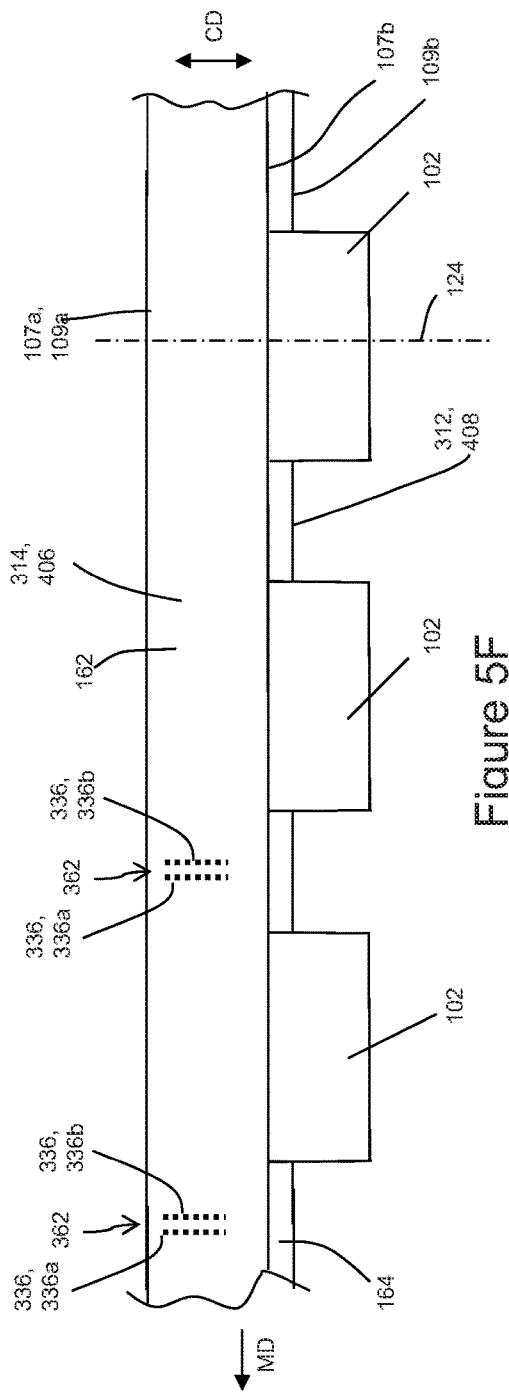
FIG. 5F is a view of folded multiple discrete chassis with the first and second elastic belt laminates in a facing relationship from FIG. 4 taken along line F-F.

As shown in FIGS. 4 and 5F, the folded discrete chassis 102 connected with the first and second belt laminates 406, 408 are advanced from the folding apparatus 332 to a bonder apparatus 334. The bonder apparatus 334 operates to bond an overlap area 362, thus creating discrete bonds 336a, 336b. The overlap area 362 includes a portion of the second belt laminate 408 extending between each chassis 102 and a portion of the first belt laminate 406 extending between each chassis 102. It is to be appreciated that the bonder apparatus 334 may be configured in various ways to create bonds 336a, 336b in various ways, such as for example with heat, adhesives, pressure, and/or ultrasonics. It is also to be appreciated that in some embodiments, the apparatus 300 may also be configured to refastenably bond the overlap area 362, in addition to or as opposed to permanently bonding the overlap area 362. Thus, the discrete bonds 336a, 336b may be configured to be refastenable, such as with hooks and loops.

Figure 5G:
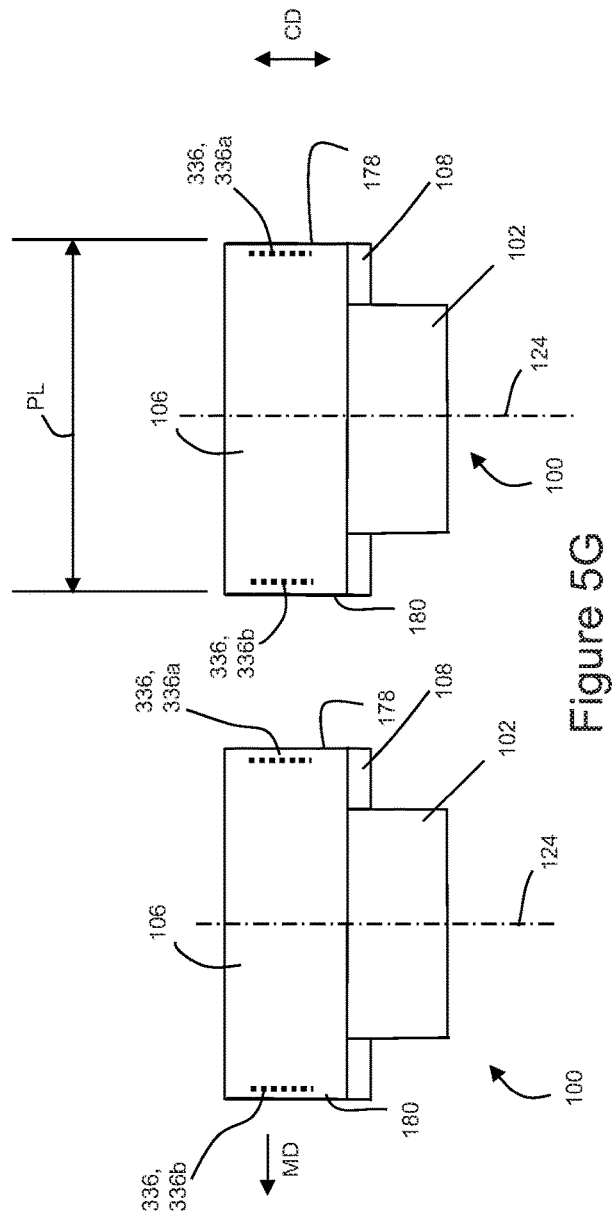
FIG. 5G is a view of two discrete absorbent articles advancing the machine direction MD from FIG. 4 taken along line G-G.

Referring now to FIGS. 4 and 5G, the continuous length of absorbent articles 400 are advanced from the bonder 334 to a cutting apparatus 338 where the first belt laminate 406 and the second belt laminate 408 are cut along the cross direction CD between adjacent bonds 336a, 336b to create discrete absorbent articles 100. As shown in FIG. 5G, the first belt laminate 406 and the second belt laminate 408 are cut into discrete pieces to form the first and second elastic belts 106, 108, each having a pitch length, PL, extending along the machine direction MD. As such, bond 336a may correspond with and form a first side seam 178 on an absorbent article 100, and the bond 336b may correspond with and form a second side seam 180 on a subsequently advancing absorbent article.

Figure 6A:
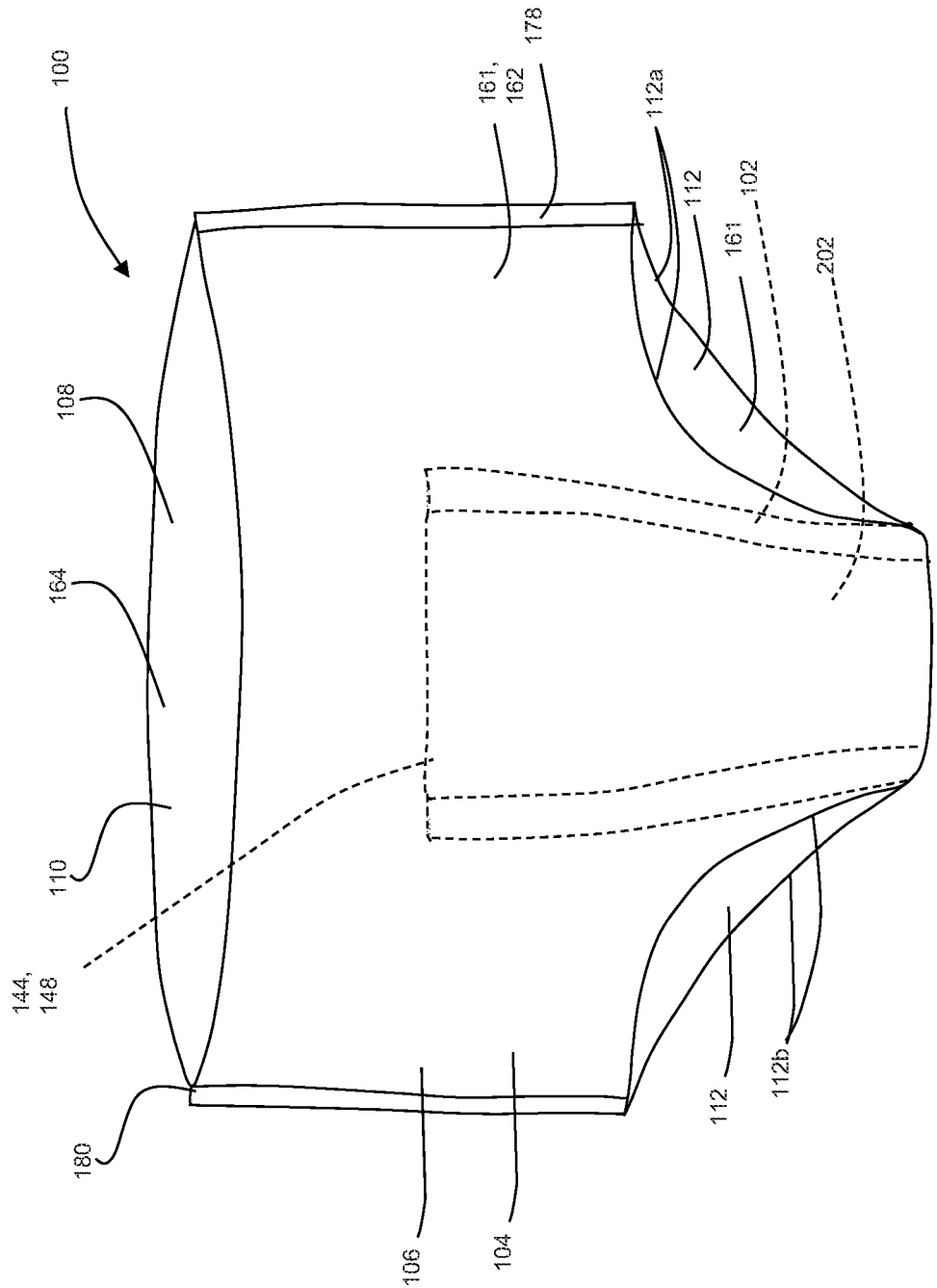
FIG. 6A is a front perspective view of a diaper pant constructed with a contiguous outer cover.

It is to be appreciated that the processes and apparatuses herein may be configured to manufacture various types of diaper pants discussed above. In some embodiments, the diaper pants 100 may include a chassis 102 and elastic belts 106, 108 configured in different ways other than as depicted in FIGS. 1A-2B. For example, FIGS. 6A-7 show a diaper pant 100 having many of the same components as described above with reference to FIGS. 1A-2B, except the outer layer 162 of the elastic belts 106, 108 is configured as a contiguous outer cover 161 that extends through the first waist region 116, crotch region 119, and second waist region 118. Thus, as shown in FIG. 7, the outer cover 161 also includes a first waist end region 116, a crotch region 119, and an opposing second waist end region 118. The outer cover 161 also includes a garment facing surface 162b and an opposing wearer facing surface 162a. As such, elastic members 168 of the elastic belts 106, 108 may be connected with the wearer facing surface 162a of the outer cover 161. And the chassis 102 may be positioned on the wearer facing surface 162a of the outer cover 161. As such, the backsheet 136 may include a portion of the outer cover 161. In some configurations, the backsheet 136 of the chassis 102 may comprise a film substrate and the outer cover 161 may comprise a nonwoven substrate.

In addition, the outer cover 161 may include a first longitudinal side edge 128a and a second longitudinal side edge 130a that are positioned laterally outboard the first longitudinal side edge 128 of the chassis 102 and second longitudinal side edge 130 of the chassis 102, respectively, as shown in FIG. 7. As shown in FIGS. 6A and 7, the first longitudinal side edge 128a may define the perimeter 112a of one leg opening 112, and the second longitudinal side edge 130a may define the perimeter 112b of the other leg opening 112. It is to be appreciated also that the first longitudinal side edge 128a and a second longitudinal side edge 130a may aligned with or positioned laterally inboard of the first longitudinal side edge 128 of the chassis 102 and second longitudinal side edge 130 of the chassis 102, respectively. As such, in some embodiments, the perimeter 112a of one leg opening 112 may be defined by portions of the first longitudinal edges 128, 128a, and the perimeter 112b of the other leg opening may be defined by portions of the second longitudinal edges 130, 130a.

FIG. 6B shows a front plan view of a diaper pant 100 in a laid flat condition illustrating various regions of the diaper pant 100. And 6C shows a rear plan view of the diaper pant 100 in a laid flat condition illustrating various regions of the diaper pant 100. As discussed above, the diaper pant 100 defines include an inner, body facing surface 132, and an outer, garment facing surface 134. The diaper pant 100 also includes a crotch end 190 that is defined by a lateral fold line 192 in the crotch region 119. As such, the lateral fold line 192 divides the crotch region into a first crotch region 119a and a second crotch region 119b.

Figure 6C:
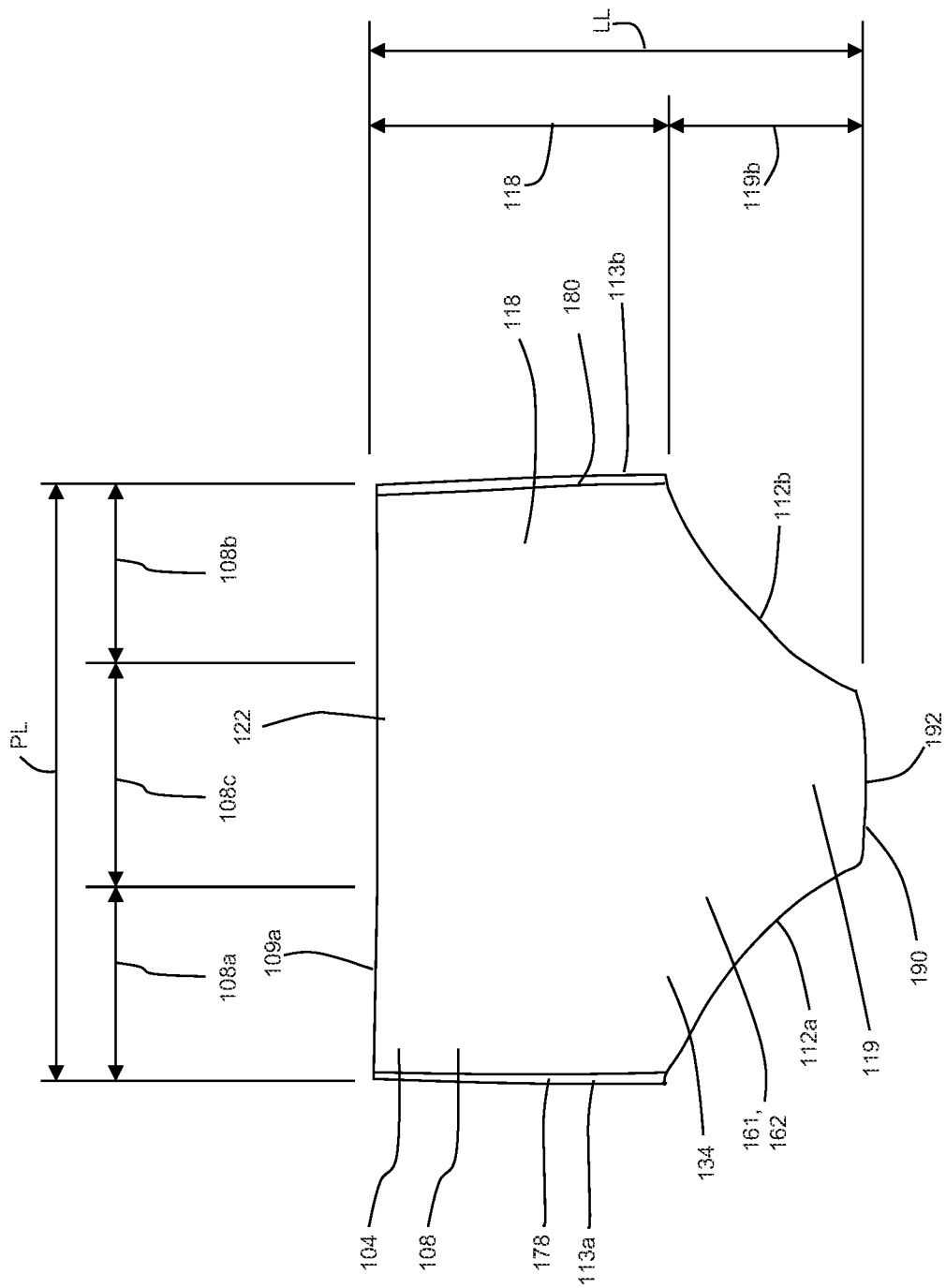
FIG. 6C is a rear plan view of the diaper pant of FIG. 6A.

The diaper pant 100 is shown in FIGS. 6A-6C as having a first elastic belt 106, and a second elastic belt 108. The first belt 106 has a first end region 106a, an opposing second end region 106b, and a central region 106c. And the second belt 108 has a first end region 108a, an opposing second end region 108b, and a central region 108c. The first end regions 106a, 108a are connected together at a first side seam 178, and the second end regions are 106b, 108b are connected together at a second side seam 180. As shown in FIGS. 6B and 6C, the distance between the first longitudinal side edge 111a and the second longitudinal side edge 111b defines the pitch length, PL, of the first elastic belt 106, and the distance between the first longitudinal side edge 113a and the second longitudinal side edge 113b defines the pitch length, PL, of the second elastic belt 108.

The first end region 106a the first belt 106 may extend approximately 20% to 40% of the pitch length PL of the diaper pant 100 in an assembled, laid-flat, relaxed condition, and the first end region 108a the second belt 108 may extend approximately 20% to 40% of the pitch length PL of the diaper pant 100 in an assembled, laid-flat, relaxed condition. The second end region 106b the first belt 106 may extend approximately 20% to 40% of the pitch length PL of the diaper pant 100 in an assembled, laid-flat, relaxed condition, and the second end region 108b the second belt 108 may extend approximately 20% to 40% of the pitch length of the diaper pant 100 in an assembled, laid-flat, relaxed condition. The central region 106c the first belt 106 may extend approximately 20% to 60% of the pitch length PL of the diaper pant 100 in an assembled, laid-flat, relaxed condition, and the central region 108c the second belt 108 may extend approximately 20% to 60% of the pitch length PL of the diaper pant 100 in an assembled, laid-flat, relaxed condition.

The diaper pant 100 in FIGS. 6B and 6C is also shown as having a longitudinal length LL that is defined by the distance between the first waist edge 121 and the crotch end 190 (or the lateral fold line 192), or if longer, the distance from the second waist edge 122 to the crotch end 190 (or the lateral fold line 192). The longitudinal length LL may be measured along the longitudinal centerline 124 of the diaper pant 100. As shown in FIGS. 6B-6C, the first waist region 116 extends a distance generally in the longitudinal direction from the waist edge 121 along the side seams 178, 180 to the leg openings 112, and the second waist region 118 extends a distance generally in the longitudinal direction from the waist edge 122 along the side seams 178, 180 to the leg openings 112. Hence, a first crotch region 119a extends a distance from the crotch end 190 to the first waist region 116, and a second crotch region 119b extends a distance from the crotch end 190 to the second waist region 118. In some embodiments, the first waist region 116 and/or the second waist region 118 may extend about two-thirds the longitudinal length LL of the assembled diaper pant 100. In addition, the first crotch region 119a and/or the second crotch region 119b may extend about one-third the longitudinal length LL of the assembled diaper pant 100.

Figure 8:
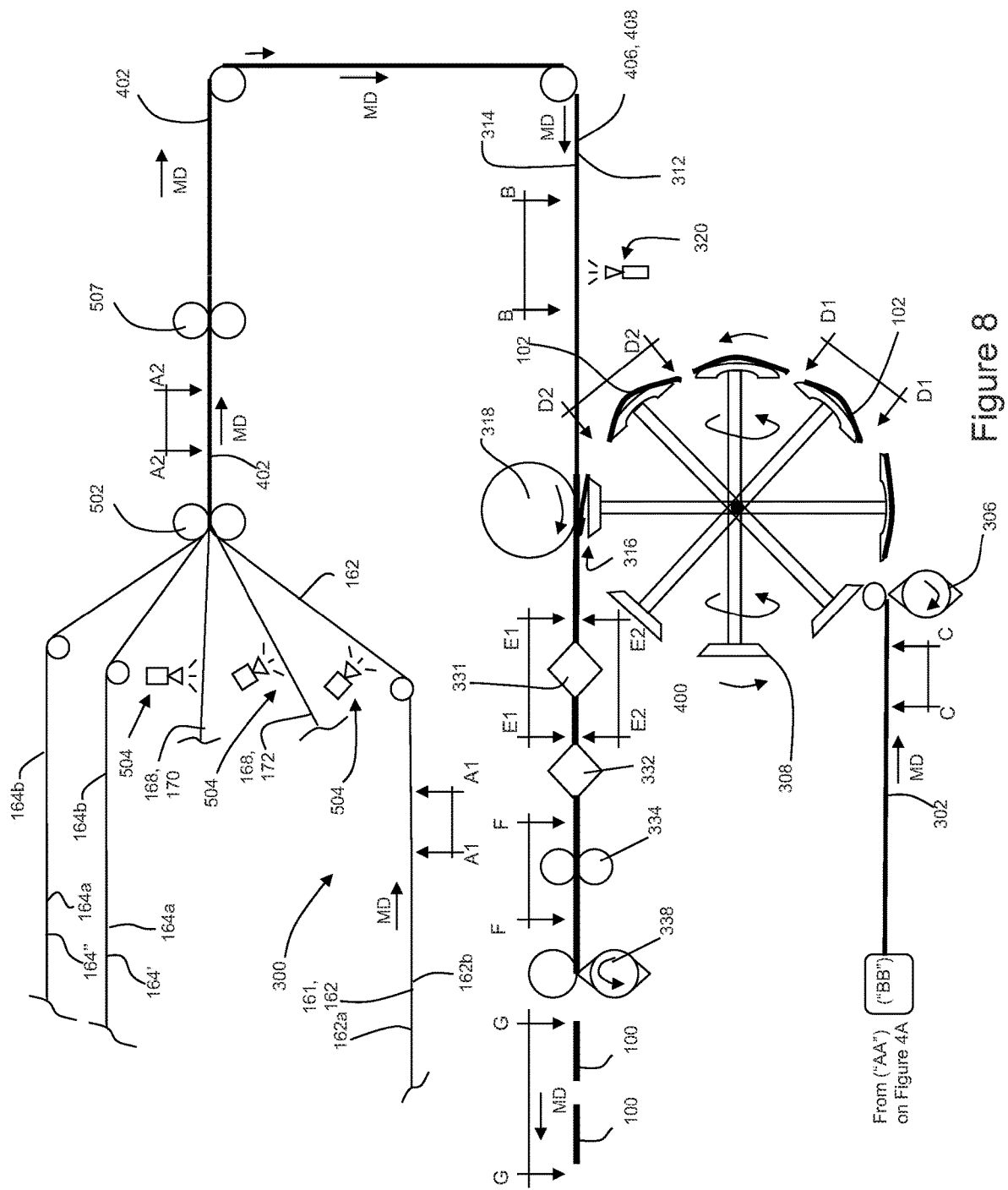
FIG. 8 is a schematic side view of a converting apparatus adapted to manufacture pre-fastened, pant diapers.
Figure 9B:
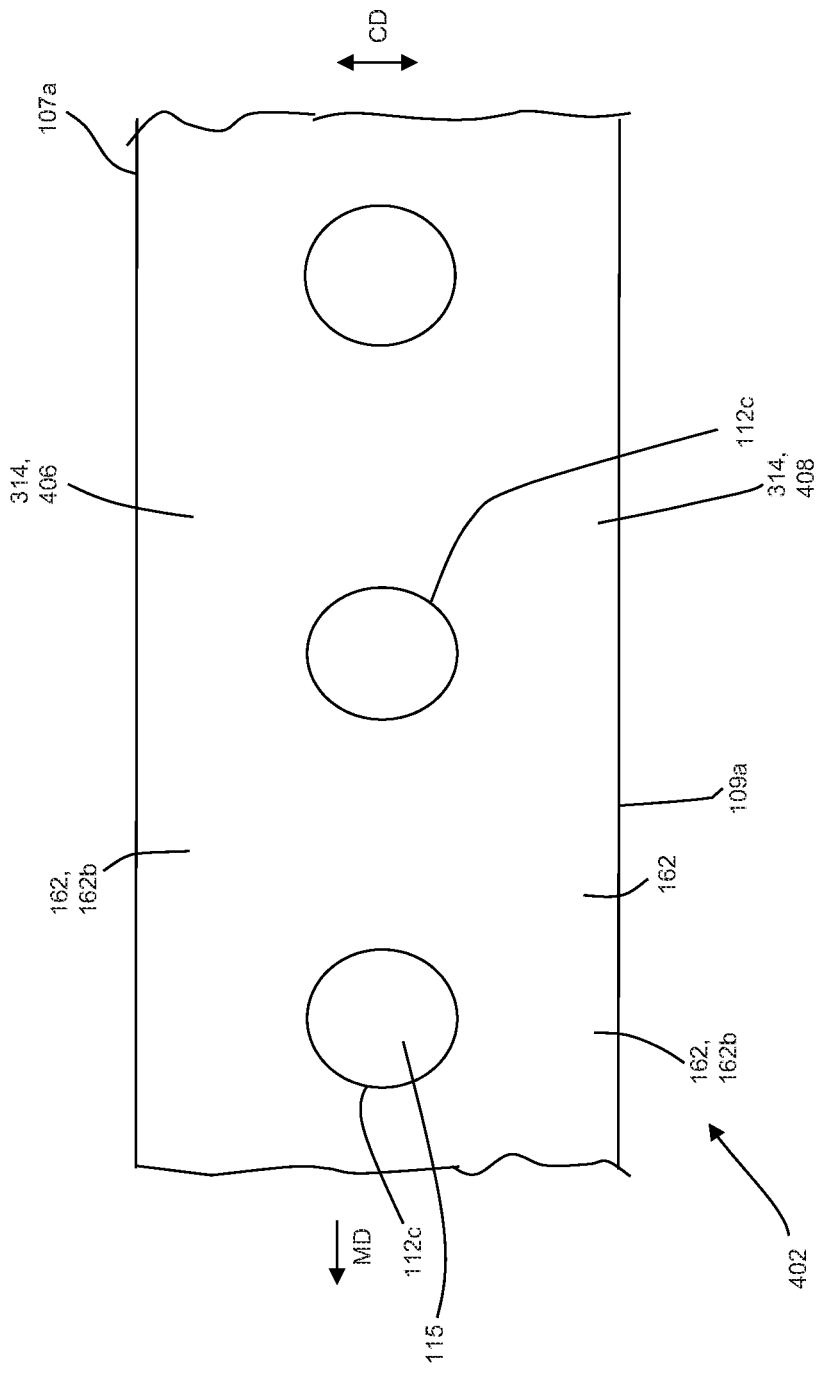
FIG. 9B is a view of continuous lengths of advancing first and second elastic belt laminates from FIG. 8 taken along line B-B.

FIG. 8 shows a converting apparatus 300 configured to assemble diaper pants such as shown in FIGS. 6A-7. As shown in FIG. 8, a first continuous substrate layer in the form of a continuous length of outer layer belt substrate 162 is combined with first and second separate continuous lengths of inner layer belt substrates 164', 164" and elastics 168 form a continuous elastic laminate 402. The outer layer belt substrate 162 also defines the outer cover 161 discussed above with reference to FIGS. 6A-7. With reference to FIGS. 8, 9A, and 9B, continuous lengths of outer layer belt substrate 162, first and second inner layers of belt substrate 164', 164", outer elastic strands 170 and inner elastic strands 172 are advanced in a machine direction MD and combined at nip rolls 502 to form the continuous elastic laminate 402.

As shown in FIGS. 8, 9A1, and 9A2, the outer belt substrate 162 includes first surface 162a and an opposing second surface 162b, and defines a width W in the cross direction between opposing longitudinal edges 163a, 163b. The first inner belt substrate 164' includes first surface 164a and an opposing second surface 164b, and defines a width in the cross direction CD between opposing first and second longitudinal edges 165a, 165b. And the second inner belt substrate 164" includes first surface 164a and an opposing second surface 164b, and defines a width in the cross direction CD between opposing first and second longitudinal edges 165a, 165b. As shown in FIG. 9A2, the width W of the outer belt substrate 162 may be greater than the widths of the inner belt substrates 164', 164". And the width W of the outer belt substrate 162 may also define the width W of the elastic laminate 402.

With continued reference to FIG. 8, before entering the nip rolls 502, the outer elastic strands 170 and inner elastic strands 172 are stretched in the machine direction MD. In addition, adhesive 504 may be applied to the elastic strands 170, 172 as well as either or both of the continuous lengths of outer layer belt substrate 162 and inner layer belt substrates 164', 164" before entering nip rolls 502. As such, the elastic strands 168 are bonded between the first surface 162a of the outer layer belt substrate 162 and the first surfaces 164a of inner layer belt substrates 164', 164" at the nip rolls 502. Further, adhesive 504 may be applied intermittently along the lengths of the inner elastic strands 172 and/or intermittently along the length of either or both of the continuous lengths of outer layer belt substrate 162 and inner layer belt substrates 164', 164" before entering nip rolls 502. As previously discussed, the inner elastic strands 172 may be intermittently bonded to either or both of the continuous lengths of outer layer belt substrate 162 and inner layer belt substrates 164', 164" along the machine direction MD. In some configurations, the apparatus 300 may be configured such that the elastic strands 168 are bonded between the second surface 162b of the outer layer belt substrate 162 and the belt substrates 164', 164" at the nip rolls 502. As such, the first and second elastic belt laminates 406, 408 may be formed on the garment facing surface of the outer cover 161.

As shown in FIGS. 8 and 9A2, the continuous elastic laminate 402 includes a first elastic belt laminate 406 and a second elastic belt laminate 408. More particularly, the combination of the outer layer belt substrate 162, the first inner layer of belt substrate 164', and elastic strands 168 defines the first belt laminate 406. And the combination of the outer layer belt substrate 162, the second inner layer of belt substrate 164", and elastic strands 168 defines the second belt laminate 408. The first belt laminate 406 includes an outer longitudinal edge 163a and an inner longitudinal edge 107b that may define a substantially constant width, W1, in the cross direction CD. The inner longitudinal edge 107b may be defined by the second longitudinal edge 165b of the first inner belt substrate 164'. The second belt laminate 408 includes an outer longitudinal edge 163b and an inner longitudinal edge 109b that may define a substantially constant width, W2, in the cross direction CD. The inner longitudinal edge 109b may be defined by the second longitudinal edge 165b of the second inner belt substrate 164". In some configurations, W2 equal to W1. It is also to be appreciated that in some configurations, W1 may be less than or greater than W2. The first belt laminate 406 is separated in the cross direction from the second belt laminate 408 to define a gap between the inner longitudinal edge 107b of the first belt laminate 406 and the inner longitudinal edge 109b of the second belt laminate 408.

With continued reference to FIG. 8, from the nip rolls 502 the continuous elastic laminate 402 advances in the machine direction MD to a cutter 507 that removes material from a central region of the continuous elastic laminate 402 to form holes 115 defined by perimeter edges 112c, such as shown in FIG. 9B. The perimeter edges 112c may define all or portions of the perimeters 112a, 112b of the leg openings 112 mentioned above and shown in FIG. 6A. It is to be appreciated that the cutter may be configured to remove material from only the outer layer belt substrate 162. In some configurations, the cutter 507 may be configured to remove material from the outer belt substrate 162 as well as the first inner layer belt substrate 164' and/or second inner layer belt substrate 164". The cutter 507 may also be configured as a perforator that perforates the belt material with a line of weakness and wherein the belt material is separated along the line of weakness in a later step. It is also to be appreciated that the cutter 507 may be configured to form holes 115 in the continuous elastic laminate 402 before or after the continuous elastic laminate 402 is combined with the chassis 102.

As discussed above with reference to FIGS. 4, 5C, 5D1, and 5D2, and as shown in FIG. 8, a continuous length of chassis assemblies 302 are advanced in a machine direction MD to a carrier apparatus 308 and are cut into discrete chassis 102 with cutting apparatus 306, while advancing in the orientation shown in FIG. 5D1. After the discrete absorbent chassis 102 are cut by the cutting apparatus 306, the carrier apparatus 308 rotates and advances the discrete chassis 102 in the machine direction MD in the orientation shown in FIG. 5D1. The carrier apparatus 308 also rotates while at the same time changing the orientation of the advancing chassis 102. In changing the chassis orientation, the carrier apparatus 308 may turn each chassis 102 such that the lateral axis 126 of the chassis 102 is parallel or generally parallel with the machine direction MD, such as shown in FIG. 5D2.

As shown in FIGS. 8, 9E1, and 9E2, the chassis 102 are transferred from the carrier apparatus 308 to a nip 316 between the carrier apparatus 308 and a roll 318 where the chassis 102 is combined with the continuous elastic laminate 402. The chassis 102 may be spaced apart from each other along the machine direction MD on the continuous elastic laminate 402, wherein at least one hole 115 is positioned between two consecutive chassis 102. The continuous elastic laminate 402 includes a wearer facing surface 312 and an opposing garment facing surface 314. As such, the second surface 162b of the outer layer belt substrate 162 may define the garment facing surface 314. And the first surface 162a of the outer layer belt substrate 162 and the second surfaces 164b of the inner layer belt substrates 164', 164" may define the wearer facing surface 312. The wearer facing surface 312 of the continuous elastic laminate 402 may be combined with the garment facing surface 134 of the chassis 102. As shown in FIG. 8, adhesive 320 may be intermittently applied to the wearer facing surface 312 of the continuous elastic laminate 402 before combining with the discrete chassis 102 at the nip 316 between roll 318 and the carrier apparatus 308.

As shown in FIG. 8, the combined chassis 102 and the continuous elastic laminate 402 advances from the nip 316 to an edge transformation apparatus 331. In some configurations, the edge transformation apparatus 331 may be configured as a folding apparatus that operates to fold the continuous elastic laminate 402 in the cross direction CD along a fold line that extends along the machine direction. For example, as shown in FIGS. 9E1 and 9E2, the edge transformation apparatus 331 operates to fold the outer belt substrate 162 on both belt laminates 406, 408 longitudinally to position a portion of the first surface 162a of the outer belt substrate 162 in a facing relationship with the second surfaces 164b of the first and second inner belt substrates 164', 164". As such, the edge transformation apparatus 331 creates a first fold line 169a in the outer belt substrate 162 or the first belt laminate 406 that extends in the machine direction. The edge transformation apparatus 331 also creates a second fold line 169b in the outer belt substrate 162 or the second belt laminate 408 that extends in the machine direction MD. In turn, the first fold line 169a defines an outer longitudinal edge 107a of the first belt laminate 406, and the second fold line 169b defines an outer longitudinal edge 109a of the second belt laminate 408.

As shown in FIG. 9E2, the folded portion of the outer belt substrate 162 on the first belt laminate 406 that extends between first longitudinal edge 163a and the and the first fold line 169a defines a first sealing layer 210a having a width in the cross direction CD. And the folded portion of the outer belt substrate 162 on the second belt laminate 408 that extends between second longitudinal edge 163b and the and the second fold line 169b defines a second sealing layer 210b having a width in the cross direction CD. With reference to FIGS. 9E1 and 9E2, as the outer belt substrate 162 and elastic laminate 402 are folded by the edge transformation apparatus 331, the width W of the continuous elastic laminate 402 is reduced to a width Wa extending between the outer longitudinal edge 107a (or first fold line 169a) and the outer longitudinal edge 109a (or second fold line 169b). In addition, the width W1 of the first belt laminate 406 is reduced to width W1a extending between the inner longitudinal edge 107b and the outer longitudinal edge 107a (or first fold line 169a). And the width W2 of the second belt laminate 408 is reduced to width W2a extending between the inner longitudinal edge 109b and the outer longitudinal edge 109a (or second fold line 169b).

As shown in FIG. 9E2, the sealing layers 210a, 210b are folded so as to overlap the first and/or second laterally extending end edges 144, 146 of each chassis 102. As previously discussed, the front edge 148 of the absorbent core 202 may also be coextensive with the first laterally extending end edge 144 of the chassis 102, and the back edge 150 of the absorbent core 202 may also be coextensive with the second laterally extending end edge 146 of the chassis 102. As such, the outer belt substrate 162 may be folded to create the first and/or second sealing layers 210a, 210b by positioning a portion of the first surface 162a of the outer belt substrate 162 in a facing relationship with the wearer facing surfaces 132 and/or topsheets 138 of each chassis 102. In turn, the sealing layers 210 created by positioning the first surface 162a of the outer substrate 162 in a facing relationship with the topsheets 138 of each chassis 102 such that end regions of each topsheet 138, backsheet 136, and absorbent core 202 are positioned between the sealing layers 210 and the second surfaces 164b of the first and second inner belt substrates 164', 164" function to seal opposing end regions of the absorbent cores 202. It is to be appreciated that adhesive may also be applied to sealing layers 210 and/or the opposing end regions of the topsheets 138 and the second surfaces 164b of the first and second inner belt substrates 164', 164". In some configurations, the sealing layers 210, the opposing end regions of the topsheets 138, and the second surfaces 164b of the first and second inner belt substrates 164', 164" may be mechanically bonding together, such as for example, by applying at least one of ultrasonic energy, heat, and pressure to the sealing layers 210, the topsheet 138, the backsheet 136, the absorbent core 202, and the first and second inner belt substrates 164', 164".

As discussed above, it is to be appreciated that the edge transformation apparatus 331 may be configured in various ways to perform various operations. For example, as shown in FIG. 9E1A, the edge transformation apparatus 331 may be configured as a cutting apparatus that operates to cut, trim, and/or separate strips of material 171a, 171b from the continuous elastic laminate 402 along cut lines 173a, 173b that extend along the machine direction MD. The edge transformation apparatus 331 also creates a cut line 173b in the continuous elastic laminate 402 that extends in the machine direction MD. In turn, the cut line 173a defines an outer longitudinal edge 107a of the elastic laminate 402 and first belt laminate 406, and the cut line 173b defines an outer longitudinal edge 109a of the elastic laminate 402 and the second belt laminate 408.

With continued reference to FIG. 9E1A, as the outer belt substrate 162 and elastic laminate 402 are cut or trimmed by the edge transformation apparatus 331, the width W of the continuous elastic laminate 402 is reduced to a width Wa extending between the outer longitudinal edge 107a (or first cut line 173a) and the outer longitudinal edge 109a (or second cut line 173b). In addition, the width W1 of the first belt laminate 406 is reduced to width W1a extending between the inner longitudinal edge 107b and the outer longitudinal edge 107a (or first cut line 173a). And the width W2 of the second belt laminate 408 is reduced to width W2a extending between the inner longitudinal edge 109b and the outer longitudinal edge 109a (or second cut line 173b).

As shown in FIGS. 9E1A and 9E2A, the first strip of material 171a may be utilized as a first sealing layer 210a and the second strip of material 171b may be utilized as a second sealing layer 210b. In turn, the sealing layers 210 may be positioned across the topsheets 138 of each chassis 102 such that end regions of each topsheet 138, backsheet 136, and absorbent core 202 are positioned between the sealing layers 210 and the second surfaces 164b of the first and second inner belt substrates 164', 164". As such, the sealing layers 210 function to seal opposing end regions of the absorbent cores 202. Adhesive may also be applied to sealing layers 210 and/or the opposing end regions of the topsheets 138 and the second surfaces 164b of the first and second inner belt substrates 164', 164". In addition, the sealing layers 210, the opposing end regions of the topsheets 138, and the second surfaces 164b of the first and second inner belt substrates 164', 164" may be mechanically bonding together, such as for example, by applying at least one of ultrasonic energy, heat, and pressure to the sealing layers 210, the topsheet 138, the backsheet 136, the absorbent core 202, and the first and second inner belt substrates 164', 164". It is to be appreciated that the first strip of material 171a and/or the second strip of material 171b may be cut into discrete lengths before being bonded to the chassis 102 and belt laminates 406, 408 as discussed above.

Although the edge transformation apparatus 331 is depicted in FIG. 8 and described above as being positioned downstream of the nip 316 where the chassis 102 are combined with the first and second belt laminates 406, 408, it is to be appreciated that the edge transformation apparatus 331 may be positioned in various other locations of the process and apparatus 300. For example, in some embodiments, the edge transformation mechanism 331 may be located upstream of the nip 316. As such, the edge transformation mechanism 331 may be configured to cut the continuous elastic laminate 402 before being combined with the chassis 102. In another example, the edge transformation mechanism 331 may be located upstream of the nip 316 the cutter 507. As such, the edge transformation mechanism 331 may be configured to cut the elastic laminate 402 along the first and/or second edges 163a, 163b before the cutter 507 removes material from a central region of the continuous elastic laminate 402 to form holes 115.

With continued reference to FIGS. 8, 9E1, and 9E2, a continuous length of absorbent articles 400 are defined by multiple discrete chassis 102 spaced from each other along the machine direction MD and connected with each other by the continuous elastic laminate 402. As shown in FIG. 8, the continuous length of absorbent articles 400 advances from the nip 316 to a folding apparatus 332. At the folding apparatus 332, the continuous elastic laminate 402 and each chassis 102 are folded in the cross direction CD parallel to or along a lateral axis 126 to place the first waist region 116, and specifically, the inner, body facing surface 132 into a facing, surface to surface orientation with the inner, body surface 132 of the second waist region 118. The folding operation creates the lateral fold line 192 that defines the crotch end 190 discussed above with reference to FIGS. 6B and 6C. The folding of the chassis also positions the wearer facing surface 312 of the second belt laminate 408 extending between each chassis 102 in a facing relationship with the wearer facing surface 312 of the first belt laminate 406 extending between each chassis 102.

As shown in FIGS. 8 and 9F, the folded continuous length of absorbent articles 400 are advanced from the folding apparatus 332 to a bonder apparatus 334. The bonder apparatus 334 operates to bond an overlap area 362, thus creating discrete bonds 336a, 336b. The overlap area 362 includes a portion of the second belt laminate 408 extending between each chassis 102 and a portion of the first belt laminate 406 extending between each chassis 102. It is to be appreciated that the bonder apparatus 334 may be configured in various ways to create bonds 336a, 336b in various ways, such as for example with heat, adhesives, pressure, and/or ultrasonics. It is also to be appreciated that in some embodiments, the apparatus 300 may be configured to also refastenably bond the overlap area 362, in addition to or as opposed to permanently bonding the overlap area 362. Thus, the discrete bonds 336a, 336b may be configured to be refastenable, such as with hooks and loops.

Referring now to FIGS. 8 and 9G, the continuous length of absorbent articles 400 are advanced from the bonder 334 to a cutting apparatus 338 where the first belt laminate 406 and the second belt laminate 408 are cut along the cross direction CD between adjacent bonds 336a, 336b to create discrete absorbent articles 100. As shown in FIG. 9G, the continuous length of absorbent articles 400 are cut into discrete pieces to form the first and second elastic belts 106, 108, each having a pitch length, PL, extending along the machine direction MD and longitudinal length LL extending in the cross direction CD. As such, bond 336a may correspond with and form a first side seam 178 on an absorbent article 100, and the bond 336b may correspond with and form a second side seam 180 on a subsequently advancing absorbent article.

This application claims the benefit of U.S. Provisional Application No. 62/436,053, filed on Dec. 19, 2016, the entirety of which is incorporated by reference herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for assembling disposable diaper pants, the method comprising the steps of:
   advancing a first continuous elastic laminate in a machine direction, the first continuous elastic laminate comprising an outer substrate comprising a first surface and an opposing second surface, an inner substrate comprising a first surface and an opposing second surface, and elastic material bonded between the first surfaces of the inner and outer substrates;
   advancing a second continuous elastic laminate in the machine direction;
   advancing a first continuous substrate, the first continuous substrate having a first surface and an opposing second surface, and defining a width in a cross direction;
   depositing absorbent material on the first continuous substrate;
   advancing a second continuous substrate in the machine direction;
   combining the first continuous substrate and the second continuous substrate with the absorbent material positioned between the first continuous substrate and the second continuous substrate to form a continuous length of absorbent cores;
   bonding the continuous length of absorbent cores between a continuous topsheet substrate and a continuous backsheet substrate;
   combining leg cuffs with at least one of the continuous topsheet substrate and the continuous backsheet substrate;

cutting the continuous topsheet substrate, the continuous backsheet substrate, and the continuous length of absorbent cores together along the cross direction to create discrete chassis, each chassis comprising a topsheet, a backsheet, and an absorbent core disposed between the topsheet and the backsheet, wherein the topsheet, the backsheet, and the absorbent core each comprise a first end region and an opposing second end region separated from each other by a central region, and comprising a longitudinal axis and a lateral axis, wherein the longitudinal axis is parallel with the machine direction, wherein the topsheet, the backsheet, and the absorbent core have equal longitudinal lengths, L;

depositing the discrete chassis spaced apart from each other along the machine direction onto the first continuous elastic laminate and the second continuous elastic laminate; and sealing the first end regions of the absorbent cores by folding a portion of the first continuous elastic laminate into a facing relationship with the topsheets of each chassis, wherein first end regions of each topsheet, backsheet, and absorbent core are positioned between the folded portion of the first continuous elastic laminate and the second surface of the inner substrate.

2. The method of claim 1, wherein the step of sealing the first end regions of the absorbent cores further comprising folding a portion of the outer substrate longitudinally to position the first surface of the outer substrate into a facing relationship with the topsheets of each chassis, wherein first end regions of each topsheet, backsheet, and absorbent core are positioned between the folded portion of the outer substrate and the second surface of the inner substrate.

3. The method of claim 2, wherein the step of sealing the first end regions of the absorbent cores further comprises applying adhesive to the first surface of the outer substrate.

4. The method of claim 2, wherein the step of sealing the first end regions of the absorbent cores further comprises mechanically bonding the folded portion of the outer substrate, the topsheet, the backsheet, the absorbent core, and the inner substrate together.

5. The method of claim 4, wherein the step of mechanically bonding further comprises applying at least one of ultrasonic energy, heat, and pressure to the folded portion of the outer substrate, the topsheet, the backsheet, the absorbent core, and the inner substrate.

6. The method of claim 1, wherein the absorbent material comprises absorbent particulate polymer material.

7. The method of claim 1, wherein the absorbent material extends for a longitudinal length that is less than the longitudinal length, L, of the absorbent core.

8. The method of claim 1, further comprising the step of combining a liquid acquisition layer with the continuous topsheet substrate, wherein the liquid acquisition layer is positioned between the continuous length of absorbent cores and the continuous top sheet substrate.

9. The method of claim 1, further comprising the step of turning each chassis such that the lateral axis is parallel with the machine direction.

10. The method of claim 1, further comprising the steps of:
folding each chassis along the lateral axis to position the first continuous elastic laminate into a facing relationship with the second continuous elastic laminate; and
cutting the first and second continuous elastic laminates in the cross direction to form discrete diaper pants.

11. The method of claim 1, further comprising the steps of:
bonding elastic material between the first surface of the inner substrate and the first surface of the outer substrate to form an elastic laminate; and
cutting the elastic laminate along the machine direction to form the first continuous elastic laminate and the second continuous elastic laminate.

12. A method for assembling disposable diaper pants, the method comprising the steps of:
advancing a continuous elastic laminate in a machine direction, the continuous elastic laminate comprising an outer substrate comprising a first surface and an opposing second surface, an inner substrate comprising a first surface and an opposing second surface, and elastic material bonded between the first surfaces of the inner and outer substrates;
advancing a first continuous substrate, the first continuous substrate having a first surface and an opposing second surface, and defining a width in a cross direction;
depositing absorbent material on the first continuous substrate;
advancing a second continuous substrate in the machine direction;
combining the first continuous substrate and the second continuous substrate with the absorbent material positioned between the first continuous substrate and the second continuous substrate to form a continuous length of absorbent cores;
bonding the continuous length of absorbent cores between a continuous topsheet substrate and a continuous backsheet substrate to form a continuous length of absorbent chassis;
combining leg cuffs with at least one of the continuous topsheet substrate and the continuous backsheet substrate;
cutting the continuous topsheet substrate, the continuous backsheet substrate, and the continuous length of absorbent cores together along a cross direction to create discrete chassis, each chassis comprising a topsheet, a backsheet, and an absorbent core disposed between the topsheet and the backsheet, the topsheet, backsheet, and absorbent core each comprising a first end region and an opposing second end region separated from each other by a central region, and comprising a longitudinal axis and a lateral axis, wherein the longitudinal axis is parallel with the machine direction, wherein the topsheet, the backsheet, and the absorbent core have equal longitudinal lengths, L;
depositing the discrete chassis spaced apart from each other along the machine direction onto the continuous elastic laminate;
providing a sealing layer extending in the machine direction;
sealing the first end regions of the absorbent cores by bonding the sealing layer with the second surface of the inner substrate and the topsheets of each chassis, wherein first end regions of each topsheet, backsheet, and absorbent core are positioned between the sealing layer and the second surface of the inner substrate.

13. The method of claim 12, wherein the step of sealing the first end regions of the absorbent cores further comprises applying adhesive to the first end regions of the topsheets and the second surface of the inner substrate.

14. The method of claim 12, wherein the step of sealing the first end regions of the absorbent cores further comprises mechanically bonding the sealing layer, the topsheet, the backsheet, the absorbent core, and the inner substrate together.

15. The method of claim 14, wherein the step of mechanically bonding further comprises applying at least one of ultrasonic energy, heat, and pressure to the sealing layer, the topsheet, the backsheet, the absorbent core, and the inner substrate.

16. The method of claim 12, wherein the step of providing the sealing layer further comprises cutting a strip of material from the continuous elastic laminate longitudinally in the machine direction.

17. The method of claim 12, further comprising the steps of:
cutting the continuous elastic laminate along the machine direction to form a first continuous elastic laminate and a second continuous elastic laminate;
depositing the discrete chassis spaced apart from each other along the machine direction onto the first continuous elastic laminate and the second continuous elastic laminate;
folding each chassis along the lateral axis to position the first continuous elastic laminate into a facing relationship with the second continuous elastic laminate; and
cutting the first and second continuous elastic laminates in the cross direction to form discrete diaper pants.

18. The method of claim 12, further comprising the steps of:
cutting holes in the outer substrate, wherein the holes are spaced apart from each other along the machine direction;
wherein the step of depositing the chassis further comprises depositing the chassis such that at least one hole is positioned between two consecutive chassis; and
wherein the step of folding each chassis further comprises folding the outer substrate.

19. The method of claim 12, further comprising the step of gripping a leading end region of the continuous length of absorbent chassis on a knife roll by at least one of applying a vacuum force and applying a friction force to the leading end region.

20. The method of claim 19, further comprising the step of gripping a trailing end region of the chassis on the knife roll by at least one of applying a vacuum force and applying a friction force to the trailing end region.

* * * * *